United States Patent
Rocco et al.

(10) Patent No.: US 10,166,221 B2
(45) Date of Patent: Jan. 1, 2019

(54) FORMULATIONS OF AN LSD1 INHIBITOR

(71) Applicant: Incyte Corporation, Wilmington, DE (US)

(72) Inventors: William L. Rocco, Reading, PA (US); Ying Liu, Exton, PA (US); Mei Li, Newark, DE (US); Tanvi Shah, Philadelphia, PA (US); Huifang Wu, West Chester, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 15/493,514

(22) Filed: Apr. 21, 2017

(65) Prior Publication Data

US 2017/0304282 A1  Oct. 26, 2017

Related U.S. Application Data

(60) Provisional application No. 62/326,254, filed on Apr. 22, 2016.

(51) Int. Cl.
*A61K 31/445* (2006.01)
*A61K 9/00* (2006.01)
*A61K 9/20* (2006.01)
*A61K 9/48* (2006.01)

(52) U.S. Cl.
CPC .......... *A61K 31/445* (2013.01); *A61K 9/0053* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 9/2095* (2013.01); *A61K 9/485* (2013.01); *A61K 9/4833* (2013.01); *A61K 9/4858* (2013.01); *A61K 9/4866* (2013.01)

(58) Field of Classification Search
CPC .................................................. A61K 31/445
See application file for complete search history.

(56) References Cited

U.S. PATENT DOCUMENTS

| | | | |
|---|---|---|---|
| 5,658,857 A | 8/1997 | Andree et al. | |
| 8,115,000 B2 | 2/2012 | Rajagopalan et al. | |
| 8,349,210 B2 | 1/2013 | Xu et al. | |
| 8,546,394 B2 | 10/2013 | Li | |
| 8,853,408 B2 | 10/2014 | Johnson | |
| 9,493,442 B2 | 11/2016 | Wu et al. | |
| 9,493,450 B2 | 11/2016 | Wu et al. | |
| 9,527,835 B2 | 12/2016 | Wu et al. | |
| 9,670,210 B2 | 6/2017 | Wu et al. | |
| 9,695,167 B2 | 7/2017 | Wu et al. | |
| 9,695,168 B2 | 7/2017 | Wu et al. | |
| 9,695,180 B2 | 7/2017 | Wu et al. | |
| 9,758,523 B2 | 9/2017 | Wu et al. | |
| 9,944,647 B2 | 4/2018 | He et al. | |
| 9,994,546 B2 | 6/2018 | Wu et al. | |
| 2002/0151549 A1 | 10/2002 | Hayakawa et al. | |
| 2004/0023972 A1 | 2/2004 | Sundermann et al. | |
| 2004/0058938 A1 | 3/2004 | Cullmann et al. | |
| 2004/0082635 A1 | 4/2004 | Hashimoto et al. | |
| 2004/0082781 A1 | 4/2004 | Hibi et al. | |
| 2004/0220189 A1 | 11/2004 | Sun et al. | |
| 2005/0009832 A1 | 1/2005 | Sun et al. | |
| 2005/0113283 A1 | 5/2005 | Solow-Cordero et al. | |
| 2006/0178399 A1 | 8/2006 | Nishizawa et al. | |
| 2006/0194842 A1 | 8/2006 | Uchida et al. | |
| 2007/0004772 A1 | 1/2007 | Sun et al. | |
| 2007/0191395 A1 | 8/2007 | Kawakami | |
| 2008/0249154 A1 | 10/2008 | Ohmoto et al. | |
| 2009/0203690 A1 | 8/2009 | Akritopoulou-Zanze et al. | |
| 2009/0318436 A1 | 12/2009 | Albrecht et al. | |
| 2010/0113441 A1 | 5/2010 | Siegel et al. | |
| 2011/0105457 A1 | 5/2011 | Taniyama et al. | |
| 2011/0112067 A1 | 5/2011 | Hartmann et al. | |
| 2012/0004262 A1 | 1/2012 | Guibourt et al. | |
| 2012/0108500 A1 | 5/2012 | Sakane et al. | |
| 2012/0220582 A1 | 8/2012 | Mitchell et al. | |
| 2012/0283266 A1 | 11/2012 | Ortega Munoz et al. | |
| 2012/0322877 A1 | 12/2012 | Casero et al. | |
| 2013/0035377 A1 | 2/2013 | Minucci et al. | |
| 2013/0040946 A1 | 2/2013 | Siegel et al. | |
| 2013/0090386 A1 | 4/2013 | Ortega Munoz et al. | |
| 2013/0095067 A1 | 4/2013 | Baker et al. | |
| 2013/0109751 A1 | 5/2013 | Salvatore | |
| 2013/0197013 A1 | 8/2013 | Fyfe et al. | |
| 2013/0203754 A1 | 8/2013 | Yang et al. | |
| 2013/0217878 A1 | 8/2013 | Lizuka et al. | |

(Continued)

FOREIGN PATENT DOCUMENTS

| | | |
|---|---|---|
| CA | 2831143 | 10/2012 |
| CA | 2844525 | 2/2013 |

(Continued)

OTHER PUBLICATIONS

Berge et al., J. Pharm. Sci., 1977, 66(1), 1-19.*
"LSD1 inhibitors of Lysine specific demethylase 1, a novel target in neurodegenerative disease," Powerpoint presentation, Oryzon, Feb. 2011, 42 pages.
Abdulla et al., "Natural Polyphenols Inhibit Lysine-Specific Demethylase-1 in vitro," Journal of Biochemical and Pharamcological Research, Mar. 2013, 1: 56-63.
Adamo et al., "LSD1 and pluripotency: a new player in the network," Cell Cycle, Oct. 2011, 10(19): 3215-6.

(Continued)

*Primary Examiner* — Svetlana M Ivanova
(74) *Attorney, Agent, or Firm* — Fish & Richardson P.C.

(57) ABSTRACT

The present application relates to pharmaceutical formulations and dosage forms of a lysine specific demethylase-1 (LSD1) inhibitor, or a pharmaceutically acceptable salt, solvate, or hydrate thereof, including methods of preparation thereof, which are useful in the treatment of LSD1 mediated diseases such as cancer.

37 Claims, 18 Drawing Sheets

(56) References Cited

U.S. PATENT DOCUMENTS

| | | |
|---|---|---|
| 2013/0231342 A1 | 9/2013 | Munoz et al. |
| 2013/0303545 A1 | 11/2013 | Maes et al. |
| 2014/0011857 A1 | 1/2014 | Casero et al. |
| 2014/0018393 A1 | 1/2014 | Johnson et al. |
| 2014/0094445 A1 | 4/2014 | Vakayalapati et al. |
| 2014/0206757 A1 | 7/2014 | Shi et al. |
| 2014/0213657 A1 | 7/2014 | Munoz et al. |
| 2014/0228405 A1 | 8/2014 | Tomita et al. |
| 2014/0256742 A1 | 9/2014 | Baker et al. |
| 2014/0296255 A1 | 10/2014 | Maes et al. |
| 2014/0329833 A1 | 11/2014 | Maes et al. |
| 2014/0343118 A1 | 11/2014 | McCafferty et al. |
| 2015/0065434 A1 | 3/2015 | Woster et al. |
| 2015/0065495 A1 | 3/2015 | Vankayalapati et al. |
| 2015/0133564 A1 | 5/2015 | Oh et al. |
| 2015/0225375 A1 | 8/2015 | Wu et al. |
| 2015/0225379 A1 | 8/2015 | Wu et al. |
| 2015/0225394 A1 | 8/2015 | Wu et al. |
| 2015/0225401 A1 | 8/2015 | Wu et al. |
| 2015/0232436 A1 | 8/2015 | Baker et al. |
| 2016/0009711 A1 | 1/2016 | Wu et al. |
| 2016/0009712 A1 | 1/2016 | Wu et al. |
| 2016/0009720 A1 | 1/2016 | Wu et al. |
| 2016/0009721 A1 | 1/2016 | Wu et al. |
| 2016/0289238 A1 | 4/2016 | He et al. |
| 2017/0044101 A1 | 2/2017 | Pan et al. |
| 2017/0112816 A1 | 4/2017 | Wu et al. |
| 2017/0121302 A1 | 5/2017 | Wu et al. |
| 2017/0158633 A1 | 6/2017 | Wu et al. |
| 2017/0342070 A1 | 11/2017 | Wu et al. |
| 2017/0362245 A1 | 12/2017 | Wu et al. |
| 2017/0369487 A1 | 12/2017 | Wu et al. |
| 2017/0369488 A1 | 12/2017 | Wu et al. |
| 2017/0369497 A1 | 12/2017 | Wu et al. |

FOREIGN PATENT DOCUMENTS

| | | | |
|---|---|---|---|
| CA | 2887598 | 4/2014 | |
| CN | 103054869 | 4/2013 | |
| CN | 103124724 | 5/2013 | |
| CN | 103373996 | 10/2013 | |
| CN | 103893163 | 7/2014 | |
| CN | 103933036 | 7/2014 | |
| CN | 103961340 | 8/2014 | |
| CN | 104119280 | 10/2014 | |
| DE | 102006041292 | 3/2008 | |
| EP | 0404190 | 12/1990 | |
| EP | 0430385 | 6/1991 | |
| EP | 2168579 | 3/2010 | |
| EP | 2168579 A1 * | 3/2010 | ............. A61K 9/145 |
| EP | 2524918 | 11/2012 | |
| EP | 2740474 | 6/2014 | |
| EP | 2743256 | 6/2014 | |
| FR | 2662163 | 11/1991 | |
| FR | 2920090 | 2/2009 | |
| FR | 2920091 | 2/2009 | |
| JP | 2000319277 | 11/2000 | |
| JP | 2000319278 | 11/2000 | |
| JP | 2001006877 | 1/2001 | |
| JP | 2001035664 | 2/2001 | |
| JP | 2001057292 | 2/2001 | |
| JP | 2001114780 | 4/2001 | |
| JP | 2005089352 | 4/2005 | |
| JP | 2010070503 | 4/2010 | |
| WO | WO 1988/004298 | 6/1988 | |
| WO | WO 1993/025553 | 12/1993 | |
| WO | WO 1994/018198 | 8/1994 | |
| WO | WO 1995/012594 | 5/1995 | |
| WO | WO 1999/024434 | 5/1999 | |
| WO | WO 2001/27119 | 4/2001 | |
| WO | WO 2001/83481 | 8/2001 | |
| WO | WO 2002/000196 | 1/2002 | |
| WO | WO 2002/06286 | 1/2002 | |
| WO | WO 2002/034748 | 5/2002 | |
| WO | WO 2002/38562 | 5/2002 | |
| WO | WO 2002/051831 | 7/2002 | |
| WO | WO 2002/072549 | 9/2002 | |
| WO | WO 2003/006471 | 1/2003 | |
| WO | WO 2003/044021 | 5/2003 | |
| WO | WO 2003/062392 | 7/2003 | |
| WO | WO 2004/017950 | 3/2004 | |
| WO | WO 2004/021989 | 3/2004 | |
| WO | WO 2004/058762 | 7/2004 | |
| WO | WO 2004/072081 | 8/2004 | |
| WO | WO 2004/074290 | 9/2004 | |
| WO | WO 2004/089380 | 10/2004 | |
| WO | WO 2004/089416 | 10/2004 | |
| WO | WO 2004/096131 | 11/2004 | |
| WO | WO 2004/108692 | 12/2004 | |
| WO | WO 2005/007658 | 1/2005 | |
| WO | WO 2005/025558 | 3/2005 | |
| WO | WO 2005/035532 | 4/2005 | |
| WO | WO 2005/042537 | 5/2005 | |
| WO | WO 2005/044793 | 5/2005 | |
| WO | WO 2005/097052 | 10/2005 | |
| WO | WO 2006/015263 | 2/2006 | |
| WO | WO 2006/018727 | 2/2006 | |
| WO | WO 2006/038116 | 4/2006 | |
| WO | WO 2006/057946 | 6/2006 | |
| WO | WO 2006/058752 | 6/2006 | |
| WO | WO 2006/073938 | 7/2006 | |
| WO | WO 2006/074041 | 7/2006 | |
| WO | WO 2006/113704 | 10/2006 | |
| WO | WO 2006/131003 | 12/2006 | |
| WO | WO 2006/135667 | 12/2006 | |
| WO | WO 2006/135795 | 12/2006 | |
| WO | WO 2006/138695 | 12/2006 | |
| WO | WO 2006/138734 | 12/2006 | |
| WO | WO 2007/022529 | 2/2007 | |
| WO | WO 2007/028051 | 3/2007 | |
| WO | WO 2007/058942 | 5/2007 | |
| WO | WO 2007/074491 | 7/2007 | |
| WO | WO 2007/095588 | 8/2007 | |
| WO | WO 2007/113226 | 10/2007 | |
| WO | WO 2007/145921 | 12/2007 | |
| WO | WO 2007/149478 | 12/2007 | |
| WO | WO 2008/005262 | 1/2008 | |
| WO | WO 2008/005423 | 1/2008 | |
| WO | WO 2008/005908 | 1/2008 | |
| WO | WO 2008/008539 | 1/2008 | |
| WO | WO 2008/011560 | 1/2008 | |
| WO | WO 2008/027812 | 3/2008 | |
| WO | WO 2008/037607 | 4/2008 | |
| WO | WO 2008/045393 | 4/2008 | |
| WO | WO 2008/056176 | 5/2008 | |
| WO | WO 2008/064157 | 5/2008 | |
| WO | WO 2008/065198 | 6/2008 | |
| WO | WO 2008/113559 | 9/2008 | |
| WO | WO 2008/125111 | 10/2008 | |
| WO | WO 2008/130951 | 10/2008 | |
| WO | WO 2008/141239 | 11/2008 | |
| WO | WO 2008/154241 | 12/2008 | |
| WO | WO 2008/156614 | 12/2008 | |
| WO | WO 2008/157752 | 12/2008 | |
| WO | WO 2009/010530 | 1/2009 | |
| WO | WO 2009/017701 | 2/2009 | |
| WO | WO 2009/017954 | 2/2009 | |
| WO | WO 2009/023179 | 2/2009 | |
| WO | WO 2009/045753 | 4/2009 | |
| WO | WO 2009/047514 | 4/2009 | |
| WO | WO 2009/047563 | 4/2009 | |
| WO | WO 2009/048993 | 4/2009 | |
| WO | WO 2009/048993 A2 * | 4/2009 | ........... A61K 9/0056 |
| WO | WO 2009/085230 | 7/2009 | |
| WO | WO 2009/085980 | 7/2009 | |
| WO | WO 2009/091374 | 7/2009 | |
| WO | WO 2009/114180 | 9/2009 | |
| WO | WO 2009/114512 | 9/2009 | |
| WO | WO 2009/128520 | 10/2009 | |
| WO | WO 2010/010184 | 1/2010 | |
| WO | WO 2010/010187 | 1/2010 | |
| WO | WO 2010/010188 | 1/2010 | |
| WO | WO 2010/010189 | 1/2010 | |
| WO | WO 2010/019899 | 2/2010 | |

(56) References Cited

FOREIGN PATENT DOCUMENTS

| | | |
|---|---|---|
| WO | WO 2010/033906 | 3/2010 |
| WO | WO 2010/036380 | 4/2010 |
| WO | WO 2010/043721 | 4/2010 |
| WO | WO 2010/048149 | 4/2010 |
| WO | WO 2010/064020 | 6/2010 |
| WO | WO 2010/084160 | 7/2010 |
| WO | WO 2010/088368 | 8/2010 |
| WO | WO 2010/091067 | 8/2010 |
| WO | WO 2010/104306 | 9/2010 |
| WO | WO 2010/108059 | 9/2010 |
| WO | WO 2010/113942 | 10/2010 |
| WO | WO 2010/119264 | 10/2010 |
| WO | WO 2010/136438 | 12/2010 |
| WO | WO 2010/144571 | 12/2010 |
| WO | WO 2010/151711 | 12/2010 |
| WO | WO 2011/022439 | 2/2011 |
| WO | WO 2011/033265 | 3/2011 |
| WO | WO 2011/035941 | 3/2011 |
| WO | WO 2011/042217 | 4/2011 |
| WO | WO 2011/050245 | 4/2011 |
| WO | WO 2011/089400 | 7/2011 |
| WO | WO 2011/097607 | 8/2011 |
| WO | WO 2011/106105 | 9/2011 |
| WO | WO 2011/106106 | 9/2011 |
| WO | WO 2011/112766 | 9/2011 |
| WO | WO 2011/113606 | 9/2011 |
| WO | WO 2011/113862 | 9/2011 |
| WO | WO 2011/121137 | 10/2011 |
| WO | WO 2011/131576 | 10/2011 |
| WO | WO 2011/131697 | 10/2011 |
| WO | WO 2011/141713 | 11/2011 |
| WO | WO 2011/143365 | 11/2011 |
| WO | WO 2011/160548 | 12/2011 |
| WO | WO 2012/003392 | 1/2012 |
| WO | WO 2012/007345 | 1/2012 |
| WO | WO 2012/013727 | 2/2012 |
| WO | WO 2012/013728 | 2/2012 |
| WO | WO 2012/016133 | 2/2012 |
| WO | WO 2012/034116 | 3/2012 |
| WO | WO 2012/042042 | 4/2012 |
| WO | WO 2012/047852 | 4/2012 |
| WO | WO 2012/052730 | 4/2012 |
| WO | WO 2012/052745 | 4/2012 |
| WO | WO 2012/054233 | 4/2012 |
| WO | WO 2012/071469 | 5/2012 |
| WO | WO 2012/072713 | 6/2012 |
| WO | WO 2012/080230 | 6/2012 |
| WO | WO 2012/080232 | 6/2012 |
| WO | WO 2012/080234 | 6/2012 |
| WO | WO 2012/080236 | 6/2012 |
| WO | WO 2012/080476 | 6/2012 |
| WO | WO 2012/080729 | 6/2012 |
| WO | WO 2012/088411 | 6/2012 |
| WO | WO 2012/088438 | 6/2012 |
| WO | WO 2012/100229 | 7/2012 |
| WO | WO 2012/107498 | 8/2012 |
| WO | WO 2012/107499 | 8/2012 |
| WO | WO 2012/116237 | 8/2012 |
| WO | WO 2012/129562 | 9/2012 |
| WO | WO 2012/135113 | 10/2012 |
| WO | WO 2012/147890 | 11/2012 |
| WO | WO 2012/156531 | 11/2012 |
| WO | WO 2012/156537 | 11/2012 |
| WO | WO 2012/176856 | 12/2012 |
| WO | WO 2012/177606 | 12/2012 |
| WO | WO 2013/010380 | 1/2013 |
| WO | WO 2013/025805 | 2/2013 |
| WO | WO 2013/033515 | 3/2013 |
| WO | WO 2013/033688 | 3/2013 |
| WO | WO 2013/053690 | 4/2013 |
| WO | WO 2013/057320 | 4/2013 |
| WO | WO 2013/057322 | 4/2013 |
| WO | WO 2013/074390 | 5/2013 |
| WO | WO 2013/085877 | 6/2013 |
| WO | WO 2013/131609 | 9/2013 |
| WO | WO 2013/147711 | 10/2013 |
| WO | WO 2014/002051 | 1/2014 |
| WO | WO 2014/009296 | 1/2014 |
| WO | WO 2014/058071 | 4/2014 |
| WO | WO 2014/078479 | 5/2014 |
| WO | WO 2014/084298 | 6/2014 |
| WO | WO 2014/085613 | 6/2014 |
| WO | WO 2014/086790 | 6/2014 |
| WO | WO 2014/127350 | 8/2014 |
| WO | WO 2014/138791 | 9/2014 |
| WO | WO 2014/164867 | 10/2014 |
| WO | WO 2014/194280 | 12/2014 |
| WO | WO 2014/205213 | 12/2014 |
| WO | WO 2013/022047 | 3/2015 |
| WO | WO 2015/031564 | 3/2015 |
| WO | WO 2015/089192 | 6/2015 |
| WO | WO 2015/123465 | 8/2015 |
| WO | WO 2015123456 A1 * 8/2015 ............ A61K 35/02 |
| WO | WO 2015/156417 | 10/2015 |
| WO | WO 2015/181380 | 12/2015 |
| WO | WO 2016/007722 | 1/2016 |
| WO | WO 2016/007727 | 1/2016 |
| WO | WO 2016/007731 | 1/2016 |
| WO | WO 2016/007736 | 1/2016 |
| WO | WO 2017/027678 | 2/2017 |
| WO | WO 2017/130933 | 8/2017 |

OTHER PUBLICATIONS

Adamo et al., "LSD1 regulates the balance between self-renewal and differentiation in human embryonic stem cells," Nat. Cell Biol, Jun. 2011, 13(6): 652-9.

Anand and Marmorstein, "Structure and mechanism of lysine-specific demethylase enzymes," J Biol Chem, Dec. 2007, 282(49): 35425-9.

Baron et al., "Molecular Mimicry and Ligand Recognition in Binding and Catalysis by the Histone Demethylase LSD1-CoREST Complex," Structure, Feb. 2011, 19: 212-220.

Bauer et al., "Reawakening fetal hemoglobin: prospects for new therapies for the β-globin disorders," Blood, Oct. 2012, 120(15): 3945-53.

Beck and Blanpain, "Unravelling cancer stem cell potential," Nat Rev Cancer, Oct. 2013, 13(10): 727-38.

Benelkebir et al., "Enantioselective synthesis of tranylcypromine analogues as lysine demethylase (LSDI) inhibitors," Bioorganic & Medicinal Chemistry, 2011, 19: 3709-3716.

Bennani-Baiti et al., "Lysine-specific demethylase 1 (LSD1/KDM1A/AOF2/BHC110) is expressed and is an epigenetic drug target in chondrosarcoma, Ewing's sarcoma, osteosarcoma, and rhabdomyosarcoma," Hum Pathol, Aug. 2012, 43(8): 1300-7.

Berge and Robiette, "Development of a Regioselective N-Methylation of (Benz)imidazoles Providing the More Sterically Hindered Isomer," The Journal of Organic Chemistry, 2013, A-D.

Berge et al., "Pharmaceutical salts," J Pharm Sci, 1977, 66(1): 1-19.

Binda et al., "Biochemical, Structural, and Biological Evaluation of Tranylcypromine Derivatives as Inhibitors of Histone Demethylases LSD1 and LSD2," J. Am. Chem. Soc., 2010, 132: 6827-6833.

Binda et al., "Molecular Insights into Human Monoamine Oxidase B Inhibition by the Glitazone Antidiabetes Drugs," ACS Med. Chem. Letter, 2012, 3: 39-42.

Blom et al., "Optimizing Preparative LC/MS Configurations and Methods for Parallel Synthesis Purification," J. Comb. Chem., 2003, 5(5): 670-683.

Blom et al., "Preparative LC-MS Purification: Improved Compound-Specific Method Optimization," J. Comb. Chem., 2004, 6(6): 874-883.

Blom, "Two-Pump at-Column-Dilution Configuration for Preparative Liquid Chomratography-Mass Spectrometry," J. Comb. Chem, 2002, 4(4): 295-301.

Cain, "AML takes LSD1," SciBX, Apr. 2012, 1-3.

Carey, FA. Organic Chemistry 6th Ed. McGraw Hill. 2006, chapter 1, p. 9.

Cao et al., "One-Pot Regiospecific Synthesis of Imidazo[1,2-a]pyridines: A Novel, Metal-Free, Three-Component Reaction for the Formation of C—N, C—O, and C—S Bonds," Org. Lett., 2013, A-D.

(56) References Cited

OTHER PUBLICATIONS

Chen and Flies, "Molecular mechanisms of T cell co-stimulation and co-inhibition," Nat Rev Immunol, Apr. 2013, 13(4): 227-42.
Chen et al., "Crystal structure of human histone lysine-specific demethylase 1 (LSD1)," Proc Natl Acad Sci USA, Sep. 2006, 103(38): 13956-61.
Chen et al., "Lysine-specific histone demethylase 1 (LSD1): A potential molecular target for tumor therapy," Crit Rev Eukaryot Gene Expre, 2012, 22(1): 53-9.
Chilean Office Action in Chilean Application No. 2021-2016, dated Jan. 18, 2017, 3 pages (English Translation).
Cho et al., "Demethylation of RB regulator MYPT1 by histone demethylase LSD1 promotes cell cycle progression in cancer cells," Cancer Res., Feb. 2011, 71(3): 655-60.
Clevers, "The cancer stem cell: premises, promises and challenges," Nat Med., Mar. 2011, 17(3): 313-9.
Crea et al., "The emerging role of histone lysine demethylases in prostate cancer," Mol Cancer, Aug. 2012, 11:52.
Cui et al., "The LSD1 inhibitor RN-1 induces fetal hemoglobin synthesis and reduces disease pathology in sickle cell mice," Blood, 2015, 1-31.
Culhane and Cole, "LSD1 and the chemistry of histone demethylation," Current Opinion in Chemical Biology, 2007, 11: 561-568.
Culhane et al., "A Mechanism-Based Inactivator for Histone Demethylase LSD1," J. Am. Chem. Soc., 2006, 128: 4536-4537.
Culhane et al., "Comparative Analysis of Small Molecules and Histone Substrate Analogues as LSD1 Lysine Demthylase Inhibitors," J. Am. Chem. Soc., 2010, 132: 3164-3176.
Dancy et al., "Azalysine Analogues as Probes for Protein Lysine Deacetylation and Demethylation," J. Am. Chem. Soc., 2012, 5138-5148.
Dawson and Kouzarides, "Cancer epigenetics: from mechanism to therapy," Cell, Jul. 2012, 150(1): 12-27.
Dhanak, "Cracking the Code: The Promise of Epigenetics," ACS Med. Chem. Letter, 2012, 3: 521-523.
Dhudshia and Thadani, "Diastereoselective allylation and crotylation of N-unsubstituted imines derived from ketones," Chem. Commun., 2005, 33 pages.
Dhudshia et al., "Diastereoselective allylation and crotylation of N-unsubstituted imines derived from ketones," Chem Commun, 2005, 5551-5553.
Ding et al., "LSD1-mediated epigenetic modification contributes to proliferation and metastasis of colon cancer," Br J Cancer, Aug. 2013, 109(4): 994-1003.
Dulla et al., "Synthesis and evaluation of 3-amino/guanidine substituted phenyl oxazoles as a novel class of LSD1 inhibitors with anti-proliferative properties," The Royal Society of Chemistry, 2013, 1-25.
Eurasian Office Action in Eurasian Application No. 201691620, dated Mar. 16, 2017, 6 pages. (English Translation).
Eurasian Office Action in Eurasian Application No. 201691594, dated Sep. 27, 2017, 4 pages. (English Translation).
Ellsworth et al., "Reductions in log P Improved Protein Binding and Clearance Predictions Enabling the Prospective Design of Cannabinoid Receptor (CB1) Antagonists with Desired Pharmacokinetic Properties," J. Med. Chem., 2013, 56: 9586-9600.
Fiskus et al., "Pre-Clinical Efficacy of Combined Therapy with LSD1 Antagonist SP-2509 and Pan-Histone Deacetylase Inhibitor Against AML Blast Pregenitor Cells," 54th ASH Annual Meeting and Exposition, session 604, poster abstract Dec. 2012, [retrieved on May 1, 2013]. Retrieved from the Internet at URL: https://ash.confex.com/ash/2012/webprogram/Paper53429.html, 2 pages.
Forneris et al., "LSD1: oxidative chemistry for multifaceted functions in chormatin regulation," Cell Press, Mar. 2008, 181-189.
Forneris, F., et al., *Structural basis of LSD1-CoREST selectivity in histone H3 recognition.* J Biol Chem, 2007. 282(28): p. 20070-4.
Ganesan, "Targeting Epigenetic Demethylation," University of East Anglia (School of Pharmacy), PowerPoint presentation, Presented from the World Epigenetics Summit, London, Jul. 24, 2012, 26 pages.

Ge et al., "Pd-Catalyzed α-Arylation of α,α-Difluoroketones with Aryl Bromides and Chlorides. A Route to Difluoromethylarenes," J. Am. Chem. Soc., 2014, A-D.
Gonzalez et al., "Selective and Potent Morpholinone Inhibitors of the MDM2-p53 Protein-Protein Interaction," J. Med. Chem., 2013, A-Q.
Gooden et al., "Facile synthesis of substituted trans-2-arylcyclopropylamine inhibitors of the human histone demethylase LSD1 and monoamine oxidases A and B," Bioorganic & Medicinal Chemistry Letters, 2008, 18: 3047-3051.
Greaves and Gribben, "The role of B7 family molecules in hematologic malignancy," Blood, Jan. 2013, 121(5): 734-44.
Gui et al., "C—H Methylation of Heteroarenes Inspired by Radical SAM Methyl Transferase," J. Am. Chem. Soc., 2014, A-D.
Guiles et al. "preparation of triazolopyrimidine derivatives as P2T receptor antagonists," CA130:168386 (1999).
Hackam et al., "Translation of research evidence from animals to humans," JAMA, Oct. 2006, 296(14), 1731-1732.
Hakimi et al., "A core-BRAF35 complex containing histone deacetylase mediates repression of neuronal-specific genes," Proc Natl Acad Sci USA, May 2002, 99(11): 7420-5.
Hamada et al., "Design, Synthesis, Enzyme-Inhibitory Activity, and Effect on Human Cancer Cells of a Novel Series of Jumonji Domain-Containing Protein 2 Histone Demthylase Inhibitors," J. Med. Chem., 2010, 52: 5629-5638.
Hamilton et al., "Comparison of a Direct and Indirect Method for Measuring Flavins—Assessing Flavin Status in Patients Receiving Total Parenteral Nutrition," The Open Clinical Chemistry Journal, 2009, 2: 42-48.
Han et al., "Synergistic re-activation of epigenetically silenced genes by combinatorial inhibition of DNMTs and LSD1 in cancer cells," pLoS One, Sep. 2013, 8(9): e75136.
Harris et al., "The histone demethylase KDM1A sustains the oncogenic potential of MLL-AF9 leukemia stem cells," Cancer Cell, Apr. 2012, 21(4): 473-87.
Hayami et al., "Overexpression of LSD1 contributes to human carcinogenesis through chromatin regulation in various cancers," Int J Cancer, Feb. 2011, 128(3): 574-86.
Hazeldine et al., "Low Molecular Weight Amidoximes that Act as Potent Inhibitors of Lysine-Specific Demethylase 1," J. Med. Chem., 2012, 55: 7378-7391.
Hesp et al., "Expedient Synthesis of α-Heteroaryl Piperidines Using a Pd-Catalyzed Suzuki Cross-Coupling—Reduction Sequence," Org. Lett., 2013, A-C.
Hicken et al., "Discovery of a Novel Class of Imidazo[1,2-a]Pyridines with Potent PDGFR Activity and Oral Bioavailability," ACS Med. Chem. Lett., 2013, A-F.
Hitchin et al., "Development and evaluation of selective, reversible LSD1 inhibitors derived from fragments," Med. Chem. Commun., 2013, 4: 1513-1522.
Hoffmann et al., "The role of histone demethylases in cancer therapy," Molecular Oncology, 2012, 6: 683-703.
Hou and Yu, "Structural insights into histone lysine demethylation," Current Opinion in Structural Biology, 2010, 20: 739-748.
Hruschka et al., "Fluorinated phenylcyclopropylamines. Part 5: Effects of electron-withdrawing or -donating aryl substituents on the inhibition of monoamine oxidases A and B by 2-aryl-2-fluorocyclopropylamines," Bioorganic & Medicinal Chemistry, 2008, 16: 7148-7166.
Huang et al., "p53 is regulated by the lysine demethylase LSD1," Nature, Sep. 2007, 449(7158): 105-8.
Huang et al., "Rhodium(III)-Catalyzed Direct Selective C(5)-H Oxidative Annulations of 2-Substituted Imidazoles and Alkynes by Double C—H Activation," Organic Letters, Feb. 2013, 15(8): 1878-1881.
Improper Markush Fed. Reg. 76(27) p. 7612-75, slide 1, 64-67 (2011).
International Preliminary Report on Patentability in International Application No. PCT/US2015/015600, dated Aug. 25, 2016, 7 pages.
International Preliminary Report on Patentability in International Application No. PCT/US2015/015635, dated Aug. 16, 2016, 8 pages.

(56) References Cited

OTHER PUBLICATIONS

International Preliminary Report on Patentability in International Application No. PCT/US2015/015663, dated Aug. 16, 2016, 7 pages.
International Preliminary Report on Patentability in International Application No. PCT/US2015/015706, dated Aug. 16, 2016, 10 pages.
International Preliminary Report on Patentability in International Application No. PCT/US2015/039734, dated Jan. 10, 2017, 10 pages.
International Preliminary Report on Patentability in International Application No. PCT/US2015/039706, dated Jan. 10, 2017, 10 pages.
International Preliminary Report on Patentability in International Application No. PCT/US2015/039724, dated Jan. 10, 2017, 10 pages.
International Preliminary Report on Patentability in International Application No. PCT/US2015/039718, dated Jan. 10, 2017, 9 pages.
International Preliminary Report on Patentability in International Application No. PCT/US2016/025550, dated Oct. 2, 2017, 8 pages.
International Search Report and Written Opinion in International Application No. PCT/US2015/015600, dated May 18, 2015, 9 pages.
International Search Report and Written Opinion in International Application No. PCT/US2015/015635, dated May 8, 2015, 10 pages.
International Search Report and Written Opinion in International Application No. PCT/US2015/015663, dated May 6, 2015, 10 pages.
International Search Report and Written Opinion in International Application No. PCT/US2015/015706, dated May 6, 2015, 16 pages.
International Search Report and Written Opinion in International Application No. PCT/US2015/039718, dated Sep. 15, 2015, 13 pages.
International Search Report and Written Opinion in International Application No. PCT/US2015/039724, dated Sep. 15, 2015, 14 pages.
International Search Report and Written Opinion in International Application No. PCT/US2015/039734, dated Sep. 18, 2015, 14 pages.
International Search Report and Written Opinion in International Application No. PCT/US2016/025550, dated Aug. 30, 2016, 12 pages.
International Search Report and Written Opinion in International Application No. PCT/US2016/046497, dated Oct. 21, 2016, 13 pages.
International Search Report and Written Opinion in International Application No. PCT/US2015/039706, dated Sep. 16, 2015, 12 pages.
International Search Report and Written Opinion in International Application No. PCT/US2017/028756, dated Jul. 3, 2017, 23 pages.
Jalluri, Drug Analysis Table, LSD1 KDM1a Cortellis Update, retrieved on May 6, 2013, 3 pages.
Jordan, "Tamoxifen: A Most Unlikely Pioneering Medicine," Nature Reviews: Drug Discovery, Mar. 2003, 2:205-213.
Kahl et al., "Androgen Receptor Coactivators Lysine-Specific Histone Demethylase 1 and Four and a Half LIM Domain Protein 2 Predict Risk of Prostate Cancer Recurrence," Cancer Res., 2006, 66(23): 11341-7.
Kakizawa et al., "Histone H3 peptide based LSD1-selective inhibitors," Bioorganic & Medicinal Chemistry Letters, 2015, 25: 1925-1928.
Karytinos et al., "A novel mammalian flavin-dependent histone demethylase," J Biol Chem, Jan. 2009, 284(26): 17775-82.
Kelly and Lipshutz, "Chemoselective Reductions of Nitroaromatics in Water at Room Temperature," Org. Lett., 2013, A-D.
Kettle et al., "Diverse Heterocyclic Scaffolds as Allosteric Inhibitors of AKT," Journal of Medicinal Chemistry, Mar. 2012, 55(3): 1261-1273.

Khan et al., "An Overview of Phenylcyclopropylamine Derivatives: Biochemical and Biological Significance and Recent Developments," Medicinal Research Reviews, 2012, 874-910.
Khoury et al., "Efficient Assembly of Iminodicarboxamides by a "Truly" Four-Component Reaction," Angew. Chem. Int. Ed., 2012, 51: 10280-10283.
Kinzel et al., "Identification of MK-5710 ((8aS)-8a-methyl-1,3-dioxo-2-[(1S,2R)-2-phenylcyclo-propyl]-N-(1-phenyl-1H-pyrazol-5-yl)hexahydro-imidazo[1,5-a]pyrazine-7(1H)-carboxamide), a potent smoothened antagonist for use in Hedgehog pathway dependent malignancies, part 2," Bioorg Med Chem Lett, Aug. 2011, 21(15): 4429-35.
Kjer-Nielsen et al., "MR1 presents microbial vitamin B metabolites to MAIT cells," Nature, Nov. 2012, 491: 717-725.
Kocienski, PJ. Et al. Protecting Groups. Thieme. 2005, p. 52.
Kong et al., "Immunohistochemical expression of RBP2 and LSD1 in papillary thyroid carcinoma," Rom J Morphol Embryol, 2013, 54(3): 499-503.
Konovalov and Garcia-Bassets, "Analysis of the levels of lysine-specific demethylase 1 (LSD1) mRNA in human ovarian tumors and the effects of chemical LSD1 inhibitors in ovarian cancer cell lines," J Ovarian Res, Oct. 2013, 6(1): 75.
Kontaki and Talianidis, "Lysine methylation regulates E2F1-induced cell death," Mol Cell, Jul. 2010, 39(1): 152-60.
Kooistra and Helin, "Molecular mechanisms and potential functions of histone demethylases," Nat Rev Mol Cell Biol, Apr. 2012, 13(5): 297-311.
Kuroyanagi et al., "Novel anti fungal agents: Triazolopyridines as inhibitors of beta-1,6-glucan synthesis," Bioorgan ic & Medicinal Chemistry, Aug. 2010, 18(16):5845-5854.
Kuroyanagi et al., "1,3-Benzoxazole-4-carbonitrile as a novel antifungal scaffold of beta-1,6-glucan synthesis inhibitors," Bioorganic & Medicinal Chemistry, Nov. 2010, 18(21):7593-7606.
Kutz et al "3,5-Diamino-1,2,4-triazoles as a novel scaffold for potent, reversible LSD1 (KDM1A) inhibitors," Med. Chem. Commun., 2014, 5: 1863-1870.
Lan et al., "Recognition of unmethylated histone H3 lysine 4 links BHC80 to LSD1-mediated gene repression," Nature, 2007, 718-723.
Larsen and Hartwig, "Iridium-Catalyzed C—H Borylation of Heteroarenes: Scope, Regioselectivity, Application to Late-Stage Functionalization, and Mechanism," J. Am. Chem. Soc., 2013, A-M.
Lee et al., "Functional interplay between histone demethylase and deacetylase enzymes," Mol Cell Biol, Sep. 2006, 26(17): 6395-402.
Liang et al., "A Novel Selective LSD1/KDM1A Inhibitor Epigenetically Blocks Herpes Simplex Virus Lytic Replication and Reactivation from Latency," mBio, 2013, 4(1): 1-9.
Liang et al., "Inhibition of the histone demethylase LSD1 blocks alpha-herpesvirus lytic replication and reactivation from latency," Nat Med., Nov. 2009, 15(11): 1312-7.
Liang et al., "Targeting the JMJD2 histone demethylases to epigenetically control herpesvirus infection and reactivation from latency," Sci Transl Med., Jan. 2013, 5(167): 167ra5.
Lim et al., "Lysine-specific demethylase 1 (LSD1) is highly expressed in ER-negative breast cancers and a biomarker predicting aggressive biology," Carcinogenesis, Mar. 2010, 31(3): 512-20.
Liu and Nefzi, "Solid-Phase Synthesis of N-Substituted Pyrrolidinone-Tethered N-Substituted Piperidines via Ugi Reaction," J. Comb. Chem., 2010, 12: 566-570.
Lund and van Lohuizen, "Epigenetics and cancer," Genes Dev., Oct. 2004, 18(19): 2315-35.
Lv et al., "Over-Expression of LSD1 Promotes Proliferation, Migration and Invasion in Non-Small Cell Lung Cancer," PLoS One, Apr. 2012, 7(4): 1-8, e35065.
Lynch et al., "CD86 expression as a surrogate cellular biomarker for pharmacological inhibition of the histone demethylase lysine-specific demethylase 1," Anal Biochem, Nov. 2013, 442(1): 104-6.
Lynch et al., "LSD1 Inhibition: A therapeutic strategy in cancer?," Expert Opinion on Therapeutic Targets, 2012, 16(12): 1239-1249.
Merck KGaA, "Product comparison—EMD4Biosciences," Comparison of LSD1 inhibitors, EMD Millipore USA, retrieved on May 6, 2013, 3 pages.

(56) References Cited

OTHER PUBLICATIONS

Metzger et al., "LSD1 demethylates repressive histone marks to promote androgen-receptor-dependent transcription," Nature, Sep. 2005, 437(7057): 436-9.
Mimasu et al., "Structurally Designed trans-2-Phenylcyclopropylamine Derivatives Potently Inhibit Histone Demethylase LSD1/KDM1," Biochemistry, 2010, 49: 6494-6503.
Moon et al., "Copper-Catalyzed Chan-Lam Coupling between Sulfonyl Azides and Boronic Acids at Room Temperature," Org. Lett., 2013, A-D.
Moormann et al., "Potential Antisecretory Antidiarrheals. 2. $\alpha_2$-Adrenergic 2-[(Aryloxy)alkyl]imidazolines," American Chemical Society, 1990, 33: 614-626.
Mosammaparast and Shi, "Reversal of histone methylation: biochemical and molecular mechanisms of histone demethylases," Annu Rev Biochem, 2010, 79: 155-79.
Mulder et al., "Development of a Safe and Economical Synthesis of Methyl 6-Chloro-5-(trifluoromethyl)nicotinate: Trifluoromethylation on Kilogram Scale," Org. Process Res. Dev., 2013, 940-945.
Neelamegam et al., "Brain-penetrant LSD1 inhibitors can block memory consolidation," Supplementary Data, 2012, 24 pages.
Neelamegam et al., "Brain-Penetrant LSD1 Inhibitors Can Block Memory Consolidation," ACS Chem. Neurosci., 2012, 3:120-128.
Ogasawara et al., "Lysine-Specific Demethylase 1-Selective Inactivators: Protein-Targeted Drug Delivery Mechanism," Angew. Chem. Int. Ed., 2013, 52: 8620-8624.
Ogasawara et al., "Lysine-Specific Demethylase 1-Selective Inactivators: Protein-Targeted Drug Delivery, Mechanism," Supporting Information.
Patani et al., "Bioisosterism: A Rational Approach in Drug Design," Chemical Reviews, 1996, 96: 3147-3176.
Pitt "Heteroaromatic Rings of the Future" J. Med. Chem. 2009, 52, 2952-2963.
Portela and Esteller, "Epigenetic modifications and human disease," Nat Biotechnol, Oct. 2010, 28(10): 1057-68.
Potts et al., "The mass spectra of somes-triazolo[4,3-a]pyrazines," Organic Mass Spectrometry, Jun. 1971, 5(6): 663-674.
Pozharskii et. al. Heterocycles in Life and Society Wiley, 1997, pp. 1-6.
*Remington's Pharmaceutical Sciences*, 17$^{th}$ Ed., (Mack Publishing Company, Easton, 1985), p. 1418.
Roberston et al., "Expanding the Druggable Space of the LSD1/CoREST Epigenetic Target: New Potential Binding Regions for Drug-Like Molecules, Peptides, Protein Partners, and Chromatin," PLOS, Jul. 2013, 9(7): 1-10.
Rostom et al., "A facile synthesis of some 3-cyano-1,4,6-trisubstituted-2(1)-pyridinones and their biological evaluation as anticancer agents," Medicinal Chemistry Research, Oct. 2010, 20(8): 1260-1272.
Rotilli and Mai, "Targeting Histone Demethylases: A New Avenue for the Fight against Cancer," Genes and Cancer, 2011, 2(6): 663-679.
Sakane et al., "Activation of HIV transcription by the viral Tat protein requires a demethylation step mediated by lysine-specific demethylase 1 (LSD1/KDM1)," PLoS Pathog., Aug. 2011, 7(8):e1002184.
Salarius Pharmaceuticals (Non confidential pharmaceutical package), Oncology Epigenetic Therapy Sp-2528, an Inhibitor of Lysine-Specific Demethylase 1 (LSD1), Jan. 2012, 28 pages.
Samann et al., "Full Functionalization of the Imidazole Scaffold by Selective Metalation and Sulfoxide/Magnesium Exchange," Angew. Chem. Int. Ed., 2013, 52: 1-6.
Sankaran and Orkin, "The switch from fetal to adult hemoglobin," Cold Spring Harb Perspect Med., Jan. 2013, 3(1): a011643.
Sareddy et al., "KDM1 is a novel therapeutic target for the treatment of gliomas," Oncotarget, Jan. 2013, 4(1): 18-28.
Schenk et al., "Inhibition of the LSD1 (KDM1A) demethylase reactivates the all-trans-retinoic acid differentiation pathway in acute myeloid leukemia," Nat Med, Mar. 2012, 18(4): 605-11.
Schmitt et al., "Nonpeptidic Propargylamines as Inhibitors of Lysine Specific Demethylase 1 (LSD1) with Cellular Activity," J. Med. Chem., 2013, A-I.
Schulte et al., "Lysine-Specific Demethylase 1 is Strongly Expressed in Poorly Differentiated Neuroblastoma: Implications for Therapy," Cancer Res, 2009, 69(5): 2065-71.
Search Report, dated Jun. 3, 2014, 7 pages.
Search Report, dated May 30, 2014, 109 pages.
Search Report, dated May 30, 2014, 6 pages.
Senecal et al., "A General, Practical Palladium-Catalyzed Cyanation of (Hetero) Aryl Chlorides and Bromides," Angew. Chem. Int. Ed., 2013, 52: 1-6.
Serce et al., "Elecated expression of LSD1 (Lysine-specific demethylase 1) during tumour progression from re-invasive to invasive ductal carcinoma of the breast," BMC Clin Pathol, Aug. 2012, 12:13.
Sharma et al., "(Bis)urea and (Bis)thiourea Inhibitors of Lysine-Specific Demethylase 1 as Epigenetic Modulators," J. Med. Chem., 2010, 53: 5197-5212.
Shen and Laird, "Interplay between the cancer genome and epigenome," Cell, Mar. 2013, 153(1): 38-55.
Shi et al., "Histone demethylation mediated by the nuclear amine oxidase homolog LSD1," Cell, Dec. 2004, 119(7): 941-53.
Shi et al., "Lysine-specific demethylase 1 is a therapeutic target for fetal hemoglobin induction," Nat Med, Mar. 2013, 19(3): 291-4.
Shi et al., "Regulation of LSD1 Histone Demethylase Activity by Its Associated Factors," Molecular Cell, Sep. 2005, 19: 857-864.
Singh et al., "Inhibition of LSD1 sensitizes gliobastoma cells to histone deacetylase inhibitors," Neuro Oncol, Aug. 2011, 13(8): 894-903.
Son et al., "Structure of human monoamine oxidase A at 2.2—A resolution: The control of opening the entry for substrates/inhibitors," PNAS, Apr. 2008, 105(15): 5739-5744.
Stavropoulos et al., "Crystal structure and mechanism of human lysine-specific demethylase-1," Nat Struct Mol Biol, Jul. 2006, 13(7): 626-32.
Suikki et al., "Genetic alterations and changes in expression of histone demethylases in prostate cancer," Prostate, Jun. 2010, 70(8): 889-96.
Sun et al., "Histone demethylase LSD1 regulates neural stem cell proliferation," Mol Cell Biol, Apr. 2010, 30(8): 1997-2005.
Suzuki and Miyata, "Lysine Demethylases Inhibitors," J. Med. Chem., 2011, 54: 8236-8250.
Szewczuk et al., "Mechanistic Analysis of a Suicide Inactivator of Histone Demethylase LSD1," Biochemistry, 2007, 46: 6892-6902.
Szostak et al., "Highly Chemoselective Reduction of Amides (Primaiy, Secondary, Tertiary) to Alcohols using $SmI_2$/Amine/$H_2O$ under Mild Conditions," J. Am. Chem. Soc., 2013, A-D.
Theisen et al., "Reversible inhibition of lysine specific demethylase 1 is a novel anti-tumor strategy for poorly differentiated endometrial carcinoma," BMC Cancer, 2014, 14:752 1-12.
Tortorici et al., "Protein Recognition by Short Peptide Reversible Inhibitors of the Chromatin-Modifying LSD1/CoREST Lysine Demethylase," ACS Chem. Biol., 2013, 8(8): 1677-1682.
Ueda and Nagasawa, "Facile Synthesis of 1,2,4-Triazoles via a Copper-Catalyzed Tandem Addition-Oxidative Cyclization," J. Am. Chem. Soc., 2009, 131: 15080-15081.
Ueda et al., "Identification of Cell-Active Lysine Specific Demethylase 1-Selective Inhibitors," J. Am. Chem. Soc., 2009, 131: 17536-17537.
Vianello et al., "Synthesis, biological activity and mechanistic insights of 1-substituted cyclopropylamine derivatives: a novel class of irreversible inhibitors of histone demethylase KDM1A," European Journal of Medicinal Chemistry, 2014, 86: 352-363.
Wakefield, Basil "Fluorinated Pharmaceuticals" Innovations in Pharmaceutical Technology 2003, 74: 76-78, Online "http://web.archive.org/web/20030905122408/http://www.iptonline.com/articles/public/IPTFOUR74NP.pdf". (accessed via Wayback machine Nov. 20, 2009 showing web availability as of Sep. 2003).
Waldmann and Schneider, "Targeting histone modifications—epigenetics in cancer," Curr Opin Cell Biol, Apr. 2013, 25(2): 184-9.
Wang et al., "Novel Histone Demethylase LSD1 Inhibitors Selectively Target Cancer Cells with Pluripotent Stem Cell Properties," Cancer Res, Dec. 2011, 7238-7249.

(56) References Cited

OTHER PUBLICATIONS

Wang et al., "The lysine demethylase LSD1 (KDM1) is required for maintenance of global DNA methylation," Nat Genet, Jan. 2009, 41(1): 125-9.
Wen et al., "Triptolide induces cell-cycle arrest and apoptosis of human multiple myeloma cells in vitro via altering expression of histone demethylase LSD1 and JMJD2B," Acta Pharmacologica Sinica, 2012, 33: 109-119.
Wengryniuk et al., "Regioselective Bromination of Fused Heterocyclic N-Oxides," American Chemical Society, 2013, 15(4): 792-795.
Willmann et al., "Impairment of prostate cancer cell growth by a selective and reversible lysine-specific demethylase 1 inhibitor," Int. J. Cancer, 2012, 131: 2704-2709.
Xu et al., "Corepressor-dependent silencing of fetal hemoglobin expression by BCL11A," Proc Natl Acad Sci USA, Apr. 2013, 110(16): 6518-23.
Yang et al., "Reversible methylation of promoter-bound STAT3 by histone-modifying enzymes," Proc Natl Acad Sci USA, Dec. 2010, 107(50): 21499-504.
Yang et al., "Structural Basis for the Inhibition of the LSD1 Histone Demethylase by the Antidepressant trans-2-Phenylcyclopropylamine," Biochemistry, 2007, 46: 8058-8065.
Yang et al., "Structural basis of histone demethylation by LSD1 revealed by suicide inactivation," Nature Structural & Molecular Biology, Jun. 2007, 14(6): 535-539.
Yoshida et al., "Fluorinated Phenylcyclopropylamines. 1. Synthesis and Effect of Fluorine Substitution at the Cyclopropane Ring on Inhibition of Microbial Tyramine Oxidase," J. Med. Chem., 2004, 47: 1796-1806.
You et al., "CoREST is an integral component of the CoREST-human histone deacetylase complex," Proc Natl Acad Sci USA, Feb. 2001, 98(4): 1454-8.
Yu et al., "Energetic factos determining the binding of type I inhibitors to c-Met kinase: experimental studies and quantum mechanical calculations," Acta Pharmacologica Sinica, Nov. 2013, 34(11): 1475-1783.
Yu et al., "High expression of lysine-specific demethylase 1 correlates with poor prognosis of patients with esophageal squamous cell carcinoma," Biochem Biophys Res Commun, Jul. 2013, 437(2): 192-8.
Zhang et al., "Pluripotent stem cell protein Sox2 confers sensitivity to LSD1 inhibition in cancer cells," Cell Rep, Oct. 2013, 5(2): 445-57.
Zheng et al., "A Systematic Review of Histone Lysine-Specific Demethylase 1 and Its Inhibitors," 2015, 1-40.
Zhu et al., "Preparation of imidazolidin-2-imines and their analogs as aspartyl protease inhibitors for treating various diseases," CA149: 307842 (2008).
Cancer, definition by Medical Dictionary, p. 1 (2017).
SEER, Cancer Classification, p. 1-3 (2005).
Beta Thalasemia, p. 1-5, Wikipedia (2017).
Pringle "Overview of viruses" Merck Manual (2013).
Simone, Oncology: Introduction, Cecil Textbook of Medicine, 20th Edition, 1996 vol. 1, 1004-1010.
Vardiman, "The World Health Organization (WHO) classification of the myeloid neoplasms," Blood, 2002, 100(7): 2292-2302.
Estey, "New drug approvals in acute myeloid leukaemia: what's the best end point?" Leukemia, 2016, 30: 521-525.
Pui, "Treatment of Acute Lymphoblastic Leukemia," New England Journal of Medicine, 2006, 354: 166-78.
Krishnan, "Multiple myeloma and persistence of drug resistance in the age of novel drugs (Review)," International Journal of Oncology, 2016, 49: 33-50.
Stewart, "Novel therapeutics in multiple myeloma," Hematology, 2012, 17(S1): s105-s108.
Howington, "Treatment of Stage I and II Non-Small Cell Lung Cancer Diagnosis and Management of Lung Cancer 3rd Ed: American College of Chest Physicians Evidence-Based Clinical Practice Guidelines," Chest 2013, 143(5)(Suppl): e278S-e313S.

Socinski, "Treatment of Stave IV Non-small Cell Lung Cancer Diagnosis and Management of Lung Cancer, 3rd ed: American College of Chest Physicians Evidence-Based Clinical Practice Guideline," Chest 2013, 143(5)(Suppl): e341S-e368S.
Sanz-Garcia, "Current and advancing treatments for metastatic colorectal cancer," Expert Opinion on Biological Therapy, 2016, 16:1, 93-110.
Boniface, "Multidisciplinary management for esophageal and gastric cancer," Cancer Management and Research, 2016, 39-44.
Yoo, "New drugs in prostate cancer," Prostate Int., 2016, 4: 37-42.
Jett, "Treatment of Small Cell Lung Cancer Diagnosis and Management of Lung Cancer, 3rd ed: American College of Chest Physicians Evidence-Based Clinical Practice Guidelines," Chest 2013, 143(5)(Suppl): e400S-e419S.
Fattaneh and Devilee, "World Health Organization Classification of Tumours: Pathology and Genetics of Tumours of the Breast and Female Genital Organs," Online http://www.iarc.fr/en/publications/pdfs-online/pat-gen/bb4/BB4.pdf, accessed Nov. 4, 2016 IARCPress Lyon, 2003.
Hudis, "Triple-Negative Breast Cancer: An Unmet Medical Need," The Oncologist, 2011, 16(suppl 1): 1-11.
Gerratana, "Do platinum salts fit all triple negative breast cancers?" Cancer Treatment Reviews, 2016, 48: 34-41.
Gyawali, "Chemotherapy in locally advanced head and neck squamous cell carcinoma," Cancer Treatment Reviews, 2016, 44: 10-16.
Damia, "Contemporary pre-clinical development of anticancer agents—What are the optimal preclinical models?" European Journal of Cancer, 2009, 45: 2768-2781.
Sharma, "Cell-line based platforms to evaluate the therapeutic efficacy of candidate anticancer agents," Nature Reviews Cancer, Apr. 2010, 10: 241-253.
Ocana, "Preclinical development of molecular targeted agents for cancer," Nat. Rev. Clin. Oncol., 2011, 8: 200-209.
Ledford, "US cancer institute overhauls cell lines," Nature, Feb. 2016, 530: 391.
Johnson et al., "Relationships between drug activity in NCI preclinical in vitro and in vivo models and early clinical trials," British Journal of Cancer, 2001, 84: 1424-1431.
Rotili, "Targeting Histone Demethylases: A New Avenue for the Fight Against Cancer," J. Genes & Cancer, 2(6): 663-679.
Lynch, "LSD1 Inhibition: a therapeutic strategy in cancer?" Expert Opinion on Therapeutic Targets, 2012, 16(12): 1239-1249.
Muller and Krausslich, "Antiviral Strategies," Handbook of Experimental Pharmacology, 189(1): 1-24.
Balamuth "Ewings sarcoma" Lancet Oncology (2010), 11(2), 184-192.
Chilean Office Action in Chilean Application No. 2021-2016, dated Apr. 10, 2018, 13 pages (English Translation).
Chinese Office Action in Chinese Application No. 201580017095, dated Mar. 30, 2018, 9 pages (English Translation).
Cui Shuaiying, "Nuclear Receptors TR2 and TR4 Recruit Multiple Epigenetic Transcriptional Corepressors That Associate Specifically with the Embryonic-Type Globin Promoters in Differentiated Adult Erythroid Cells," Molecular and Cellular Biology, Aug. 31, 2011, 31(16): 3298-3311.
Colombian Office Action in Colombian Application No. NC20160001817, dated Mar. 20, 2018, 9 pages.
Eurasian Office Action in Eurasian Application No. 201792205, dated Apr. 4, 2018, 6 pages (English Translation).
European Examination Report in European Application No. 15707007.9, dated Feb. 27, 2018, 3 pages.
International Preliminary Report on Patentability in International Application No. PCT/US2016/046497, dated Feb. 22, 2018, 8 pages.
Sankaran "Anemia: progress in molecular mechanisms and therapies," Nature Medicine, 2015, 21(3): 221-230.
Wada et al., "Overexpression of the shortest isoform of histone demethylase LSD1 primes hematopoietic stem cells for malignant transformation," Blood, Jun. 2015, 125(24): 3731-3746.
Yatim et al., "NOTCH1 Nuclear Interactome Reveals Key Regulators of Its Transcriptional Activity and Oncogenic Function," Molecular Cell, 2012, 48: 1-14.

(56) References Cited

OTHER PUBLICATIONS

Goossens et al., "Oncogenic ZEB2 activation drives sensitivy toward KDM1A inhibition in T-cell acute lymphoblastic leukemia," Blood, Feb. 2017, 129(8): 981-990.
Hu et al., "LSD1-mediated epigenetic modification is required for TAL1 function and hematopoiesis," PNAS, Jun. 2009, 106(25): 10141-10146.
Niebel et al., "Lysine-specific demethylase 1 (LSD1) in hematopoietic and lymphoid neoplasms," Blood, 2014, 124: 151-152.
Australian Examination Report in Australian Application No. 2015217119, dated Jun. 22, 2018, 4 pages.
Chinese Office Action in Chinese Application No. 201580019205. dated May 22, 2018, 14 pages (English Translation).

* cited by examiner

FORMULATIONS OF AN LSD1 INHIBITOR

FIELD OF THE INVENTION

This application relates to pharmaceutical formulations and solid dosage forms of a lysine specific demethylase-1 (LSD1) inhibitor, or a pharmaceutically acceptable salt, solvate, or hydrate thereof, including methods of preparation thereof, which are useful in the treatment of LSD1 mediated diseases such as cancer.

BACKGROUND

Overexpression of lysine specific demethylase-1 (LSD1) is frequently observed in many types of cancers, including bladder cancer, NSCLC, breast carcinomas, ovary cancer, glioma, colorectal cancer, sarcoma including chondrosarcoma, Ewing's sarcoma, osteosarcoma, and rhabdomyosarcoma, neuroblastoma, prostate cancer, esophageal squamous cell carcinoma, and papillary thyroid carcinoma. Notably, studies found over-expression of LSD1 was significantly associated with clinically aggressive cancers, for example, recurrent prostate cancer, NSCLC, glioma, breast, colon cancer, ovary cancer, esophageal squamous cell carcinoma, and neuroblastoma. In these studies, either knockdown of LSD1 expression or treatment with small molecular inhibitors of LSD1 resulted in decreased cancer cell proliferation and/or induction of apoptosis. See, e.g., Hayami, S., et al., *Overexpression of LSD1 contributes to human carcinogenesis through chromatin regulation in various cancers*. Int J Cancer, 2011. 128(3): p. 574-86; Lv, T., et al., *Overexpression of LSD1 promotes proliferation, migration and invasion in non-small cell lung cancer*. PLoS One, 2012. 7(4): p. e35065; Serce, N., et al., *Elevated expression of LSD1 (Lysine-specific demethylase 1) during tumour progression from pre-invasive to invasive ductal carcinoma of the breast*. BMC Clin Pathol, 2012. 12: p. 13; Lim, S., et al., *Lysine-specific demethylase 1 (LSD1) is highly expressed in ER-negative breast cancers and a biomarker predicting aggressive biology*. Carcinogenesis, 2010. 31(3): p. 512-20; Konovalov, S. and I. Garcia-Bassets, *Analysis of the levels of lysine-specific demethylase 1 (LSD1) mRNA in human ovarian tumors and the effects of chemical LSD1 inhibitors in ovarian cancer cell lines*. J Ovarian Res, 2013. 6(1): p. 75; Sareddy, G. R., et al., *KDM1 is a novel therapeutic target for the treatment of gliomas*. Oncotarget, 2013. 4(1): p. 18-28; Ding, J., et al., *LSD1-mediated epigenetic modification contributes to proliferation and metastasis of colon cancer*. Br J Cancer, 2013. 109(4): p. 994-1003; Bennani-Baiti, I. M., et al., *Lysine-specific demethylase 1 (LSD1/KDM1A/ AOF2/BHC110) is expressed and is an epigenetic drug target in chondrosarcoma, Ewing's sarcoma, osteosarcoma, and rhabdomyosarcoma*. Hum Pathol, 2012. 43(8): p. 1300-7; Schulte, J. H., et al., *Lysine-specific demethylase 1 is strongly expressed in poorly differentiated neuroblastoma: implications for therapy*. Cancer Res, 2009. 69(5): p. 2065-71; Crea, F., et al., *The emerging role of histone lysine demethylases in prostate cancer*. Mol Cancer, 2012. 11: p. 52; Suikki, H. E., et al., *Genetic alterations and changes in expression of histone demethylases in prostate cancer*. Prostate, 2010. 70(8): p. 889-98; Yu, Y., et al., *High expression of lysine-specific demethylase 1 correlates with poor prognosis of patients with esophageal squamous cell carcinoma*. Biochem Biophys Res Commun, 2013. 437(2): p. 192-8; Kong, L., et al., *Immunohistochemical expression of RBP2 and LSD1 in papillary thyroid carcinoma*. Rom J Morphol Embryol, 2013. 54(3): p. 499-503.

Inhibitors of LSD1 are currently being developed for the treatment of cancer. For example, the molecule 1-{[4-(methoxymethyl)-4-({[(1R,2S)-2-phenylcyclopropyl]amino}methyl)piperidin-1-yl]methyl}cyclobutanecarboxylic acid (Compound 1) and other small molecule inhibitors of LSD1 are reported in e.g., US Publication Nos.: 2015-0225394, 2015-0225375, 2015-0225401, 2015-0225379, 2016-0009720, 2016-0009711, 2016-0009712, and 2016-0009721. Accordingly, there is a need for new formulations and dosage forms of LSD1-inhibitors. The present invention is directed toward this end.

SUMMARY OF THE INVENTION

The present invention is directed to, inter alia, a pharmaceutical formulation comprising 1-{[4-(methoxymethyl)-4-({[(1R,2S)-2-phenylcyclopropyl]amino}methyl)piperidin-1-yl]methyl}cyclobutanecarboxylic acid di-tosylate salt (Compound 1 di-tosylate salt), or a solvate or hydrate thereof, and an organic acid.

The present invention is further directed to a dosage form comprising a pharmaceutical formulation provided herein.

The present invention is further directed to a method of treating a disease associated with LSD1 activity comprising administering to a patient in need thereof a therapeutically effective amount of a pharmaceutical formulation or a dosage form provided herein.

DETAILED DESCRIPTION

Figure 1:
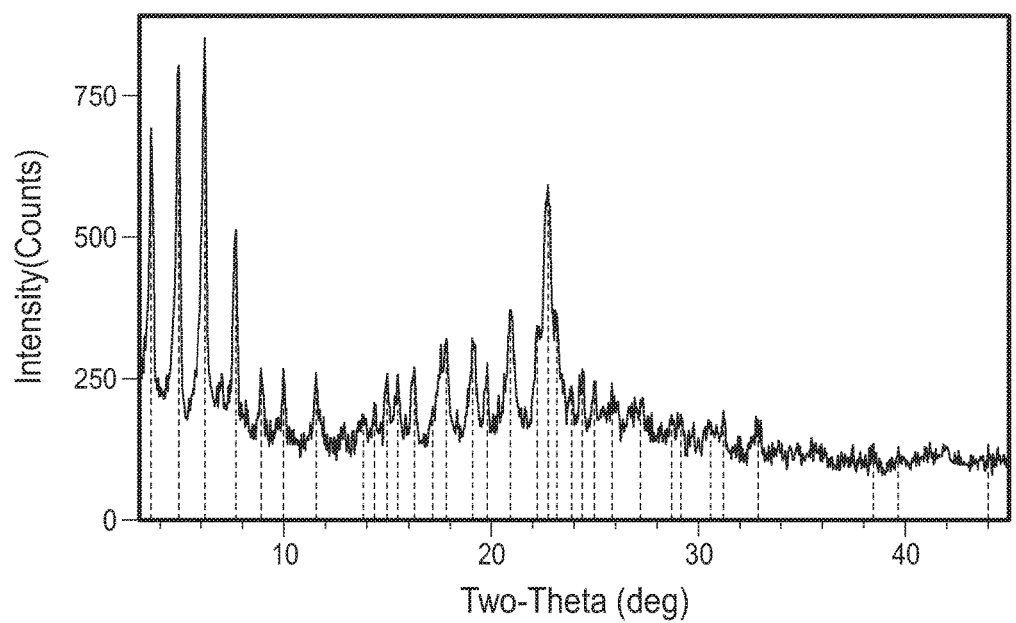
FIG. 1 shows an X-ray powder diffraction (XRPD) pattern of Compound 1 di-tosylate salt, Form I.
Figure 2:
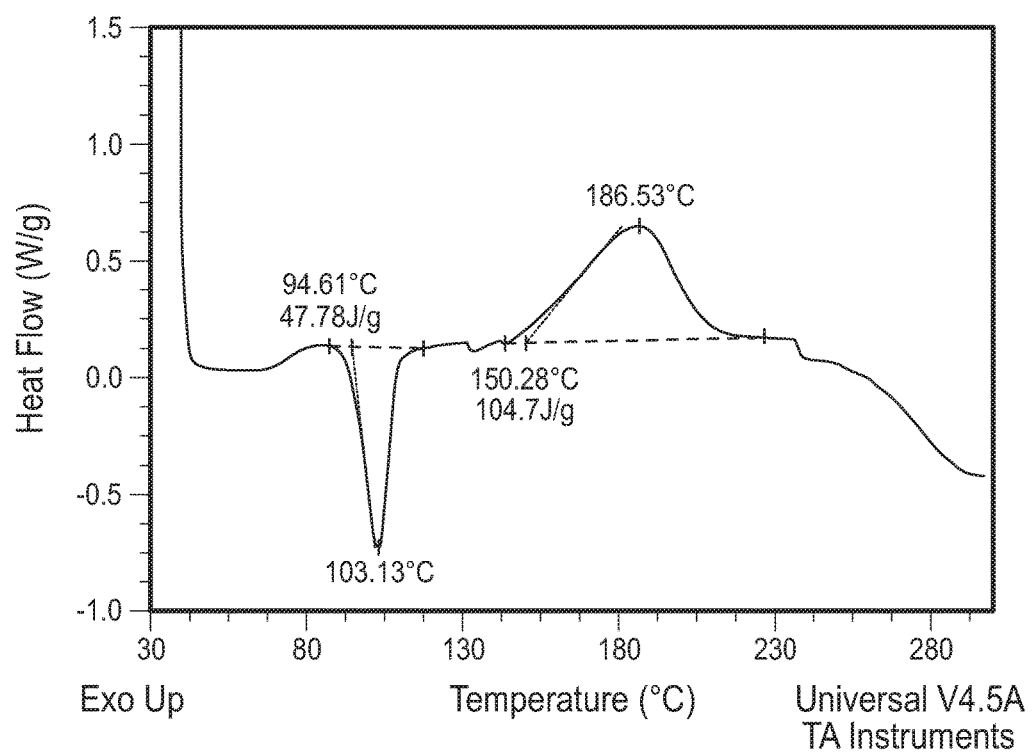
FIG. 2 shows a DSC thermogram of Compound 1 di-tosylate salt, Form I.
Figure 3:
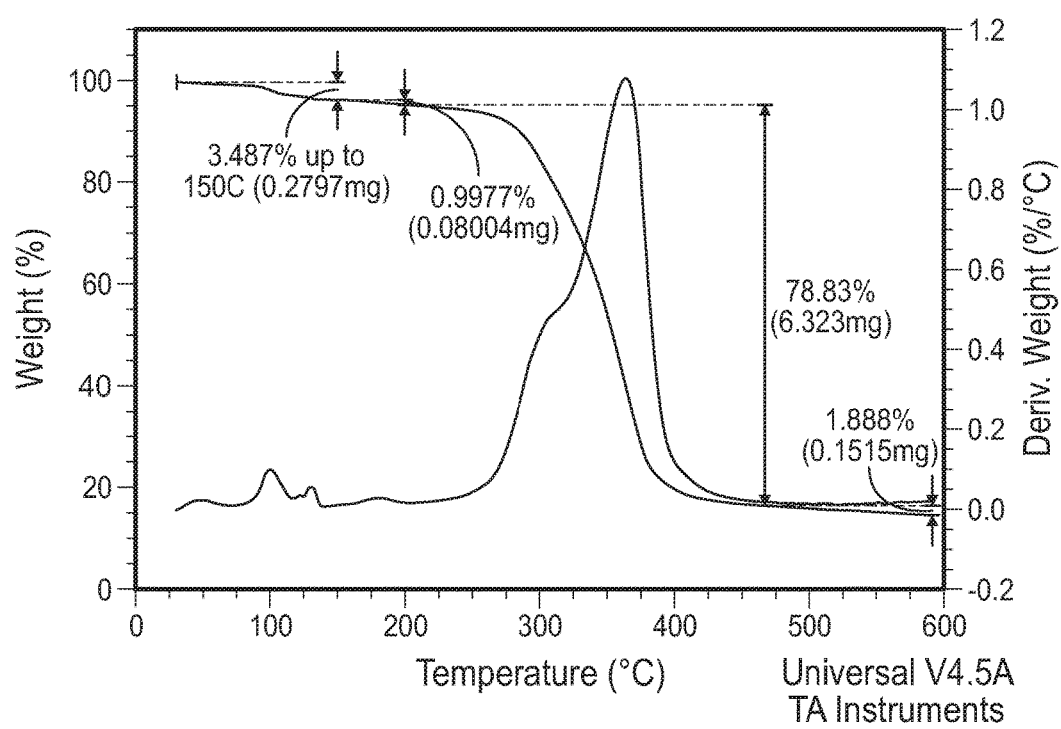
FIG. 3 shows a TGA thermogram of Compound 1 di-tosylate salt, Form I.
Figure 4:
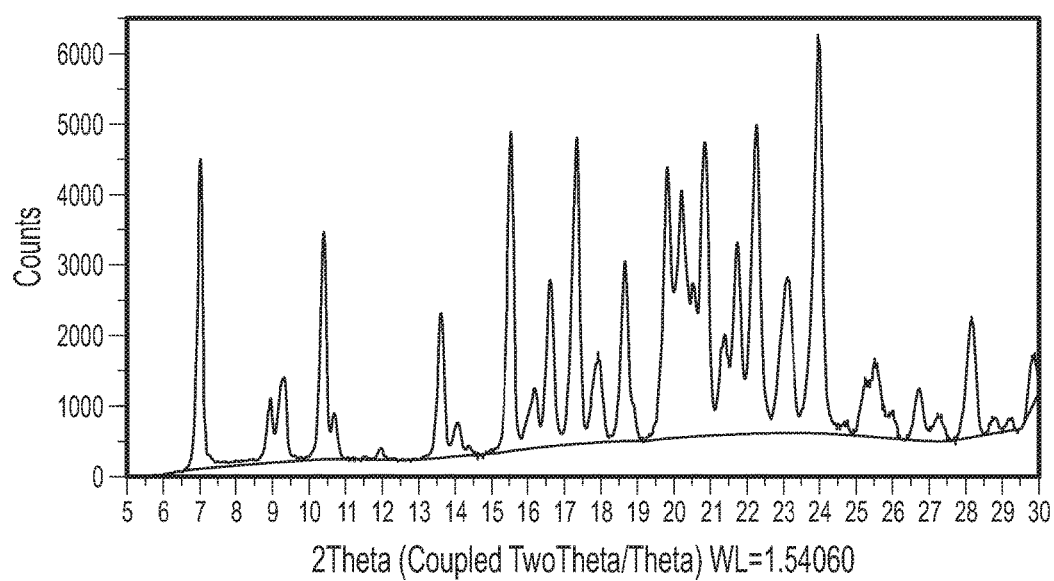
FIG. 4 shows an XRPD pattern of Compound 1 di-tosylate salt, Form HI.
Figure 5:
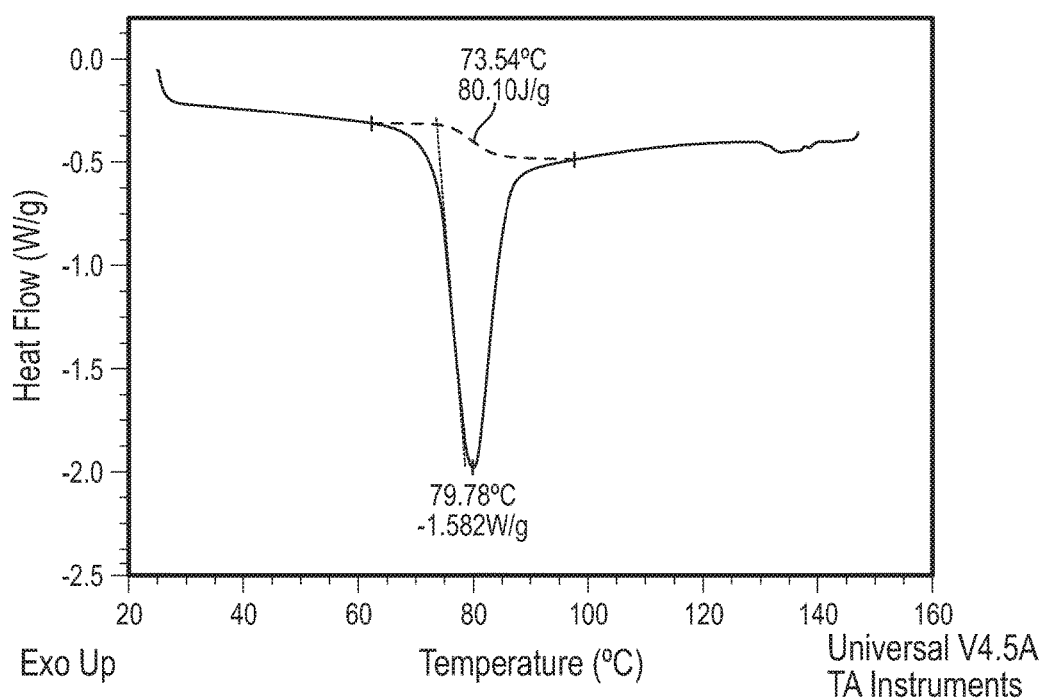
FIG. 5 shows a DSC thermogram of Compound 1 di-tosylate salt, Form HI.
Figure 6:
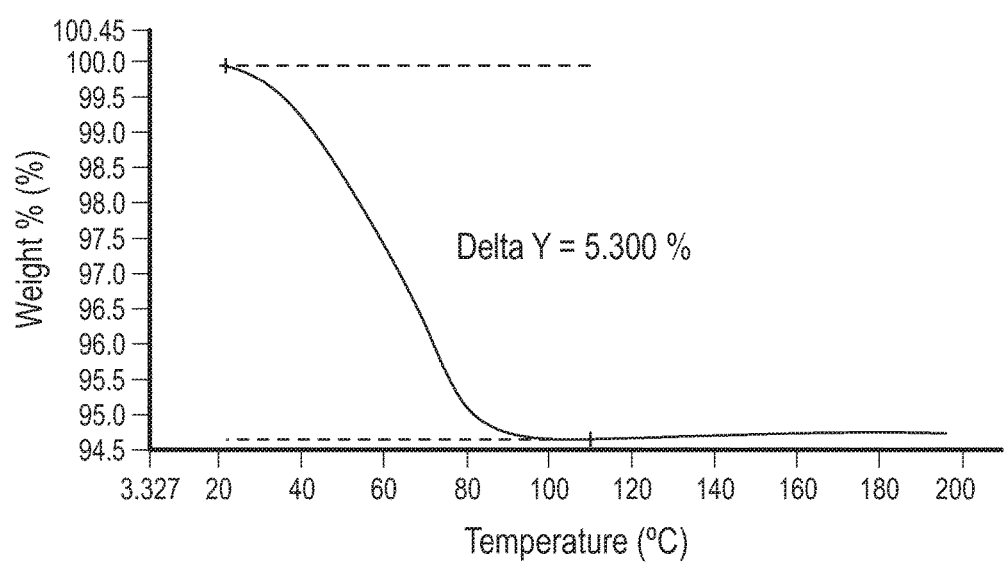
FIG. 6 shows a TGA thermogram of Compound 1 di-tosylate salt, Form HI.
Figure 7:
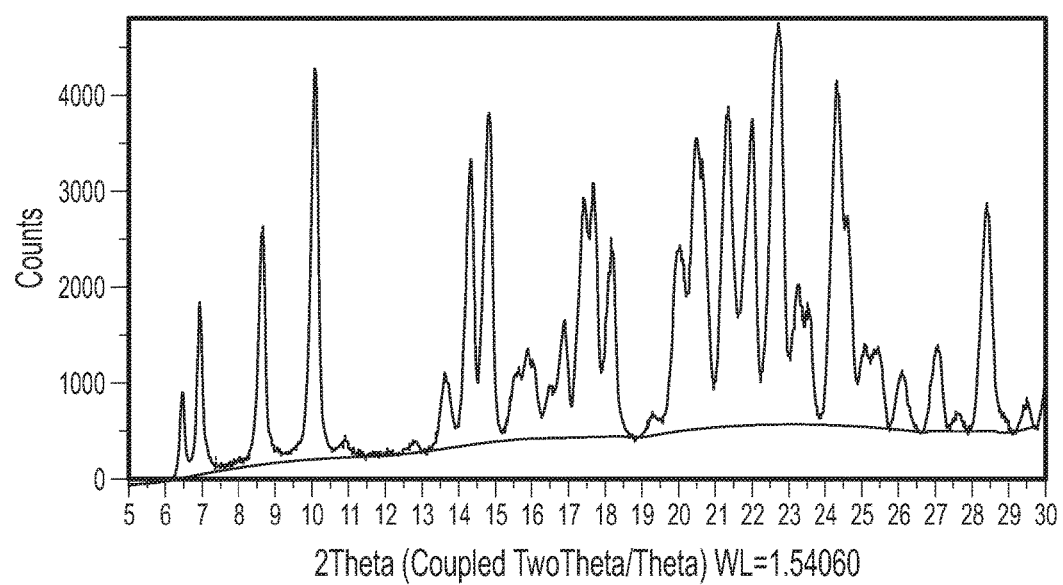
FIG. 7 shows an XRPD pattern of Compound 1 di-tosylate salt, Form HII.
Figure 8:
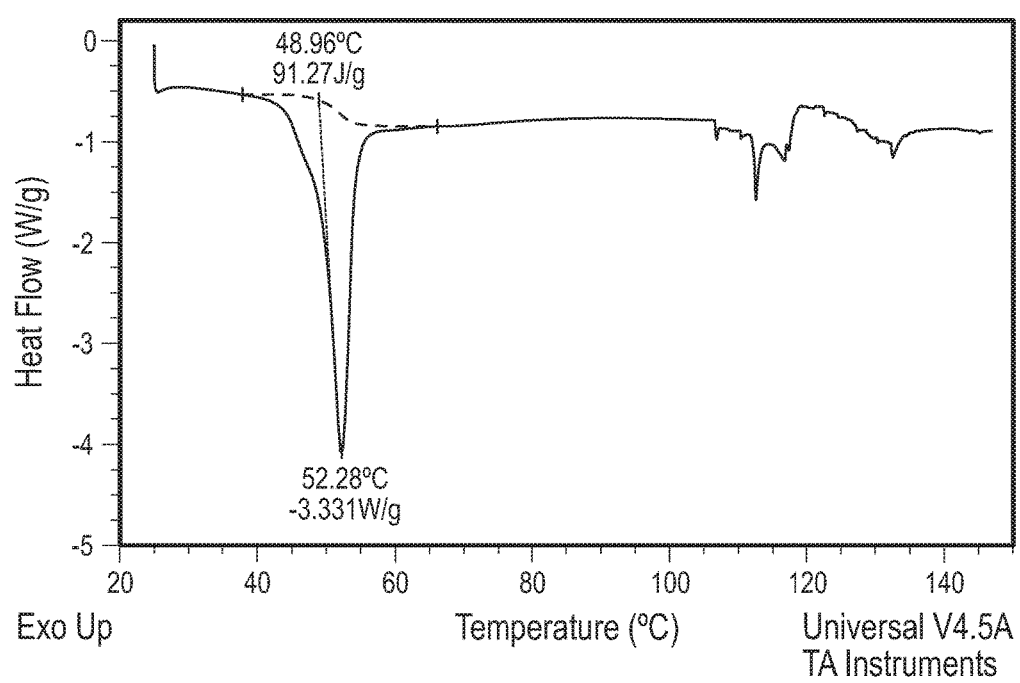
FIG. 8 shows a DSC thermogram of Compound 1 di-tosylate salt, Form HII.
Figure 9:
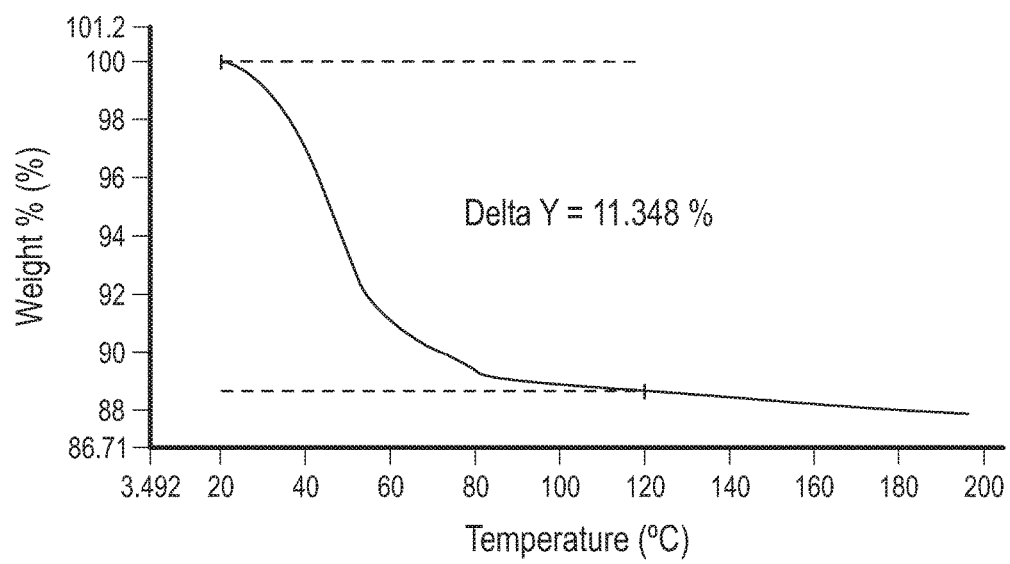
FIG. 9 shows a TGA thermogram of Compound 1 di-tosylate salt, Form HII.
Figure 10:
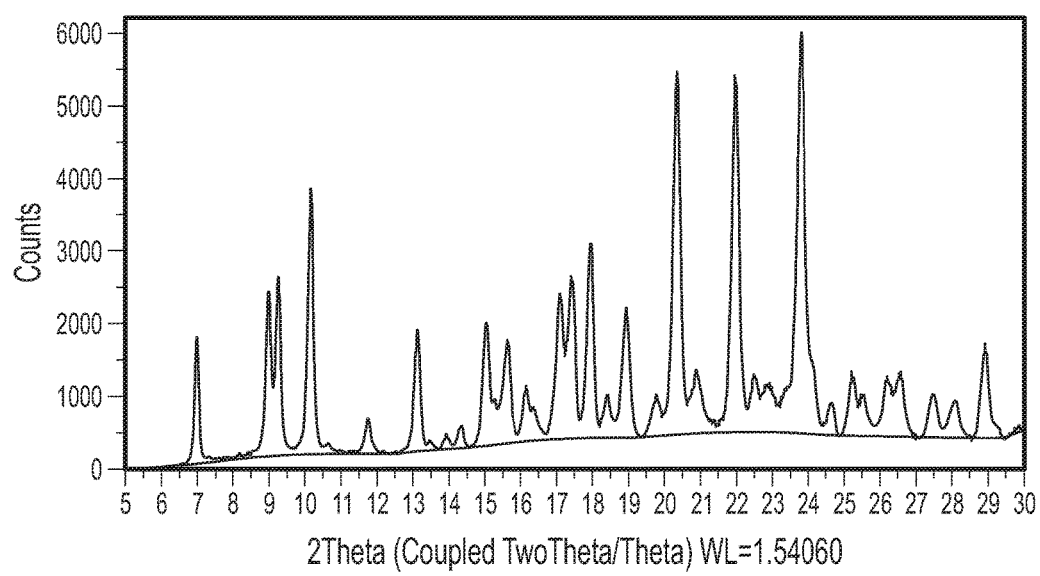
FIG. 10 shows an XRPD pattern of Compound 1 di-tosylate salt, Form HIII.
Figure 11:
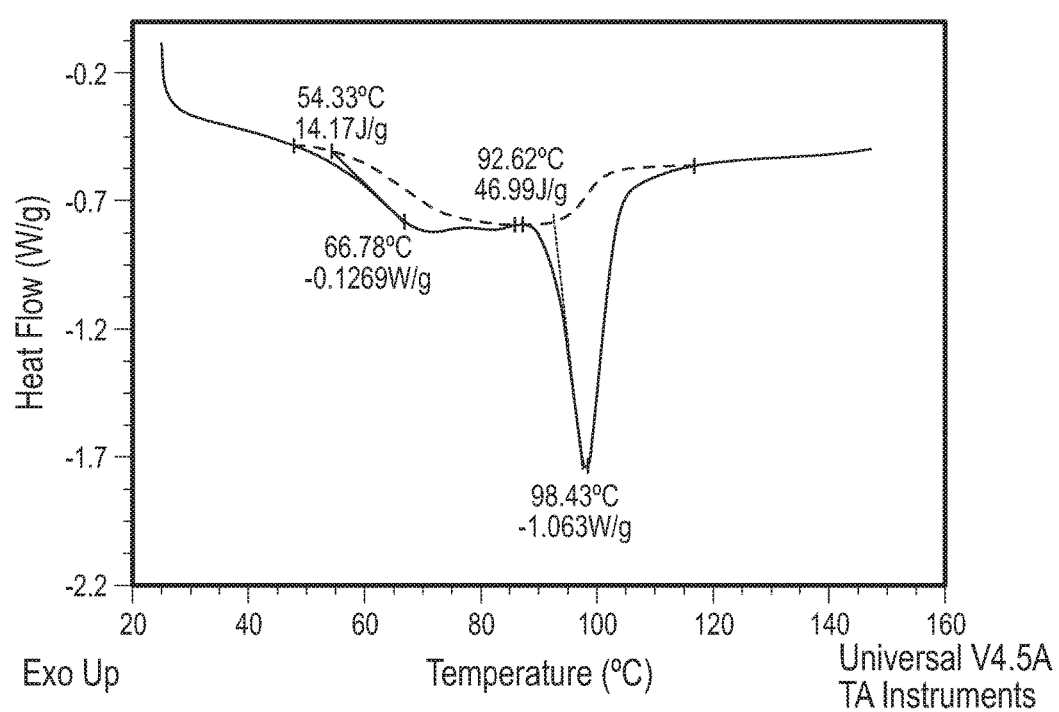
FIG. 11 shows a DSC thermogram of Compound 1 di-tosylate salt, Form HIII.
Figure 12:
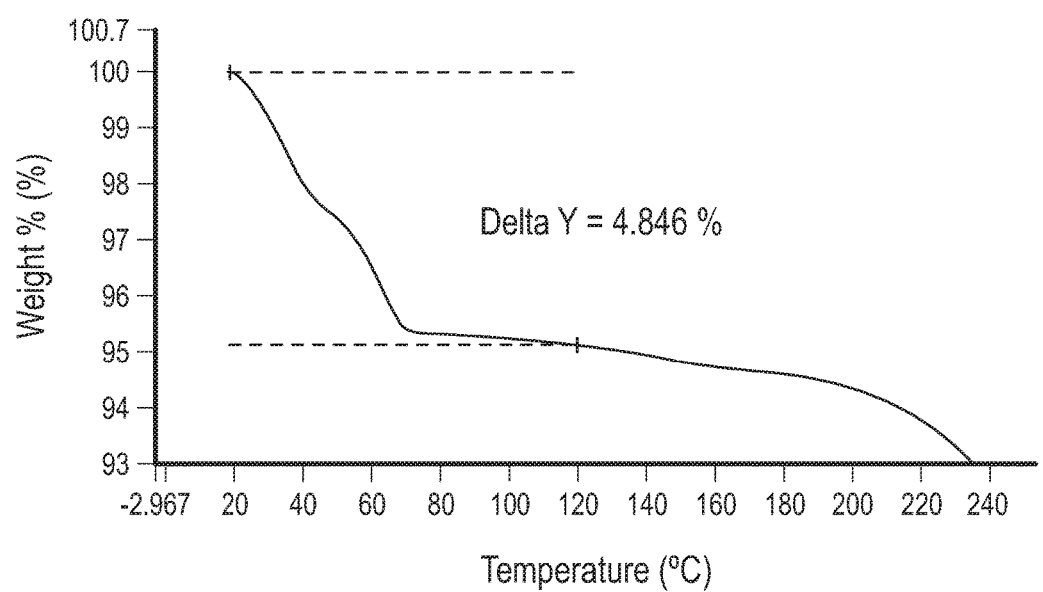
FIG. 12 shows a TGA thermogram of Compound 1 di-tosylate salt, Form HIII.
Figure 13:
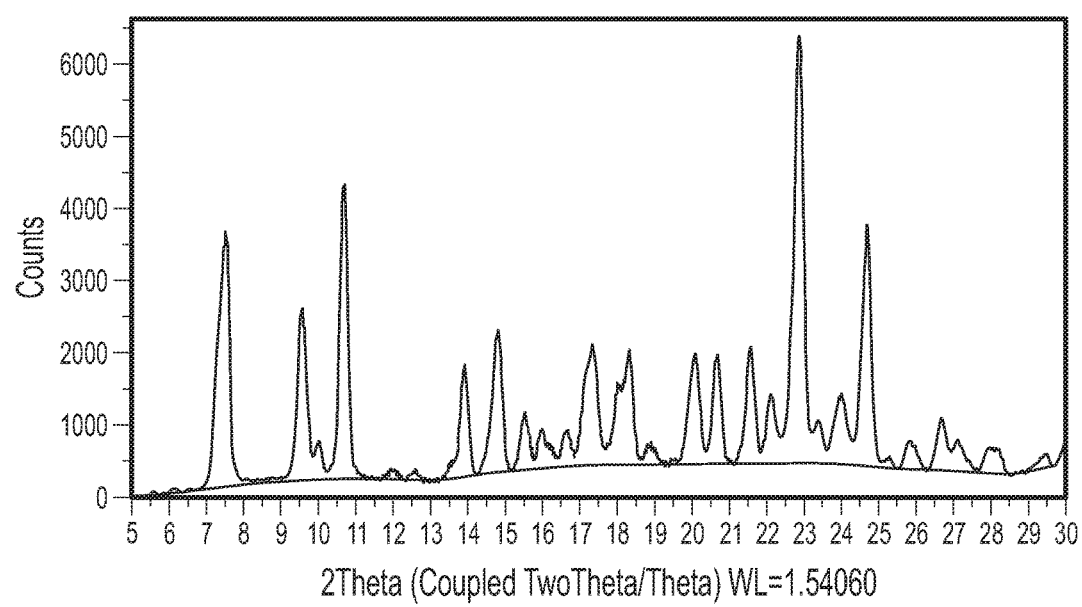
FIG. 13 shows an XRPD pattern of Compound 1 di-tosylate salt, Form DH.
Figure 14:
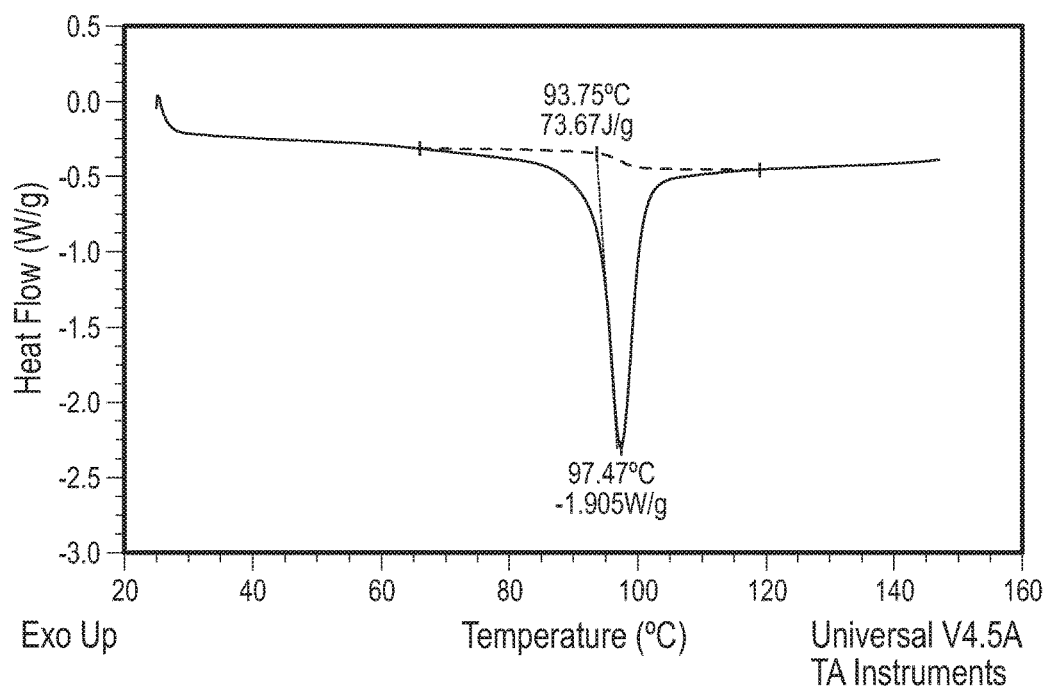
FIG. 14 shows a DSC thermogram of Compound 1 di-tosylate salt, Form DH.
Figure 15:
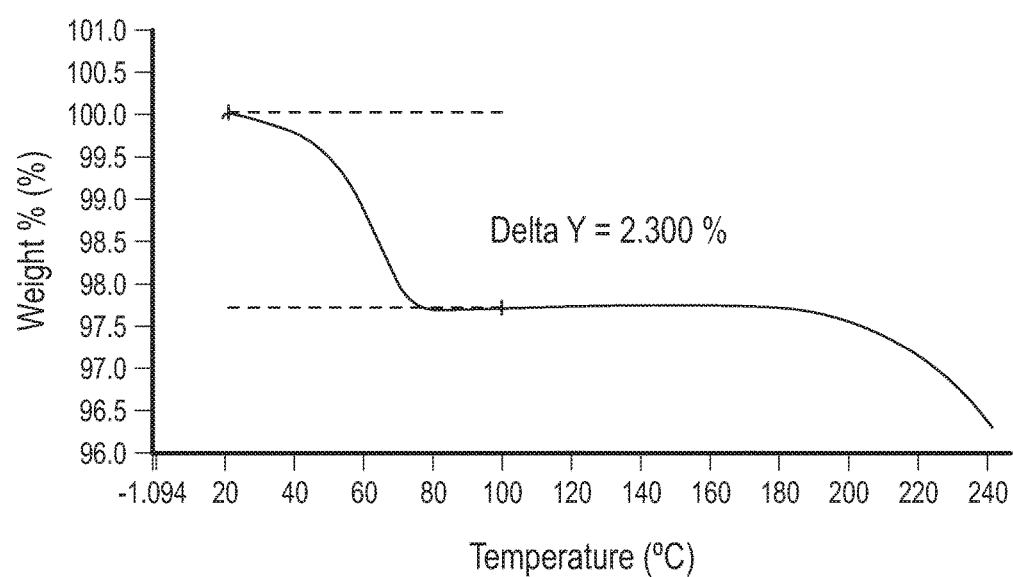
FIG. 15 shows a TGA thermogram of Compound 1 di-tosylate salt, Form DH.
Figure 16:
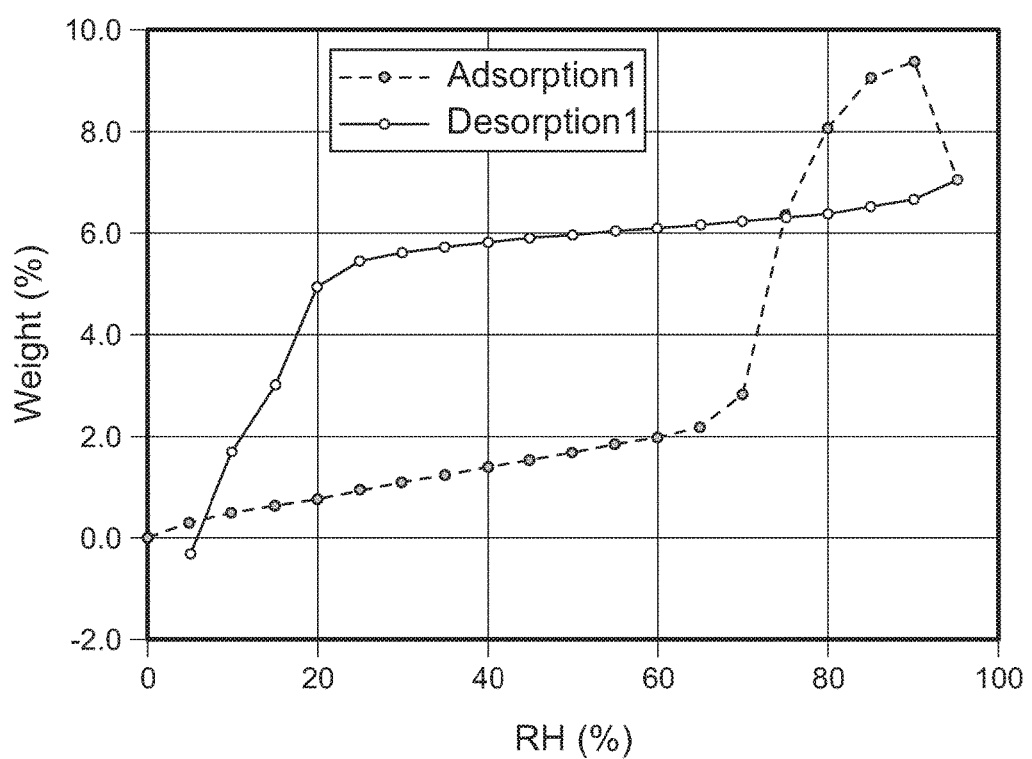
FIG. 16 shows a DVS adsorption-desorption isotherm of Compound 1 di-tosylate salt, Form I.
Figure 17:
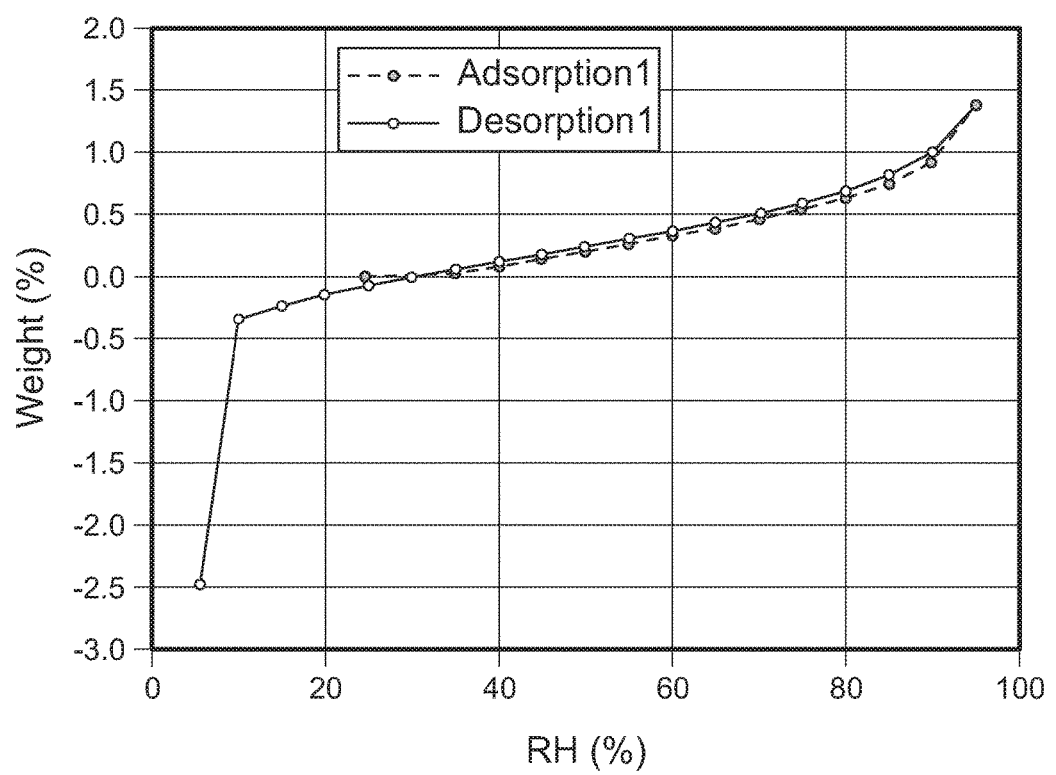
FIG. 17 shows a DVS adsorption-desorption isotherm of Compound 1 di-tosylate salt, Form HI.
Figure 18:
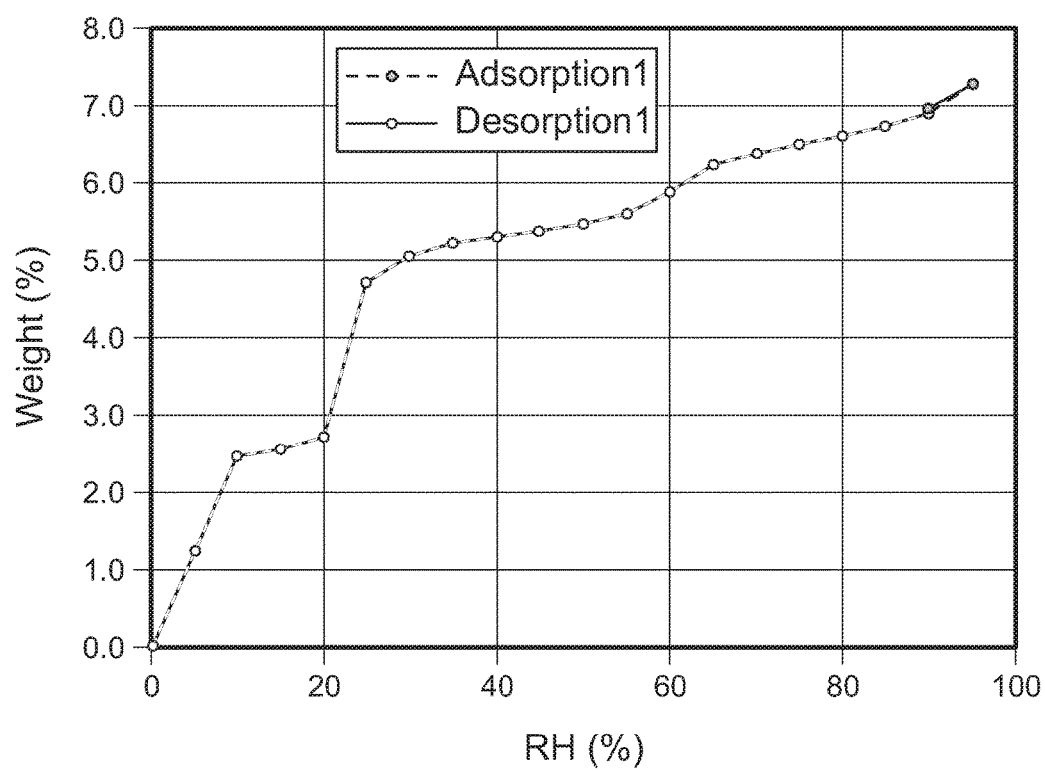
FIG. 18 shows a DVS adsorption-desorption isotherm of Compound 1 di-tosylate salt, Form DH.

The present invention relates to pharmaceutical compositions (or formulations) and dosage forms of Compound 1 di-tosylate salt or a hydrate or solvate having improved stability. In particular, the formulations and dosage forms of the present invention help increase the stability of Compound 1 di-tosylate salt under ambient conditions. Inclusion of an organic acid, such as fumaric acid, advantageously reduces degradation of Compound 1 di-tosylate salt. Additionally, use of a diluent, such as lactose (e.g., lactose monohydrate) can provide a further stabilizing advantage.

Formulations

The present invention provides, inter alia, a pharmaceutical formulation in solid oral dosage form comprising:

(a) an inhibitor of LSD1 which is Compound 1 di-tosylate salt, or a solvate or hydrate thereof, and (b) an organic acid.

Compound 1 refers to 1-{[4-(methoxymethyl)-4-({[(1R,2S)-2-phenylcyclopropyl]amino}methyl)piperidin-1-yl]methyl}cyclobutanecarboxylic acid having the formula:

Compound 1

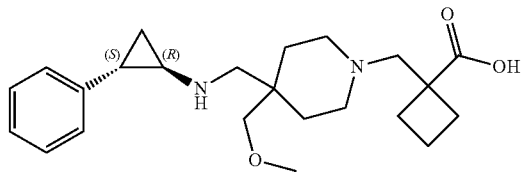

Compound 1 di-tosylate salt refers to 1-{[4-(methoxymethyl)-4-({[(1R,2S)-2-phenylcyclopropyl]amino}methyl)piperidin-1-yl]methyl}cyclobutanecarboxylic acid bis(4-methylbenzenesulfonate), which is shown below and is also referred to as "Compound 1 bis-p-toluenesulfonic acid," "Compound 1 bis-p-toluenesulfonic acid salt," "Compound 1 di-p-toluenesulfonic acid," "Compound 1 di-p-toluenesulfonic acid salt," "Compound 1 bis(4-methylbenzenesulfonate)," or 1-{[4-(methoxymethyl)-4-({[(1R,2S)-2-phenylcyclopropyl]amino}methyl)piperidin-1-yl]methyl}cyclobutanecarboxylic acid di-tosylate salt.

Compound 1 di-tosylate salt

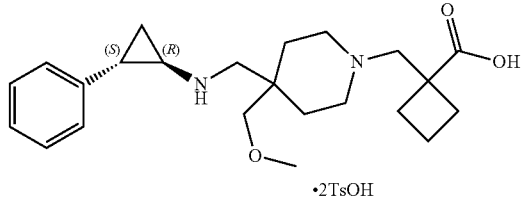

·2TsOH

Compound 1 can be prepared according to the procedures in US Publication No. 2015/0225401, which is incorporated by reference in its entirety. Compound 1 di-tosylate salt and various crystalline forms can be prepared according to the procedures in U.S. Provisional Application 62/204,105 and US Publication 2017/0044101, each of which is incorporated by reference in its entirety. See also e.g., Examples 6-7.

In some embodiments, Compound 1 di-tosylate salt used herein is in Form I. In other embodiments, Compound 1 di-tosylate salt is a hydrate, such as Form HI. Both Form I and Form HI are disclosed in US Patent Publication No. 2017/0044101. The term "hydrate," as used herein, is meant to refer to a solid form of Compound 1 di-tosylate salt that includes water. The water in a hydrate can be present in a stoichiometric amount with respect to the amount of salt in the solid, or can be present in varying amounts, such as can be found in connection with channel hydrates. In some embodiments, Compound 1 di-tosylate salt is a monohydrate (e.g., the molar ratio of the salt to water is about 1:1). In some embodiments, Compound 1 di-tosylate salt is a di-hydrate (e.g., the molar ratio of the salt to water is about 1:2). In some embodiments, Compound 1 di-tosylate salt is a hemi-hydrate (e.g., the molar ratio of the salt to water is about 2:1). In some embodiments, Compound 1 di-tosylate salt has one or more molecules of water per molecule of salt.

Compound 1 di-tosylate salt can also be in a solvated form. The term "solvate" means a solid form that includes solvent molecules with Compound 1 di-tosylate salt. The solvent can be an organic compound, an inorganic compound, or a mixture of both. Some examples of solvents include, methanol, ethanol, N,N-dimethylformamide, tetrahydrofuran, and dimethylsulfoxide. A solvate where the solvent is water is generally referred to as a "hydrate" or "hydrated form."

In some embodiments, the present invention provides a pharmaceutical formulation comprising:

(a) an inhibitor of LSD1 which is Compound 1 di-tosylate salt, or a solvate or hydrate thereof, (b) an organic acid, and (c) a diluent.

In certain embodiments, the pharmaceutical formulation provided herein includes Compound 1 di-tosylate salt, or a solvate or hydrate thereof, an organic acid, a diluent and a lubricant.

In some embodiments, the pharmaceutical formulation provided herein can further include a glidant, a binder, a disintegrant, or a combination thereof.

In some embodiments, the pharmaceutical formulation comprises about 0.5 wt % to about 25 wt % or about 1 wt % to about 10 wt % of Compound 1 di-tosylate salt. In some embodiments, the pharmaceutical formulation comprises about 1 wt % to about 10 wt % of Compound 1 di-tosylate salt. In some embodiments, the pharmaceutical formulation comprises about 1 wt % to about 5 wt % of Compound 1 di-tosylate salt. In some embodiments, the pharmaceutical formulation comprises about 2 wt % to about 4 wt % of Compound 1 di-tosylate salt. In some embodiments, the pharmaceutical formulation comprises about 1 wt %, about 2 wt %, about 2.5 wt %, about 3 wt %, about 3.5 wt %, about 4 wt %, about 4.5 wt %, or about 5 wt % of Compound 1 di-tosylate salt. In some embodiments, the pharmaceutical formulation comprises about 3 wt % of Compound 1 di-tosylate salt. In some embodiments, the pharmaceutical formulation includes about 2.5 wt % of Compound 1 di-tosylate salt.

Compound 1 di-tosylate salt, alone or together with pharmaceutical excipients, can degrade to form impurities. One impurity that may be formed is Compound 2, which is 14(4-(aminomethyl)-4-(methoxymethyl)piperidin-1-yl)methyl)cyclobutane-1-carboxylic acid and has the following structure:

Compound 2

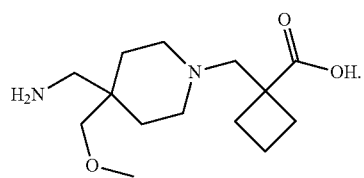

Another impurity that may be formed is Compound 3, which is phenylpropyl aldehyde having the following structure:

Compound 3

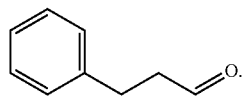

The formulations and dosage forms provided herein can have less than about 20%, less than about 15%, less than about 10%, less than about 5%, less than about 4%, less than about 3%, less than about 2%, less than about 1%, less than about 0.5%, or less than about 0.1% by weight of Compound 2. In some embodiments, the pharmaceutical formulations provided herein have less than about 2 wt % of Compound 2 as an impurity after exposure to about 25° C. and about 60% RH (relative humidity) for about 2 weeks. In some embodiments, the pharmaceutical formulation provided herein have less than about 25 wt %, less than about 20 wt %, less than about 10 wt %, less than about 5 wt %, less than about 1 wt %, or less than about 0.1 wt %, of Compound 2 as an impurity after exposure to about 40° C. and about 75% RH for about 2 weeks. In some embodiments, the pharmaceutical formulations provided herein have less than about 1 wt % of Compound 2 as an impurity after exposure to about 25° C. and about 60% RH (relative humidity) for about 1 month. In some embodiments, the pharmaceutical formulation provided herein have less than about 2 wt % or less than about 1 wt % of Compound 2 as an impurity after exposure to about 40° C. and about 75% RH for about 1 month.

The formulations of the invention include an organic acid which provides a stabilizing effect. In particular, the organic acid can inhibit the degradation of Compound 1 di-tosylate salt and prevent the formation of Compound 2 and other impurities. Exemplary organic acids include, but are not limited to, ascorbic acid, citric acid, fumaric acid, lactic acid, maleic acid, malic acid, sorbic acid, succinic acid, tartaric acid and hydrates or solvates thereof. The organic acid in the formulation can be from about 1% and to about 50%, about 1% to about 20%, about 1% to about 15%, about 5% to about 15%, about 8% to about 12%, about 9% to about 11% or about 10% by weight. For example, the organic acid in the formulation can be about 1, 2, 3, 4, 5, 6, 7, 8, 9, 10, 15, 20, 25, 30, 35, 40, 45 or 50% by weight. In some embodiments, the organic acid is fumaric acid or citric acid. In some embodiments, the organic acid is fumaric acid. In some embodiments, the organic acid is citric acid (e.g., citric acid monohydrate). While not wishing to be bound by theory, it is believed that the presence of an organic acid can create a localized pH within the pharmaceutical formulations and/or dosage form that reduces the rate of degradation.

In some embodiments, the pharmaceutical formulation comprises about 1 wt % to about 50 wt %, about 1 wt % to about 40 wt %, about 1 wt % to about 30 wt %, about 1 wt % to about 25 wt %, about 1 wt % to about 20 wt %, about 1 wt % to about 10 wt %, or about 1 wt % to about 5 wt % of fumaric acid. In some embodiments, the pharmaceutical formulation comprises about 1 wt % to about 50 wt % of fumaric acid. In some embodiments, the pharmaceutical formulation comprises about 1 wt % to about 20 wt % of fumaric acid. In some embodiments, the pharmaceutical formulation comprises about 1 wt % to about 15 wt % of fumaric acid. In some embodiments, the pharmaceutical formulation comprises about 5 wt % to about 15 wt % of fumaric acid. In some embodiments, the pharmaceutical formulation comprises about 8 wt % to about 12 wt % or about 9 wt % to about 11 wt % of fumaric acid. In some embodiments, the pharmaceutical formulation comprises about 9 wt % to about 11 wt % of fumaric acid. In some embodiments, the pharmaceutical formulation comprises about 1 wt %, 2 wt %, 3 wt %, 4 wt %, 5 wt %, about 6 wt %, about 7 wt %, about 8 wt %, about 9 wt %, about 10 wt %, about 11 wt %, about 12 wt %, about 13 wt %, about 14 wt %, about 15 wt %, about 20 wt %, about 25 wt %, about 30 wt %, about 35 wt %, about 40 wt %, about 45 wt %, or about 50 wt % of fumaric acid. In some embodiments, the pharmaceutical formulation comprises about 10 wt % of fumaric acid.

The diluent present in certain formulations of the invention helps prevent degradation of Compound 1 di-tosylate salt. Exemplary diluents include, but are not limited to, lactose, lactose monohydrate, spray-dried monohydrate lactose, lactose-316 Fast Flo®, mannitol, microcrystalline cellulose, acidified cellulose, starch 1500, prosolve MCC, and colloidal silica. In certain instances, the diluents include lactose, lactose monohydrate, spray-dried lactose monohydrate, lactose-316 Fast Flo®, mannitol and acidified cellulose. The diluent in the formulation can be from about 5% to about 97% by weight. For example, the diluent in the formulation can be about 5, about 10, about 15, about 20, about 25, about 30, about 35, about 40, about 45, about 50, about 55, about 60, about 65, about 70, about 75, about 80, about 85, about 90, about 95, about 96, or about 97% by weight. In some embodiments, the diluent is lactose or mannitol. In some embodiments, the diluent is lactose. In some embodiments, the lactose is lactose anhydrous or lactose monohydrate. The lactose monohydrate used herein can be amorphous, crystalline or a mixture thereof. In some embodiments, the diluent is spray-dried monohydrate lactose or lactose-316 Fast Flo®.

The pharmaceutical formulations provided herein can comprise about 5 wt % to about 97 wt %, about 70 wt % to about 97 wt % or about 75 wt % to about 97 wt % of lactose monohydrate. In some embodiments, the pharmaceutical formulation comprises about 80 wt % to about 97 wt % of lactose monohydrate. In some embodiments, the pharmaceutical formulation comprises about 85 wt % to about 97 wt % of lactose monohydrate. In some embodiments, the pharmaceutical formulation comprises about 86 wt % of lactose monohydrate. In some embodiments, the pharmaceutical formulation comprises about 96 wt % of lactose monohydrate. The pharmaceutical formulation provided herein can include about 5, about 10, about 15, about 20, about 25, about 30, about 35, about 40, about 45, about 50, about 55, about 60, about 65, about 70, about 75, about 80, about 85, about 90, about 95, about 96, or about 97% lactose monohydrate by weight.

Other diluents can be present in the formulations of the invention, for example, in an amount of 0 to about 85% by weight. In some embodiments, the formulation has about 50 to about 80%, about 55 to about 75%, or about 60 to about 70% by weight of filler. Non-limiting examples of other diluents include microcrystalline cellulose, starch 1500, and lactose anhydrous, or combinations thereof.

In some embodiments, the formulations of the invention include a lubricant. Lubricants can be present in the formulations and dosage forms of the invention in an amount of about 0 to about 10% by weight. Non-limiting examples of lubricants include magnesium stearate, stearic acid (stearin), hydrogenated oil, polyethylene glycol, sodium stearyl fumarate, and glyceryl behenate. In some embodiments, the lubricant is sodium stearyl fumarate or stearic acid. In some embodiments, the lubricant is sodium stearyl fumarate. In some embodiments, the lubricant is stearic acid.

The pharmaceutical formulation can comprise about 1 wt % to about 10 wt % of lubricant (e.g., sodium stearyl fumarate). In some embodiments, the pharmaceutical formulation comprises about 1 wt % to about 5 wt % of lubricant (e.g., sodium stearyl fumarate). In some embodiments, the pharmaceutical formulation comprises about 1 wt % to about 3 wt % of lubricant (e.g., sodium stearyl fumarate). In some embodiments, the pharmaceutical formulation comprises about 1 wt %, about 2 wt % about 3 wt %, about 4 wt %, or about 5 wt % of lubricant (e.g., sodium stearyl fumarate). In some embodiments, the pharmaceutical formulation comprises about 2 wt % of lubricant (e.g., sodium stearyl fumarate). In some embodiments, the pharmaceutical formulation comprises about 1 wt % to about 5 wt % of stearic acid. In other embodiments, the pharmaceutical formulation comprises about 2 wt % of stearic acid. In certain embodiments, the lubricant in the formulation can be from about 0.1% to about 3% by weight. For example, the lubricant can be about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.5% or about 3% by weight.

In some embodiments, the formulations of the invention include a glidant. Glidants can be present in the formulations and dosage forms of the invention in an amount of about 0 to about 5% by weight. Non-limiting examples of glidants include talc, colloidal silica (colloidal silicon dioxide), and cornstarch. In some embodiments, the glidant is colloidal silica.

In some embodiments, the formulations of the invention include a disintegrant. Disintegrants can be present in the dosage forms of the invention in an amount of about 0 to about 10% by weight. Non-limiting examples of disintegrants include croscarmellose sodium, crospovidone, starch, cellulose, and low substituted hydroxypropyl cellulose. In some embodiments, the disintegrant is croscarmellose sodium, sodium starch glycolate or crospovidone.

In certain situations, a binder can be used in the formulation. Exemplary binder includes polyvinyl pyrrolidone.

In some embodiments, film-coating agents can be present in an amount of 0 to about 5% by weight. Non-limiting illustrative examples of film-coating agents include hypromellose or polyvinyl alcohol based coating with titanium dioxide, talc and optionally colorants available in several commercially available complete coating systems.

In some embodiments, where for example the formulations and dosage forms of the invention are intended for sustained-release dosage forms, a sustained-release matrix former can be included. Example sustained-release matrix formers include cellulosic ethers such as hydroxypropyl methylcellulose (HPMC, hypromellose) which is a high viscosity polymer. The sustained-release dosage forms of the invention can include, for example, about 10 to about 30%, about 15 to about 25%, or about 18 to about 24% by weight of a sustained-release matrix former.

In some embodiments, provided herein is a pharmaceutical formulation comprising:
(a) about 1 wt % to about 5 wt % of Compound 1 di-tosylate salt, or a solvate or hydrate thereof; and
(b) about 1 wt % to about 15 wt % of fumaric acid.

In some embodiments, provided herein is a pharmaceutical formulation comprising:
(a) about 3 wt % of Compound 1 di-tosylate salt; and
(b) about 10 wt % to about 15 wt % of fumaric acid.

In some embodiments, provided herein is a pharmaceutical formulation comprising:
(a) Compound 1 di-tosylate salt, or a solvate or hydrate thereof;
(b) fumaric acid; and
(c) lactose or mannitol, or a solvate or hydrate thereof.

In some embodiments, provided herein is a pharmaceutical formulation comprising:
(a) Compound 1 di-tosylate salt, or a solvate or hydrate thereof;
(b) fumaric acid; and
(c) lactose, or a solvate or hydrate thereof.

In some embodiments, provided herein is a pharmaceutical formulation comprising:
(a) about 1 wt % to about 5 wt % of Compound 1 di-tosylate salt, or a solvate or hydrate thereof;
(b) about 1 wt % to about 15 wt % of fumaric acid; and
(c) about 80 wt % to about 97 wt % of lactose (e.g., monohydrate lactose).

In some embodiments, provided herein is a pharmaceutical formulation comprising:
(a) Compound 1 di-tosylate salt, or a solvate or hydrate thereof;
(b) fumaric acid;
(c) lactose, or a solvate or hydrate thereof; and
(d) a lubricant.

In some embodiments, provided herein is a pharmaceutical formulation comprising:
(a) about 1 wt % to about 5 wt % of Compound 1 di-tosylate salt, or a solvate or hydrate thereof;
(b) about 1 wt % to about 15 wt % of fumaric acid;
(c) about 80 wt % to about 97 wt % of monohydrate lactose; and
(d) about 1 wt % to about 5 wt % of a lubricant (e.g., sodium stearyl fumarate).

In some embodiments, provided herein is a pharmaceutical formulation comprising:
(a) about 1 wt % to about 5 wt % of Compound 1 di-tosylate salt, or a solvate or hydrate thereof;
(b) about 1 wt % to about 15 wt % of fumaric acid;
(c) about 80 wt % to about 97 wt % of monohydrate lactose; and
(d) about 1 wt % to about 5 wt % of stearic acid.

In some embodiments, provided herein is a pharmaceutical formulation comprising:
(a) about 3 wt % of Compound 1 di-tosylate salt;
(b) about 10 wt % to about 15 wt % of fumaric acid;
(c) about 86 wt % of monohydrate lactose; and
(d) about 2 wt % of a lubricant (e.g., sodium stearyl fumarate).

In some embodiments, provided herein is a pharmaceutical formulation comprising:
(a) about 3 wt % of Compound 1 di-tosylate salt;
(b) about 10 wt % to about 15 wt % of fumaric acid;
(c) about 86 wt % of monohydrate lactose; and
(d) about 2 wt % of a stearic acid.

The pharmaceutical formulations in solid dosage forms provided herein which are suitable for oral administration can be prepared by blending 1-{[4-(methoxymethyl)-4-({[(1R,2S)-2-phenylcyclopropyl]amino}methyl)piperidin-1-yl]methyl}cyclobutanecarboxylic acid di-tosylate salt with and an organic acid. The pharmaceutical formulation formed can be further compressed to form a tablet. In some embodiments, the organic acid is fumaric acid.

The pharmaceutical formulations in solid dosage form provided herein which are suitable for oral administration can be prepared by blending 1-{[4-(methoxymethyl)-4-({[(1R,2S)-2-phenylcyclopropyl]amino}methyl)piperidin-1-yl]methyl}cyclobutanecarboxylic acid di-tosylate salt with an organic acid and one or more portions of a diluent. The pharmaceutical formulation formed can be further compressed to form a tablet. In some embodiments, the organic acid is fumaric acid and the diluent is lactose monohydrate.

The pharmaceutical formulations in solid dosage form provided herein which are suitable for oral administration can be prepared by:

a) blending 1-{[4-(methoxymethyl)-4-({[(1R,2S)-2-phenylcyclopropyl]amino}methyl)piperidin-1-yl]methyl}cyclobutanecarboxylic acid di-tosylate salt with one or more portions of a diluent to form a first homogeneous mixture;

b) blending the first mixture with an organic acid to form a second homogeneous mixture; and c) blending the second mixture with a lubricant to form the pharmaceutical formulation. The pharmaceutical formulation formed can be further compressed to form a tablet. In some embodiments, the organic acid is fumaric acid, the diluent is lactose monohydrate and the lubricant is sodium stearyl fumarate or steric acid.

Provided is another method for preparing the pharmaceutical formulations described herein which are suitable for oral administration. The method includes:

a) blending 1-{[4-(methoxymethyl)-4-({[(1R,2S)-2-phenylcyclopropyl]amino}methyl)piperidin-1-yl]methyl}cyclobutanecarboxylic acid di-tosylate salt, an organic acid and one or more portions of a diluent to form a homogeneous mixture;

b) blending the homogenous mixture with a lubricant to form the pharmaceutical formulation.

The pharmaceutical formulation formed can be further compressed to form a tablet. In some embodiments, the organic acid is fumaric acid, the diluent is lactose monohydrate and the lubricant is sodium stearyl fumarate or steric acid.

Provided is another method for preparing the pharmaceutical formulations described herein which are suitable for oral administration. The method includes:

a) blending an organic acid and a diluent to form a first homogeneous mixture;

b) wet granulating the first mixture and drying to afford a dried mixture;

c) blending the dried mixture with 1-{[4-(methoxymethyl)-4-({[(1R,2S)-2-phenylcyclopropyl]amino}methyl)piperidin-1-yl]methyl}cyclobutanecarboxylic acid di-tosylate salt to form a second homogeneous mixture; and d) blending the second mixture with a lubricant to form the pharmaceutical formulation.

The pharmaceutical formulation formed can be further compressed to form a tablet. In some embodiments, the organic acid is fumaric acid, the diluent is lactose monohydrate and the lubricant is sodium stearyl fumarate or steric acid.

Compound 1 di-tosylate salt, diluent such as lactose monohydrate, organic acid such as fumaric acid or mixtures thereof can be prescreened to a uniformed particle size, for example, between 40 and 100 mesh prior to subject the each of the blending steps in the process of making the pharmaceutical formulations or tablets. In some embodiments, the particle size is 30, 40, 60, 70 or 80 mesh.

As used herein, the terms "blend," "bending," and "blended" refer to combining or mixing different substance to obtain a mixture. The resulting blended mixture can be homogeneous.

As used herein, the term "granulating" refers the process where the powder particles are made into larger granules. Wet granulation refers to when granules are formed by the addition of a granulation liquid such as water to the mixture.

In some embodiments, the Compound 1 di-tosylate salt, or hydrate or solvate thereof, is in crystalline form. Crystalline forms of Compound 1 di-tosylate salt (e.g., Form I) are disclosed in U.S. Provisional Application 62/204,105 and US Publication No. US 20170044101, the entireties of these are incorporated by reference. In some embodiments, the crystalline form comprises Form I. See also e.g., Examples 6-7.

In some embodiments, Form I has an X-ray powder diffraction pattern comprising one or more characteristic peaks selected from about 3.6, about 4.9, about 6.2, about 7.7 and about 22.7 degrees 2-theta. In some embodiments, Form I has an X-ray powder diffraction pattern further comprising one or more characteristic peaks selected from about 8.9, about 10.0, about 11.5, about 14.3, about 15.0, about 15.5, about 16.3, about 17.8, about 19.1, about 19.8, about 20.9, and about 22.2 degrees 2-theta, and combinations thereof.

In some embodiments, Form I has at least one characteristic XRPD peak, in terms of 2-theta, at about 3.6 degrees. In some embodiments, Form I has at least one characteristic XRPD peak, in terms of 2-theta, at about 4.9 degrees. In some embodiments, Form I has at least one characteristic XRPD peak, in terms of 2-theta, at about 6.2 degrees. In some embodiments, Form I has at least one characteristic XRPD peak, in terms of 2-theta, at about 7.7 degrees. In some embodiments, Form I has at least one characteristic XRPD peak, in terms of 2-theta, at about 22.7 degrees.

In some embodiments, Form I has at least one characteristic XRPD peak, in terms of 2-theta, at about 4.9 or about 6.2 degrees. In some embodiments, Form I has at least one characteristic XRPD peak, in terms of 2-theta, at about 3.6, about 4.9, or about 6.2 degrees.

In some embodiments, Form I has two or more characteristic XRPD peaks, in terms of 2-theta, selected from about 3.6, about 4.9, about 6.2, about 7.7 and about 22.7 degrees. In some embodiments, Form I has two or more characteristic XRPD peaks, in terms of 2-theta, selected from at about 3.6, about 4.9, about 6.2, about 7.7, about 22.7, about 8.9, about 10.0, about 11.5, about 14.3, about 15.0, about 15.5, about 16.3, about 17.8, about 19.1, about 19.8, about 20.9, and about 22.2 degrees.

In some embodiments, Form I has three or more characteristic XRPD peaks, in terms of 2-theta, selected from about 3.6, about 4.9, about 6.2, about 7.7, about 22.7, about 8.9, about 10.0, about 11.5, about 14.3, about 15.0, about 15.5, about 16.3, about 17.8, about 19.1, about 19.8, about 20.9, and about 22.2 degrees.

In some embodiments, Form I has four or more characteristic XRPD peaks, in terms of 2-theta, selected from about 3.6, about 4.9, about 6.2, about 7.7, about 22.7, about 8.9, about 10.0, about 11.5, about 14.3, about 15.0, about 15.5, about 16.3, about 17.8, about 19.1, about 19.8, about 20.9, and about 22.2 degrees.

In some embodiments, Form I has an X-ray powder diffraction pattern comprising one or more characteristic peaks selected from about 3.6, about 4.9, about 6.2, about 7.7, about 22.7, about 8.9, about 10.0, about 11.5, about 14.3, about 15.0, about 15.5, about 16.3, about 17.8, about 19.1, about 19.8, about 20.9, and about 22.2 degrees 2-theta, and combinations thereof.

In some embodiments, Form I exhibits a differential scanning calorimetry thermogram having an endothermic peak at a temperature of about 103° C. In some embodiments, Form I exhibits a differential scanning calorimetry thermogram having an endotherm with an onset temperature of about 95° C. and a peak temperature of about 103° C. In some embodiments, Form I exhibits a differential scanning calorimetry thermogram having an endotherm with an onset temperature of about 94.6° C. and a peak temperature of about 103.1° C. In some embodiments, Form I has an endothermic peak (e.g., a melting point) at a temperature of about 103° C. In some embodiments, Form I has an exothermic peak at a temperature about 187° C. In some embodiments, Form I has a melting point of about 103.1° C.

In some embodiments, Form I exhibits a DSC thermogram having an endotherm with an onset temperature of about 95° C., and a peak temperature of about 103° C.; and an X-ray powder diffraction pattern comprising one or more characteristic peaks at about 3.6, about 4.9, about 6.2, about 7.7, or about 22.7 degrees 2-theta.

In some embodiments, Form I exhibits a DSC thermogram having an endothermic peak at about 103° C.; and an X-ray powder diffraction pattern comprising one or more characteristic peaks at about 3.6, about 4.9, about 6.2, about 7.7, or about 22.7 degrees 2-theta.

In some embodiments, Form I exhibits a differential scanning calorimetry thermogram having an endotherm with an onset temperature of about 94.6° C. and a peak temperature of about 103.1° C.; and an X-ray powder diffraction pattern comprising a characteristic peak at about 3.6, about 4.9, about 6.2, about 7.7, or about 22.7 degrees 2-theta.

In some embodiments, Form I exhibits a DSC thermogram having an exothermic peak at about 187° C.; and an X-ray powder diffraction pattern comprising one or more characteristic peaks at about 3.6, about 4.9, about 6.2, about 7.7, or about 22.7 degrees 2-theta.

The XRPD analysis carried out on Form I was obtained from Rigaku MiniFlex X-ray Powder Diffractometer (XRPD). The general experimental procedures for XRPD were: (1) X-ray radiation from copper at 1.054056 Å with $K_\beta$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min. The XRPD data are provided in Table 1.

TABLE 1

| XRPD Data of Form I | | |
|---|---|---|
| 2-Theta (°) | Height | H % |
| 3.6 | 460 | 70 |
| 4.9 | 608 | 92.5 |
| 6.2 | 658 | 100 |
| 7.7 | 326 | 49.6 |
| 8.9 | 116 | 17.6 |
| 10.0 | 128 | 19.5 |
| 11.5 | 132 | 20.1 |
| 13.8 | 42 | 6.3 |

TABLE 1-continued

| XRPD Data of Form I | | |
|---|---|---|
| 2-Theta (°) | Height | H % |
| 14.3 | 51 | 7.8 |
| 15.0 | 98 | 14.9 |
| 15.5 | 105 | 15.9 |
| 16.3 | 123 | 18.7 |
| 17.1 | 49 | 7.4 |
| 17.8 | 170 | 25.8 |
| 19.1 | 163 | 24.8 |
| 19.8 | 108 | 16.4 |
| 20.9 | 202 | 30.8 |
| 22.2 | 170 | 25.9 |
| 22.7 | 408 | 62 |
| 23.1 | 133 | 20.3 |
| 23.9 | 49 | 7.5 |
| 24.4 | 94 | 14.3 |
| 24.9 | 73 | 11 |
| 25.8 | 65 | 9.9 |
| 27.2 | 55 | 8.4 |
| 28.7 | 43 | 6.5 |
| 29.1 | 53 | 8.1 |
| 30.6 | 47 | 7.1 |
| 31.2 | 70 | 10.6 |
| 32.8 | 59 | 9 |
| 38.4 | 39 | 5.9 |
| 39.6 | 35 | 5.4 |
| 43.9 | 36 | 5.5 |

The DSC of Form I was obtained from TA Instruments Differential Scanning calorimetry, Model Q200 with autosampler. The DSC instrument conditions were as follows: 30-300° C. at 10° C./min; $T_{zero}$ aluminum sample pan and lid; and nitrogen gas flow at 50 mL/min. The DSC thermogram revealed a major endothermal event at an onset temperature of 94.6° C. with a peak temperature of 103.1° C. which is believed to be the melting of the compound.

The TGA of Form I was obtained using a TA Instrument Thermogravimetric Analyzer, Model Q500. The general experimental conditions for TGA were: ramp from 20° C. to 600° C. at 20° C./min; nitrogen purge, gas flow at 40 mL/min followed by balance of the purge flow; sample purge flow at 60 mL/min; platinum sample pan. A weight loss of about 3.5% up to 150° C. was observed and believed to be associated with the loss of moisture and residual solvents. The compound started to decompose significantly after 200° C.

In some embodiments, the crystalline form comprises Form HI. Experimental evidence shows that Form HI is a hydrated form.

In some embodiments, Form HI has an XRPD pattern comprising a characteristic peak, in terms of 2-theta, at about 7.0 degrees. In some embodiments, Form HI has an XRPD pattern comprising a characteristic peak, in terms of 2-theta, at about 10.4 degrees. In some embodiments, Form HI has an XRPD pattern comprising a characteristic peak, in terms of 2-theta, at about 13.6 degrees. In some embodiments, Form HI has an XRPD pattern comprising a characteristic peak, in terms of 2-theta, at about 15.5 degrees. In some embodiments, Form HI has an XRPD pattern comprising a characteristic peak, in terms of 2-theta, at about 17.3 degrees. In some embodiments, Form HI has an XRPD pattern comprising a characteristic peak, in terms of 2-theta, at about 22.2 degrees. In some embodiments, Form HI has an XRPD pattern comprising a characteristic peak, in terms of 2-theta, at about 24.0 degrees.

In some embodiments, Form HI has an XRPD pattern comprising two or more characteristic peaks, in terms of 2-theta, selected from about 7.0, about 10.4, about 13.6, about 15.5, about 17.3, about 22.2, and about 24.0 degrees. In some embodiments, Form HI has an X-ray powder diffraction pattern comprising three or more characteristic peaks, in terms of 2-theta, selected from about 7.0, about 10.4, about 13.6, about 15.5, about 17.3, about 22.2, and about 24.0 degrees.

In some embodiments, Form HI has an XRPD pattern comprising one or more characteristic peaks, in terms of 2-theta, selected from about 7.0, about 10.4, about 13.6, about 15.5, about 16.6, about 17.3, about 18.7, about 19.8, about 20.2, about 20.5, about 20.8, about 21.7, about 22.2, about 23.1, about 24.0, and about 28.2 degrees.

In some embodiments, Form HI has an XRPD comprising two or more characteristic peaks, in terms of 2-theta, selected from about 7.0, about 10.4, about 13.6, about 15.5, about 16.6, about 17.3, about 18.7, about 19.8, about 20.2, about 20.5, about 20.8, about 21.7, about 22.2, about 23.1, about 24.0, and about 28.2 degrees.

In some embodiments, Form HI has an XRPD pattern comprising three or more characteristic peaks, in terms of 2-theta, selected from about 7.0, about 10.4, about 13.6, about 15.5, about 16.6, about 17.3, about 18.7, about 19.8, about 20.2, about 20.5, about 20.8, about 21.7, about 22.2, about 23.1, about 24.0, and about 28.2 degrees.

In some embodiments, Form HI has an XRPD pattern comprising four or more characteristic peaks, in terms of 2-theta, selected from about 7.0, about 10.4, about 13.6, about 15.5, about 16.6, about 17.3, about 18.7, about 19.8, about 20.2, about 20.5, about 20.8, about 21.7, about 22.2, about 23.1, about 24.0, and about 28.2 degrees.

In some embodiments, Form HI exhibits a differential scanning calorimetry thermogram having an endotherm with an onset temperature of about 74° C. and a peak temperature of about 80° C. In some embodiments, Form HI has an endothermic peak (e.g., a dehydration event) at a temperature of about 80° C.

In some embodiments, Form HI exhibits a differential scanning calorimetry thermogram having an endothermic peak at a temperature of about 80° C.; and an XRPD pattern comprising a characteristic peak selected from about 7.0, about 15.5, and about 17.3 degrees 2-theta. In some embodiments, Form HI exhibits a differential scanning calorimetry thermogram having an endotherm with an onset temperature of about 74° C. and a peak temperature of about 80° C.; and an XRPD pattern comprising a characteristic peak selected from about 7.0, about 15.5, and about 17.3 degrees 2-theta.

In some embodiments, Form HI exhibits a differential scanning calorimetry thermogram having an endothermic peak at a temperature of about 80° C.; and an XRPD pattern comprising a characteristic peak selected from about 7.0, about 10.4, about 13.6, about 15.5, about 17.3, about 22.2, and about 24.0 degrees. In some embodiments, Form HI exhibits a differential scanning calorimetry thermogram having an endotherm with an onset temperature of about 74° C. and a peak temperature of about 80° C.; and an XRPD pattern comprising a characteristic peak selected from about 7.0, about 10.4, about 13.6, about 15.5, about 17.3, about 22.2, and about 24.0 degrees.

Form HI of Compound 1 di-tosylate salt was prepared during the process of drying a wet sample of Compound 1 di-tosylate salt, Form I, under ambient conditions. Form I slowly absorbed atmospheric moisture and gradually changed to crystalline Form HI. Under storage conditions of 25° C./60% RH and 40° C./75% RH, Form I was also converted to Form HI.

The XRPD of Form HI was obtained from Bruker D2 PHASER X-ray Powder Diffractometer (XRPD) instrument. The general experimental procedures for XRPD were: (1) X-ray radiation from copper at 1.054056 Å with $K_\beta$ filter and LYNXEYE™ detector; (2) X-ray power at 30 KV, 10 mA; and (3) the sample powder was dispersed on a zero-background sample holder. The general measurement conditions for XRPD were: Start Angle 5 degrees; Stop Angle 30 degrees; Sampling 0.015 degrees; and Scan speed 2 degree/min. The XRPD data are provided in Table 2.

TABLE 2

XRPD Data of Form HI

| 2-Theta (°) | Height | H % |
|---|---|---|
| 7.0 | 4354 | 77.6 |
| 8.9 | 886 | 15.8 |
| 9.3 | 1185 | 21.1 |
| 10.4 | 3139 | 55.9 |
| 10.7 | 660 | 11.8 |
| 11.5 | 51 | 0.9 |
| 12.0 | 151 | 2.7 |
| 13.6 | 2036 | 36.3 |
| 14.1 | 491 | 8.7 |
| 14.4 | 124 | 2.2 |
| 15.5 | 4512 | 80.4 |
| 16.2 | 857 | 15.3 |
| 16.6 | 2374 | 42.3 |
| 17.3 | 4304 | 76.7 |
| 17.9 | 1242 | 22.1 |
| 18.7 | 2547 | 45.4 |
| 19.8 | 3854 | 68.7 |
| 20.2 | 3439 | 61.3 |
| 20.5 | 2144 | 38.2 |
| 20.8 | 4164 | 74.2 |
| 21.4 | 1389 | 24.8 |
| 21.7 | 2735 | 48.7 |
| 22.2 | 4344 | 77.4 |
| 23.1 | 2229 | 39.7 |
| 24.0 | 5611 | 100 |
| 24.7 | 126 | 2.2 |
| 25.3 | 786 | 14.0 |
| 25.5 | 1072 | 19.1 |
| 26.0 | 379 | 6.8 |
| 26.7 | 730 | 13.0 |
| 27.3 | 340 | 6.1 |
| 28.2 | 1649 | 29.4 |
| 28.8 | 246 | 4.4 |
| 29.2 | 144 | 2.6 |

The DSC of Form HI was obtained from TA Instruments Differential Scanning calorimetry, Model Q2000 with autosampler. The DSC instrument conditions were as follows: 25-150° C. at 10° C./min; $T_{zero}$ aluminum sample pan and lid; and nitrogen gas flow at 50 mL/min. The DSC thermogram revealed a major endothermal event at an onset temperature of 73.5° C. with a peak temperature of 79.8° C. which is believed to a dehydration event.

The TGA of Form HI was obtained using a PerkinElmer Thermogravimetric Analyzer, Model Pyris 1. The general experimental conditions for TGA were: ramp from 25° C. to 200° C. at 10° C./min; nitrogen purge gas flow at 60 mL/min; ceramic crucible sample holder. A weight loss of about 5.3% up to 110° C. was observed and believed to be associated mostly with the loss of water.

In some embodiments, the crystalline form comprises Form HII. Experimental evidence shows that Form HII is a hydrated form.

In some embodiments, Form HII has an XRPD pattern comprising a characteristic peak, in terms of 2-theta, at about 8.7 degrees. In some embodiments, Form HII has an XRPD pattern comprising a characteristic peak, in terms of 2-theta, at about 10.1 degrees. In some embodiments, Form HII has an XRPD pattern comprising a characteristic peak, in terms of 2-theta, at about 14.8 degrees. In some embodiments, Form HII has an XRPD pattern comprising a characteristic peak, in terms of 2-theta, at about 21.3 degrees. In some embodiments, Form HII has an XRPD pattern comprising a characteristic peak, in terms of 2-theta, at about 22.0 degrees. In some embodiments, Form HII has an XRPD pattern comprising a characteristic peak, in terms of 2-theta, at about 22.7 degrees. In some embodiments, Form HII has an XRPD pattern comprising a characteristic peak, in terms of 2-theta, at about 24.3 degrees.

In some embodiments, Form HII has an XRPD pattern comprising two or more characteristic peaks, in terms of 2-theta, selected from about 8.7, about 10.1, about 14.8, about 21.3, about 22.0, about 22.7, and about 24.3 degrees 2-theta.

In some embodiments, Form HII has an XRPD pattern comprising three or more characteristic peaks, in terms of 2-theta, selected from about 8.7, about 10.1, about 14.8, about 21.3, about 22.0, about 22.7, and about 24.3 degrees 2-theta.

In some embodiments, Form HII exhibits a differential scanning calorimetry thermogram having an endothermic peak at a temperature of about 52° C.

In some embodiments, Form HII exhibits a differential scanning calorimetry thermogram having an endothermic peak at a temperature of about 52° C.; and an X-ray powder diffraction pattern comprising a characteristic peak selected from about 8.7, about 10.1, about 14.8, about 21.3, about 22.0, about 22.7, and about 24.3 degrees 2-theta.

Form HII was prepared by slurring of Form I in water for 3 days at room temperature. The resulted suspension was filtered. The residual solid was collected and air dried for 5-7 days at ambient condition.

Form HII was characterized by XRPD. The XRPD was obtained from Bruker D2 PHASER X-ray Powder Diffractometer instrument. The general experimental procedures for XRPD are similar to those for Form HI. The XRPD data are provided in Table 3.

TABLE 3

XRPD Data of Form HII

| 2-Theta (°) | Height | H % |
| --- | --- | --- |
| 6.5 | 902 | 21.6 |
| 6.9 | 1739 | 43.0 |
| 8.0 | 74.7 | 1.8 |
| 8.7 | 2372 | 56.9 |
| 10.1 | 4023 | 96.5 |
| 10.9 | 212 | 5.1 |
| 12.8 | 103 | 2.5 |
| 13.7 | 717 | 17.2 |
| 14.3 | 2944 | 70.6 |
| 14.8 | 3399 | 81.5 |
| 15.5 | 699 | 16.8 |
| 15.6 | 662 | 15.9 |
| 15.9 | 873 | 20.9 |
| 16.0 | 808 | 19.4 |
| 16.5 | 526 | 12.6 |
| 16.9 | 1215 | 29.1 |
| 17.4 | 2487 | 59.6 |
| 17.7 | 2644 | 63.4 |
| 18.2 | 2023 | 48.5 |
| 19.3 | 195 | 4.7 |
| 20.0 | 1888 | 45.3 |
| 20.5 | 3037 | 72.8 |
| 20.6 | 2694 | 64.6 |
| 21.3 | 3226 | 77.4 |
| 22.1 | 2317 | 55.6 |
| 22.0 | 3129 | 75.0 |
| 22.7 | 4170 | 100 |

TABLE 3-continued

XRPD Data of Form HII

| 2-Theta (°) | Height | H % |
| --- | --- | --- |
| 23.2 | 1453 | 34.8 |
| 23.5 | 1263 | 30.3 |
| 24.3 | 3560 | 85.4 |
| 24.6 | 2153 | 51.6 |
| 25.1 | 804 | 19.3 |
| 25.4 | 792 | 19.0 |
| 26.1 | 594 | 14.2 |
| 27.1 | 817 | 19.6 |
| 27.6 | 184 | 4.4 |
| 28.4 | 2374 | 56.9 |
| 29.5 | 290 | 7.0 |

Form HII was characterized by DSC. The DSC was obtained from TA Instruments Differential Scanning calorimetry, Model Q2000 with autosampler. The DSC instrument conditions are similar to those for Form HI. The DSC thermogram revealed a major endothermal event at an onset temperature of 49.0° C. with a peak temperature of 52.3° C. which is believed to be the dehydration of the compound.

Form HII was characterized by TGA. The TGA was obtained from PerkinElmer Thermogravimetric Analyzer, Model Pyris 1. The general experimental conditions for TGA are similar to those for Form HI. A weight loss of about 11.3% up to 120° C. was observed and is believed to be associated mostly with the loss of water.

In some embodiments, the crystalline form comprises Form HIII. Experimental evidence shows that Form HIII is a hydrated form.

In some embodiments, Form HIII has an XRPD pattern comprising a characteristic peak, in terms of 2-theta, at about 7.0 degrees. In some embodiments, Form HIII has an XRPD pattern comprising a characteristic peak, in terms of 2-theta, at about 9.0 degrees. In some embodiments, Form HIII has an XRPD pattern comprising a characteristic peak, in terms of 2-theta, at about 9.2 degrees. In some embodiments, Form HIII has an XRPD pattern comprising a characteristic peak, in terms of 2-theta, at about 10.2 degrees. In some embodiments, Form HIII has an XRPD pattern comprising a characteristic peak, in terms of 2-theta, at about 17.9 degrees. In some embodiments, Form HIII has an XRPD pattern comprising a characteristic peak, in terms of 2-theta, at about 20.3 degrees. In some embodiments, Form HIII has an XRPD pattern comprising a characteristic peak, in terms of 2-theta, at about 22.0 degrees. In some embodiments, Form HIII has an XRPD pattern comprising a characteristic peak, in terms of 2-theta, at about 23.8 degrees.

In some embodiments, Form HIII has an XRPD pattern comprising two or more characteristic peaks, in terms of 2-theta, selected from about 7.0, about 9.0, about 9.2, about 10.2, about 17.9, about 20.3, about 22.0, and about 23.8 degrees.

In some embodiments, Form HIII has an XRPD pattern comprising three or more characteristic peaks, in terms of 2-theta, selected from about 7.0, about 9.0, about 9.2, about 10.2, about 17.9, about 20.3, about 22.0, and about 23.8 degrees 2-theta.

In some embodiments, Form HIII exhibits a differential scanning calorimetry thermogram having an endothermic peak at a temperature of about 67° C. In some embodiments, Form HIII further exhibits an endothermic peak at a temperature of about 98° C.

In some embodiments, Form HIII exhibits a differential scanning calorimetry thermogram having endothermic peaks at temperatures of about 67° C. and about 98° C.; and an X-ray powder diffraction pattern comprising a characteristic peak selected from about 7.0, about 9.0, about 9.2, about 10.2, about 17.9, about 20.3, about 22.0, and about 23.8 degrees 2-theta.

Form HIII was prepared by drying Form HI on Vapor Sorption Analyzer (TA Instruments VTI-SA+) at 40° C. with 0% RH N₂ for 3 h and then exposing it to humidity at about 30-50% RH at 25° C. for 1 day. Form HIII can change to Form HI when it is further exposed to high humidity at about 60-85% RH.

Form HIII was characterized by XRPD. The XRPD was obtained from Bruker D2 PHASER X-ray Powder Diffractometer (XRPD) instrument. The general experimental procedures for XRPD are similar to those for Form HI. The XRPD data are provided in Table 4.

TABLE 4

XRPD Data of Form HIII

| 2-Theta (°) | Height | H % |
| --- | --- | --- |
| 7.0 | 1719 | 31.2 |
| 8.6 | 86.6 | 1.6 |
| 9.0 | 2232 | 40.5 |
| 9.2 | 2435 | 44.1 |
| 10.2 | 3550 | 64.4 |
| 10.6 | 110 | 2.0 |
| 11.7 | 481 | 8.7 |
| 13.1 | 1671 | 30.3 |
| 13.5 | 99.6 | 1.8 |
| 13.9 | 150 | 2.7 |
| 14.3 | 269 | 4.9 |
| 15.0 | 1698 | 30.8 |
| 15.6 | 1398 | 25.3 |
| 16.2 | 742 | 13.4 |
| 16.3 | 443 | 8.0 |
| 17.1 | 1989 | 36.1 |
| 17.4 | 2147 | 38.9 |
| 17.9 | 2597 | 47.1 |
| 18.4 | 519 | 9.4 |
| 18.9 | 1756 | 31.8 |
| 19.8 | 475 | 8.6 |
| 20.3 | 4956 | 89.8 |
| 20.9 | 842 | 15.3 |
| 22.0 | 4791 | 86.9 |
| 22.5 | 736 | 13.3 |
| 22.9 | 635 | 11.5 |
| 23.4 | 603 | 10.9 |
| 23.5 | 826 | 15.0 |
| 23.8 | 5517 | 100 |
| 24.0 | 1063 | 19.3 |
| 24.6 | 453 | 8.2 |
| 25.2 | 849 | 15.4 |
| 25.5 | 580 | 10.5 |
| 26.2 | 778 | 14.1 |
| 26.5 | 854 | 15.5 |
| 27.5 | 603 | 10.9 |
| 28.1 | 515 | 9.3 |
| 28.9 | 2297 | 43.5 |
| 29.1 | 210 | 3.8 |
| 29.8 | 101 | 1.8 |

Form HIII was characterized by DSC. The DSC was obtained from TA Instruments Differential Scanning calorimetry, Model Q2000 with autosampler. The DSC instrument conditions are similar to those for Form HI. The DSC thermogram revealed two major endothermal events. The first event appeared at an onset temperature of 54.3° C. with a peak temperature of 66.8° C. which is believed to be the dehydration of the compound. The second event appeared at an onset temperature of 92.6° C. with a peak temperature of 98.4° C. which is believed to be the melting of the compound.

Form HIII was characterized by TGA. The TGA was obtained from PerkinElmer Thermogravimetric Analyzer, Model Pyris 1. The general experimental conditions for TGA are similar to those for Form HI. A weight loss of about 4.8% up to 120° C. was observed and is believed to be associated mostly with the loss of water.

In some embodiments, the crystalline form comprises Form DH.

In some embodiments, Form DH has an XRPD pattern comprising a characteristic peak, in terms of 2-theta, at about 7.5 degrees. In some embodiments, Form DH has an XRPD pattern comprising a characteristic peak, in terms of 2-theta, at about 9.6 degrees. In some embodiments, Form DH has an XRPD pattern comprising a characteristic peak, in terms of 2-theta, at about 10.7 degrees. In some embodiments, Form DH has an XRPD pattern comprising a characteristic peak, in terms of 2-theta, at about 14.8 degrees. In some embodiments, Form DH has an XRPD pattern comprising a characteristic peak, in terms of 2-theta, at about 20.1 degrees. In some embodiments, Form DH has an XRPD pattern comprising a characteristic peak, in terms of 2-theta, at about 20.7 degrees. In some embodiments, Form DH has an XRPD pattern comprising a characteristic peak, in terms of 2-theta, at about 21.6 degrees. In some embodiments, Form DH has an XRPD pattern comprising a characteristic peak, in terms of 2-theta, at about 22.9 degrees. In some embodiments, Form DH has an XRPD pattern comprising a characteristic peak, in terms of 2-theta, at about 24.7 degrees.

In some embodiments, Form DH has an XRPD pattern comprising two or more characteristic peaks, in terms of 2-theta, selected from about 7.5, about 9.6, about 10.7, about 14.8, about 20.1, about 20.7, about 21.6, about 22.9, and about 24.7 degrees 2-theta.

In some embodiments, Form DH has an XRPD pattern comprising three or more characteristic peaks, in terms of 2-theta, selected from about 7.5, about 9.6, about 10.7, about 14.8, about 20.1, about 20.7, about 21.6, about 22.9, and about 24.7 degrees 2-theta.

In some embodiments, Form DH exhibits a differential scanning calorimetry thermogram having an endothermic peak at a temperature of about 98° C.

In some embodiments, Form DH exhibits a differential scanning calorimetry thermogram having an endothermic peak at a temperature of about 98° C.; and an X-ray powder diffraction pattern comprising a characteristic peak selected from about 7.5, about 9.6, about 10.7, about 14.8, about 20.1, about 20.7, about 21.6, about 22.9, and about 24.7 degrees 2-theta.

Form DH was prepared by drying Form HI on Vapor Sorption Analyzer (TA Instruments VTI-SA+) at 25° C. with 0% RH N₂ for 2 days. When Form DH is exposed to humidity, it can absorb water and change to Form HIII at about 30-50% RH or to Form HI at high humidity around 60-85% RH.

Form DH was characterized by XRPD. The XRPD was obtained from Bruker D2 PHASER X-ray Powder Diffractometer (XRPD) instrument. The general experimental procedures for XRPD are similar to those for Form HI. The XRPD data are provided in Table 5.

TABLE 5

XRPD Data of Form DH

| 2-Theta (°) | Height | H % |
|---|---|---|
| 5.6 | 57.5 | 1.0 |
| 6.1 | 69.2 | 1.2 |
| 6.6 | 62.7 | 1.1 |
| 7.4 | 2956 | 50.0 |
| 7.5 | 3560 | 60.2 |
| 9.6 | 2326 | 39.4 |
| 10.0 | 534 | 9.0 |
| 10.7 | 4068 | 68.8 |
| 12.0 | 128 | 2.2 |
| 12.6 | 95.4 | 1.6 |
| 13.6 | 217 | 3.7 |
| 13.9 | 1487 | 25.2 |
| 14.8 | 1943 | 32.9 |
| 15.5 | 780 | 13.2 |
| 16.0 | 533 | 9.0 |
| 16.1 | 311 | 5.3 |
| 16.6 | 450 | 7.6 |
| 17.2 | 1437 | 24.3 |
| 17.3 | 1675 | 28.3 |
| 18.1 | 1061 | 18.0 |
| 18.3 | 1500 | 25.4 |
| 18.9 | 282 | 4.8 |
| 19.5 | 61.7 | 1.0 |
| 20.1 | 1482 | 25.1 |
| 20.7 | 1423 | 24.1 |
| 21.6 | 1585 | 26.8 |
| 22.1 | 936 | 15.8 |
| 22.9 | 5909 | 100 |
| 23.4 | 588 | 10.0 |
| 24.0 | 955 | 16.2 |
| 24.7 | 3283 | 55.6 |
| 25.3 | 94.8 | 1.6 |
| 25.8 | 754 | 12.7 |
| 26.7 | 721 | 12.2 |
| 27.1 | 433 | 7.3 |
| 28.0 | 335 | 5.7 |
| 28.2 | 322 | 5.4 |
| 29.5 | 200 | 3.4 |

Form DH was characterized by DSC. The DSC was obtained from TA Instruments Differential Scanning calorimetry, Model Q2000 with autosampler. The DSC instrument conditions similar to those for Form HI. The DSC thermogram revealed one major endothermal event at an onset temperature of 93.8° C. with a peak temperature of 97.5° C. which is believed to be the melting of the compound.

Form DH was characterized by TGA. The TGA was obtained from PerkinElmer Thermogravimetric Analyzer, Model Pyris 1. The general experimental conditions for TGA are similar to those for Form HI. A weight loss of about 2.3% up to 120° C. was observed and is believed to be associated mostly with the loss of water.

Form DH was characterized by DVS. The DVS analysis was performed on a TA Instruments Vapor Sorption Analyzer, model VTI-SA+. Form DH was generated by pre-drying Form HI on VTI at 40° C. with 0% RH $N_2$ for 3 h. Then the moisture uptake profile was completed in one cycle in 5% RH increments with adsorption from 0% RH to 95% RH followed by desorption in 5% increments from 95% to 85% RH. The equilibration criteria were 0.0010 wt % in 5 minutes with a maximum equilibration time of 180 minutes. All adsorption and desorption were performed at 25° C.

Form DH is hygroscopic and can absorb water stepwise to form different hydrates. The solid collected after DVS at 85% RH is characterized as Form HI.

The present application also relates to a solid dosage form comprising a pharmaceutical formulation provided herein.

In some embodiments, the solid dosage form is suitable for oral administration.

In some embodiments, the dosage form provided herein is in the form of tablets, capsules, pills, powders, sachets, and soft and hard gelatin capsules. In other embodiments, the dosage form provided herein is in the form of a capsule.

In some embodiments, the dosage form provided herein is in the form of a tablet or capsule. In some embodiments, the dosage form provided herein is in the form of a tablet.

In preparing a formulation, Compound 1 di-tosylate salt can be milled to provide the appropriate particle size prior to combining with the other ingredients. Compound 1 di-tosylate salt can be milled to a particle size of less than 200 mesh. The particle size can be adjusted by milling to provide a substantially uniform distribution in the formulation, e.g., about 40 mesh.

Compound 1 di-tosylate salt may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

The formulations of the invention can include additional excipients. Examples of suitable additional excipients include dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. Other excipients include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The present invention further provides a dosage form which comprises any of the above-described formulations of the invention. The term "dosage form" refers to a physically discrete unit suitable as unitary dosages for human subjects and other mammals, each unit containing a predetermined quantity of active material calculated to produce the desired therapeutic effect, in association with a suitable pharmaceutical excipient. In some embodiments, the dosage form is a solid dosage form, such as a tablet or capsule.

For preparing solid dosage forms such as tablets, Compound 1 di-tosylate salt can be mixed with excipients to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of Compound 1 di-tosylate salt.

The tablets or pills of provided herein can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compound 1 di-tosylate salt may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

As used herein, TsOH refers to p-toluenesulfonic acid, 4-methylbenzenesulfonic acid, or tosylic acid.

As used herein, and unless otherwise specified, the term "about," when used in connection with a numeric value or range of values which is provided to describe a particular salt or solid form, e.g., a specific temperature or temperature range, such as, for example, that describing a melting, dehydration, or glass transition; a mass change, such as, for example, a mass change as a function of temperature or humidity; a solvent or water content, in terms of, for example, mass or a percentage; or a peak position, such as, for example, in analysis by, for example, $^{13}C$ NMR, DSC, TGA and XRPD; indicate that the value or range of values may deviate to an extent deemed reasonable to one of ordinary skill in the art while still describing the particular solid form. Specifically, the term "about", when used in this context, indicates that the numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values while still describing the particular solid form. The term "about", when used in reference to a degree 2-theta value refers to +/−0.3 degrees 2-theta or +/−0.2 degrees 2-theta.

As used herein, the term "peak" or "characteristic peak" refers to a reflection having a relative height/intensity of at least about 3% of the maximum peak height/intensity. As used herein, the term "crystalline" or "crystalline form" refers to a crystalline solid form of a chemical compound, including, but not limited to, a single-component or multiple-component crystal form, e.g., including solvates, hydrates, clathrates, and co-crystals.

The term "crystalline form" is meant to refer to a certain lattice configuration of a crystalline substance. Different crystalline forms of the same substance typically have different crystalline lattices (e.g., unit cells), typically have different physical properties attributed to their different crystalline lattices, and in some instances, have different water or solvent content. The different crystalline lattices can be identified by solid state characterization methods such as by X-ray powder diffraction (XRPD). Other characterization methods such as differential scanning calorimetry (DSC), thermogravimetric analysis (TGA), dynamic vapor sorption (DVS), and the like further help identify crystalline form as well as help determine stability and solvent/water content.

Different crystalline forms of a particular substance, such as Compound 1 di-tosylate salt, can include both anhydrous forms of that substance and solvated/hydrated forms of that substance, where each of the anhydrous forms and solvated/hydrated forms are distinguished from each other by different XRPD patterns, or other solid state characterization methods, thereby signifying different crystalline lattices. In some instances, a single crystalline form (e.g., identified by a unique XRPD pattern) can have variable water or solvent content, where the lattice remains substantially unchanged (as does the XRPD pattern) despite the compositional variation with respect to water and/or solvent.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, filters used, the sample mounting procedure, and the particular instrument employed. In some instances, new peaks may be observed or existing peaks may disappear, depending on the type of the machine or the settings (for example, whether a Ni filter is used or not). As used herein, the term "peak" refers to a reflection having a relative height/intensity of at least about 3% or at least about 4% of the maximum peak height/intensity. Moreover, instrument variation and other factors can affect the 2-theta values. Thus, peak assignments, such as those reported herein, can vary by plus or minus about 0.2° (2-theta) or about 0.3° (2-theta), and the term "substantially" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc.

Crystalline forms of a substance can be obtained by a number of methods, as known in the art. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, exposure to moisture, grinding and solvent-drop grinding.

As used herein, the term "amorphous" or "amorphous form" is intended to mean that the substance, component, or product in question is not substantially crystalline as determined, for instance, by XRPD or where the substance, component, or product in question, for example is not birefringent when viewed microscopically. In certain embodiments, a sample comprising an amorphous form of a substance may be substantially free of other amorphous forms and/or crystalline forms. For example, an amorphous substance can be identified by an XRPD spectrum having an absence of reflections.

In some embodiments, Compound 1 di-tosylate salt (or hydrates and solvates thereof) of provided herein are prepared in batches referred to as batches, samples, or preparations. The batches, samples, or preparations can include Compound 1 di-tosylate salt in any of the crystalline or non-crystalline forms described herein, included hydrated and non-hydrated forms, and mixtures thereof.

As used herein, the term "crystalline purity," means percentage of a crystalline form in a preparation or sample which may contain other forms such as an amorphous form of the same compound, or at least one other crystalline form of the compound, or mixtures thereof.

As used herein, the term "substantially crystalline," means a majority of the weight of a sample or preparation of Compound 1 di-tosylate salt (or hydrate or solvate thereof) is crystalline and the remainder of the sample is a non-crystalline form (e.g., amorphous form) of Compound 1 di-tosylate salt. In some embodiments, a substantially crystalline sample has at least about 95% crystallinity (e.g., about 5% of the non-crystalline form of Compound 1 di-tosylate salt), preferably at least about 96% crystallinity (e.g., about 4% of the non-crystalline form of Compound 1 di-tosylate salt), more preferably at least about 97% crystallinity (e.g., about 3% of the non-crystalline form of Compound 1 di-tosylate salt), even more preferably at least about 98% crystallinity (e.g., about 2% of the non-crystalline form of Compound 1 di-tosylate salt), still more preferably at least about 99% crystallinity (e.g., about 1% of the non-crystalline form of Compound 1 di-tosylate salt), and most preferably about 100% crystallinity (e.g., about 0% of the non-crystalline form of Compound 1 di-tosylate salt). In some embodiments, the term "fully crystalline" means at least about 99% or about 100% crystallinity.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy*, 21st ed.; Lippincott Williams & Wilkins: Philadelphia, Pa., 2005; *Handbook of Pharmaceutical Excipients, 6th ed.*; Rowe et al., Eds.; The Pharmaceutical Press and the American Pharmaceutical Association: 2009; *Handbook of Pharmaceutical Additives, 3rd ed.*; Ash and Ash Eds.; Gower Publishing Company: 2007; *Pharmaceutical Preformulation and Formulation, 2nd ed.*; Gibson Ed.; CRC Press LLC: Boca Raton, Fla., 2009.

As used herein, the term "contacting" refers to the bringing together of indicated moieties in an in vitro system or an in vivo system. For example, "contacting" a LSD1 enzyme with a compound of the invention includes the administration of a compound of the present invention to an individual or patient, such as a human, having a LSD1 enzyme, as well as, for example, introducing a compound of the invention into a sample containing a cellular or purified preparation containing the LSD1 enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. The therapeutically effective amount will vary depending on the compound, the disease, disorder or condition and its severity and the age, weight, etc., of the mammal to be treated. In general, satisfactory results in subjects are indicated to be obtained at a daily dosage of from about 0.1 to about 10 g/kg subject body weight. In some embodiments, a daily dose ranges from about 0.10 to 10.0 mg/kg of body weight, from about 1.0 to 3.0 mg/kg of body weight, from about 3 to 10 mg/kg of body weight, from about 3 to 150 mg/kg of body weight, from about 3 to 100 mg/kg of body weight, from about 10 to 100 mg/kg of body weight, from about 10 to 150 mg/kg of body weight, or from about 150 to 1000 mg/kg of body weight. The dosage can be conveniently administered, e.g., in divided doses up to four times a day or in sustained-release form.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Methods of Use

The pharmaceutical formulations described herein can inhibit the activity of LSD1, thus, are useful in treating diseases and disorders associated with activity of LSD1. The present disclosure provides methods of treating an LSD1-associated or mediated disease or disorder in an individual (e.g., patient) by administering to the individual in need of such treatment a pharmaceutical formulation provided herein. The present disclosure also provides pharmaceutical formulation as described herein for use in treating an LSD1-associated or mediated disease or disorder. Also provided is the use of a pharmaceutical formulation as described herein in the manufacture of a medicament for treating an LSD1-associated or mediated disease or disorder.

In some embodiments, provided herein is a method of inhibiting LSD1, wherein said method comprising: contacting an LSD1 with a pharmaceutical formulation provided herein.

In some embodiments, provided herein is a dosage form (e.g., an oral dosage form such as tablets and capsules) comprising a pharmaceutical formulation provided herein that can inhibit the activity of LSD1 and thus, useful in treating diseases and disorders associated with activity of LSD1. The present disclosure provides methods of treating an LSD1-associated or mediated disease or disorder in an individual (e.g., patient) by administering to the individual in need of such treatment a dosage form (e.g., an oral dosage form such as tablets and capsules) comprising a pharmaceutical formulation provided herein. The present disclosure also provides a dosage form (e.g., an oral dosage form such as tablets and capsules) comprising a pharmaceutical formulation as described herein for use in treating an LSD1-associated or mediated disease or disorder. Also provided is the use of a dosage form (e.g., an oral dosage form such as tablets and capsules) comprising a pharmaceutical formulation as described herein in the manufacture of a medicament for treating an LSD1-associated or mediated disease or disorder.

In some embodiments, provided herein is a method of inhibiting LSD1, wherein said method comprising: contacting an LSD1 with a dosage form (e.g., an oral dosage form such as tablets and capsules) comprising a pharmaceutical formulation provided herein An LSD1-associated or mediated disease refers to any disease or condition in which LSD1 plays a role, or where the disease or condition is associated with expression or activity of LSD1. An LSD1-associated disease can include any disease, disorder or condition that is directly or indirectly linked to expression or activity of the LSD1, including over-expression and/or abnormal activity levels. Abnormal activity levels can be determined by comparing activity level in normal, healthy tissue or cells with activity level in diseased cells. An LSD1-associated disease can also include any disease, disorder or condition that can be prevented, ameliorated, inhibited or cured by modulating LSD1 activity. In some embodiments, the disease is characterized by the abnormal activity or expression (e.g., overexpression) of LSD1. In some embodiments, the disease is characterized by mutant LSD1. An LSD1 associated disease can also refer to any disease, disorder or condition wherein modulating the expression or activity of LSD1 is beneficial. The tosylate salts of the present disclosure can therefore be used to treat or lessen the severity of diseases and conditions where LSD1 is known to play a role.

Diseases and conditions treatable using the tosylate salts of the present disclosure include, generally cancers, inflammation, autoimmune diseases, viral induced pathogenesis, beta-globinopathies, and other diseases linked to LSD1 activity.

Cancers treatable using tosylate salts according to the present disclosure include, for example, hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), and multiple myeloma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angio sarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, moles dysplastic nevi, lipoma, angioma, dermatofibroma, and keloids.

The tosylate salts of the present disclosure can further be used to treat cancer types where LSD1 may be overexpressed including, for example, breast, prostate, head and neck, laryngeal, oral, and thyroid cancers (e.g., papillary thyroid carcinoma).

The tosylate salts of the present disclosure can further be used to treat genetic disorders such as Cowden syndrome and Bannayan-Zonana syndrome.

The tosylate salts of the present disclosure can further be used to treat viral diseases such as herpes simplex virus (HSV), varicella zoster virus (VZV), human cytomegalovirus, hepatitis B virus (HBV), and adenovirus.

The tosylate salts of the present disclosure can further be used to treat beta-globinopathies including, for example, beta-thalassemia and sickle cell anemia.

In some embodiments, the salts of the present disclosure may be useful in preventing or reducing the risk of developing the disease; e.g., preventing or reducing the risk of developing a disease, condition or disorder in an individual who may be predisposed to the disease, condition or disorder but does not yet experience or display the pathology or symptomatology of the disease.

EXAMPLES

Example 1. Excipient Compatibility

This study was performed to determine stability of Compound 1 di-tosylate salt, Form I, in combination with various oral solid dosage form excipients. Observed changes in impurity profile (by HPLC analysis) suggest chemical incompatibility. The data of the blends were compared with a control sample (Compound 1 di-tosylate salt alone) to assess the effect of each excipient relative to Compound 1 di-tosylate salt alone.

Blends were prepared by screening the components together; aliquots were then weighed for stability testing. The binary blend samples were initially stored under accelerated conditions (50° C./dry, 50° C./75% RH) in open glass vials and analyzed by HPLC to determine the potential for drug substance degradation with each excipient. Based on these results, additional binary and tertiary mixtures were prepared and stressed at 40° C./dry and 40° C./75% RH. Analysis of a control (Compound 1 di-tosylate salt alone) was included for comparison at each condition.

The following excipients (and their respective functions) were included in the study: microcrystalline cellulose (MCC)—diluent, lactose monohydrate—diluent, Prosolve (MCC/colloidal silica)—diluent, fumaric acid—pH modifier, citric acid—pH modifier, mannitol—diluent, pregelatinized starch (starch 1500)—diluent/disintegrant/binder, magnesium stearate—lubricant, sodium stearyl fumarate—lubricant, stearic acid—lubricant, colloidal silicon dioxide—glidant, polyvinyl pyrrolidone—binder, croscarmellose sodium—disintegrant, crospovidone—disintegrant, and sodium starch glycolate—disintegrant.

Materials are listed in Table 6. Compound 1 di-tosylate salt was blended at the desired ratio of excipient to drug (see Table 7 below) by weighing each material, mixing with a spatula in a vial, and screening the mixture 5 times with an 18 mesh screen. A control sample was included for comparison to the blends. The weight equivalent of approximately 4 mg of Compound 1 di-tosylate salt was added to each glass vial and initially set-up at 50° C./dry (<20% RH) and 50° C./75% RH. Based on results after 1 week at 50° C.; additional samples were set-up at 40° C./dry and 40° C./75% RH. The additional samples included tertiary mixtures with Compound 1 di-tosylate salt/lactose/fumaric acid or citric acid monohydrate. The lactose/fumaric acid combination was tested at multiple ratios of lactose to fumaric acid. The 75% RH chamber was maintained by using a saturated sodium chloride solution in water (inside a closed chamber). The humidity of the 75% RH chamber was verified with a hygrometer (VWR brand). Samples were tested by HPLC after 1 week at 50° C. and 1 and 2 weeks at 40° C. (low and high RH at both temperatures). Data were also measured for samples at 20° C. in closed vials.

TABLE 6

Materials

| Material | Supplier/Grade | Compend. |
|---|---|---|
| Lactose Monohydrate | Formost/316 | NF |
| Microcrystalline Cellulose | FMC/PH102 | NF |
| Starch 1500 | Colorcon | USP/NF |
| Prosolve | JRS-90 | USP/NF |
| Sodium Starch Glycolate | JRS | USP/NF |
| Croscarmellose Sodium | FMC/711 | NF |
| Polyvinyl Pyrrolidone | BASF | USP |

TABLE 6-continued

Materials

| Material | Supplier/Grade | Compend. |
|---|---|---|
| Crospovidone | ISP/XL | NF |
| Colloidal Silicon Dioxide | Cabot/M5P | USP/NF |
| Magnesium Stearate | Spectrum | NF |
| Sodium Stearyl Fumarate | JRS | NF |
| Stearic Acid | Spectrum | NF |
| Citric Acid Monohydrate | Spectrum | USP |
| Mannitol | Roquette 200 SD | USP |
| Fumaric Acid | Spectrum | NF |

TABLE 7

Weight Ratios

| Component | Cmpd 1 di-tosylate late salt to excipient | Cmpd 1 di-tosylate salt (g) | Excipient (g) | mg/vial |
|---|---|---|---|---|
| Cmpd 1 di-tosylate salt | alone as control | | | 4 |
| Lactose Monohydrate | 1 to 49 | 0.20 | 9.80 | 200 |
| Microcrystalline Cellulose | 1 to 49 | 0.20 | 9.80 | 200 |
| Starch 1500 | 1 to 49 | 0.20 | 9.80 | 200 |
| Prosolv MCC | 1 to 49 | 0.20 | 9.80 | 200 |
| Croscarmellose Sodium | 1 to 4 | 0.20 | 0.80 | 20 |
| Sodium Starch Glycolate | 1 to 4 | 0.20 | 0.80 | 20 |
| Polyvinyl Pyrrolidone | 1 to 4 | 0.20 | 0.80 | 20 |
| Crospovidone | 1 to 4 | 0.20 | 0.80 | 20 |
| Colloidal Silicon Dioxide | 1 to 1 | 0.30 | 0.30 | 8 |
| Magnesium Stearate | 1 to 1 | 0.30 | 0.30 | 8 |
| Sodium Stearyl Fumarate | 1 to 1 | 0.30 | 0.30 | 8 |
| Stearic Acid | 1 to 4 | * | * | * |
| Mannitol | 1 to 49 | 0.20 | 9.80 | 200 |
| Citric Acid Monohydrate | 1 to 49 | 0.20 | 9.80 | 200 |
| Fumaric Acid | 1 to 49 | 0.20 | 9.80 | 200 |
| Lactose/Fumaric acid 1:1 | 1 to 49 | 0.20 | 9.80 | 200 |
| Lactose/Citric acid 1:1 | 1 to 49 | 0.20 | 9.80 | 200 |
| Lactose/Fumaric Acid 3:1 | 1 to 49 | 0.20 | 9.80 | 200 |
| Lactose/Fumaric Acid 20:1 | 1 to 49 | 0.20 | 9.80 | 200 |

* Cmpd 1 di-tosylate salt/stearic acid added to each vial separately.

Samples were analyzed by HPLC using the method described below after dilution in 85% $H_2O$ (0.1% TFA)/15% acetonitrile to 4 mL, sonication for 5 minutes, and filtration (0.45 μm Acrodisc GHP). One injection per sample was performed at each stability station. Two methods were performed on the stability samples: a UV based HPLC method and a mass spectroscopy HPLC method performed for one impurity (Compound 2). Compound 2 refers to 1-((4-(aminomethyl)-4-(methoxymethyl)piperidin-1-yl)methyl)cyclobutane-1-carboxylic acid, which has the following structure:

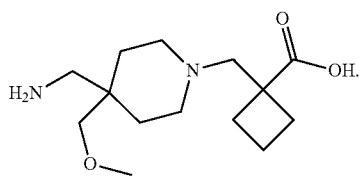

Compound 2

Compound 2 is believed to have been formed by cleavage at the amine-cyclopropyl linkage of Compound 1.

UV HPLC Method-Instrument: Agilent 1260 HPLC; Column: Ascentis Express C18 4.6×150 mm; Mobile Phase A: Water (0.1% TFA); Mobile Phase B: Acetonitrile (0.1% TFA); Flow Rate: 1.0 mL/min; Injection volume: 10 µL; UV Detection 214 nm; Column Temperature: 30° C.; Run Time: 33 min; Sample concentration: 1.0 mg/mL as salt; Threshold: 0.1%; Gradient Program:

| Time | % A | % B |
|---|---|---|
| 0 | 98 | 2 |
| 5 | 85 | 15 |
| 15 | 60 | 40 |
| 25 | 5 | 95 |
| 28 | 5 | 95 |
| 28.3 | 98 | 2 |
| 33 | 98 | 2 |

Compound 1 di-tosylate salt degradation (by peak area percent) is listed in Tables 8, 9, 10 and 11 as a function of excipient and storage condition. Accelerated storage (50° C., 40° C.) conditions were used to identify potential drug-excipient interactions. The drug substance used in this study had initial total impurity levels of approximately 0.3-0.4% by UV HPLC method analysis and approximately 0.3% Compound 2. Compound 2 can be determined by a mass spectroscopy HPLC method.

For all excipient blends, the levels of degradation (based on the UV HPLC method for impurities other than Compound 2) were greater than 1% after storage for 1 week at 50° C./dry (<20% RH). At 50° C./75% RH (Table 8), certain samples showed higher rates of degradation relative to low RH, while others were lower. Lactose and the control (Compound 1 di-tosylate salt alone) appeared to show lower rates at 50° C./75% RH versus 50° C./dry. For lactose, the level of degradation decreased from 1.4% at 50° C./dry to 0.1% at 50° C./75% RH. However, for Starch 1500, croscarmellose sodium, sodium starch glycolate, magnesium stearate and sodium stearyl fumarate samples at 50° C./75%, impurity levels increased relative to the 50° C./dry samples.

At 50° C./dry, the levels of Compound 2 were generally above 2% for both the various excipients blends and the control (Compound 1 di-tosylate salt alone). For most samples, Compound 2 levels increased at 75% RH relative to low RH. Based on the overall levels of degradation observed at 50° C., the study was expanded to include several additional excipients and the temperature was decreased to 40° C. The effect of excipient pH was investigated by including acidic excipients such as fumaric acid and citric acid. Also, tertiary blends were prepared with fumaric acid, lactose, and Compound 1 di-tosylate salt to determine if adding an acidic excipient can decrease the rate of degradation with lactose.

The results obtained for samples tested at 40° C./dry and 40° C./75% RH are listed in tables 10 (UV method) and 11 (% Compound 2 MS Method). These data for the UV HPLC method showed similar trends to the 50° C. data set where the control and the lactose blend showed better stability at higher RH versus dry storage. Many of the other excipients (i.e. Starch 1500, croscarmellose sodium, sodium starch glycolate, magnesium stearate, sodium stearyl fumarate, citric acid monohydrate) showed increased degradation at high RH. The magnesium stearate blend showed very high reaction rates at 40° C./75% RH by both analytical methods. The blends with acidic excipients (fumaric acid, citric acid) showed the lowest levels of degradation at dry RH. In addition, the tertiary blends with lactose/fumaric acid/and Compound 1 di-tosylate salt showed lower levels of degradation versus the blend with only lactose at dry RH. The tertiary blends also appear to show less effect of humidity at 40° C.

The results for percent of Compound 2 at 40° C./dry and 40° C./75% RH indicated that the levels of this impurity are significant when compared to results obtained from the UV HPLC method for other impurities. For Compound 1 di-tosylate salt alone, the levels of Compound 2 observed after 2 w at 40° C./dry and 2 w 40° C./75% RH were 3.4% and 1.9% respectively. While the blend with lactose showed higher levels than Compound 1 di-tosylate salt alone, the blends with fumaric acid and citric acid showed lower levels of Compound 2 at both high and low humidity. In addition, the tertiary blends with lactose/fumaric acid/Compound 1 di-tosylate salt showed significantly lower levels than with pure lactose. The inclusion of fumaric acid appeared to result in levels of Compound 2 similar to those observed with Compound 1 di-tosylate salt alone. After 2 weeks at 40° C./75% RH, the lactose/fumaric acid/Compound 1 di-tosylate salt tertiary blends showed 1.5-1.9% Compound 2 while Compound 1 di-tosylate salt alone showed 1.9%.

Based on these observations, the addition of fumaric acid to a lactose based formulation showed reduced degradation rates; levels as low as 5% fumaric acid show a significant benefit.

Data were also obtained after 2 w at 20° C. for both analytical methods. The levels of degradation are significantly lower when compared with the 40° C. data. Lactose showed lower levels of change when compared with other diluents (i.e. microcrystalline cellulose, starch 1500, Prosolv). As observed at 40° C., magnesium stearate resulted in higher levels of degradation when compared with other lubricants.

TABLE 8

Compound 1 di-tosylate salt degradation (UV Method) as a function of excipient at 50° C./dry, 50° C./75% RH.

| | Excipient compatibility | |
|---|---|---|
| | UV method | UV method |
| Component | 1 w 50° C. | 1 w 50° C./75% RH |
| Cmpd 1 di-tosylate salt alone | 1.4 | 0.3 |
| Lactose Monohydrate | 1.3 | 0.1 |
| Microcrystalline Cellulose | 3.0 | 2.6 |
| Starch 1500 | 1.5 | 6.0 |
| Prosolv MCC | 6.3 | 5.5 |
| Croscarmellose Sodium | 1.6 | >50% |
| Sodium Starch Glycolate | 1.6 | 3.6 |
| Magnesium Stearate | 1.4 | >50% |
| Sodium Stearyl Fumarate | 1.6 | 12 |

TABLE 9

Compound 1 di-tosylate salt degradation (% Compound 2) as a function of excipient at 50° C./dry, 50° C./75% RH.

| | Excipient Compatibility | |
|---|---|---|
| | % Compound 2 | % Compound 2 |
| Component | 1 w 50° C. | 1 w 50° C./75% RH |
| Cmpd 1 di-tosylate salt alone | 2.37 | 2.47 |
| Lactose Monohydrate | 2.58 | 3.45 |
| Microcrystalline Cellulose | 8.36 | 22.06 |
| Starch 1500 | 2.90 | 32.12 |
| Prosolv MCC | 6.35 | 20.40 |
| Croscarmellose Sodium | 3.29 | >50% |
| Sodium Starch Glycolate | 4.81 | 18.50 |
| Magnesium Stearate | 3.32 | NA |
| Sodium Stearyl Fumarate | 3.24 | 43.47 |

TABLE 10

Compound 1 di-tosylate salt degradation (UV Method) as a function of excipient at 40° C./dry, 40° C./75% RH

| Component | 1 W 40° C./dry | 2 W 40° C./dry | 1 W 40° C./75% RH | 2 W 40° C./75% RH |
|---|---|---|---|---|
| Cmpd 1 di-tosylate salt alone | 0.43 | 0.86 | <0.1 | <0.1 |
| Lactose Monohydrate | 0.60 | 1.1 | <0.1 | <0.1 |
| Microcrystalline Cellulose | 2.5 | 2.6 | 0.8 | 1.0 |
| Starch 1500 | 0.71 | 1.1 | 4.0 | 6.6 |
| Prosolv MCC | 2.76 | 4.4 | 1.6 | 2.4 |
| Croscarmellose Sodium | 0.63 | 1.0 | 4.8 | >>10% |
| Sodium Starch Glycolate | 2.0 | 3.8 | 6.7 | >>10% |
| Polyvinyl Pyrrolidone | 1.8 | 2.5 | 1.7 | 2.1 |
| Crospovidone | 1.0 | 1.3 | 0.39 | 1.1 |
| Colloidal Silicon Dioxide | 1.2 | 2.6 | 1.0 | 0.60 |
| Magnesium Stearate | 0.68 | 1.1 | >>10% | >>10% |
| Sodium Stearyl Fumarate | 0.49 | 0.93 | 1.1 | 3.7 |
| Stearic Acid | 0.19 | 0.41 | <0.1 | <0.1 |
| Mannitol | 0.81 | 0.74 | 0.63 | 1.4 |
| Citric Acid Monohydrate | <0.1 | <0.1 | 1.2 | 1.3 |
| Fumaric Acid | <0.1 | <0.1 | 0.14 | 0.30 |
| Lactose/Fumaric acid (50%) | <0.1 | <0.1 | <0.1 | <0.1 |
| Lactose/Citric Acid (50%) | <0.1 | <0.1 | 0.18 | 0.91 |
| Lactose/Fumaric acid (25%) | <0.1 | 0.16 | <0.1 | <0.1 |
| Lactose/Fumaric acid (5%) | 0.37 | 0.38 | <0.1 | <0.1 |

TABLE 11

Compound 1 di-tosylate salt degradation (% Compound 2) as a function of excipient at 40° C./dry, 40° C./75% RH.

| | wt % of Compound 2 | | | |
|---|---|---|---|---|
| Component | 40° C. 1 W | 40° C. 2 W | 40° C./75% RH 1 w | 40° C./75% RH 2 w |
| Cmpd 1 di-tosylate salt alone | 1.4 | 3.4 | 1.3 | 1.9 |
| Lactose Monohydrate | 3.1 | 5.6 | 1.4 | 3.3 |
| Microcrystalline Cellulose | 5.9 | 8.9 | 6.8 | 10.1 |
| Starch 1500 | 3.1 | 3.6 | 11.3 | 27.6 |
| Prosolv MCC | 5.3 | 8.2 | 8.0 | 14.5 |
| Croscarmellose Sodium | 2.9 | 5.0 | 32.2 | >50% |
| Sodium Starch Glycolate | 6.7 | 9.9 | 34.7 | >50% |
| Polyvinyl Pyrrolidone | 4.4 | 6.8 | 4.6 | 7.1 |
| Crospovidone | 2.3 | 3.5 | 2.8 | 7.9 |
| Colloidal Silicon Dioxide | 1.7 | 3.9 | 0.6 | 1.1 |
| Magnesium Stearate | 4.0 | 5.2 | >50% | >50% |
| Sodium Stearyl Fumarate | 1.8 | 3.2 | 7.5 | 14.4 |
| Stearic Acid | 1.2 | 2.2 | 1.7 | 3.0 |
| Mannitol | 1.3 | 3.4 | 1.1 | 2.0 |
| Citric Acid Monohydrate | 0.38 | 0.78 | 0.52 | 0.65 |
| Fumaric Acid | 0.67 | 0.89 | 0.73 | 0.92 |
| Lactose:Fumaric Acid (50% FA) | 0.77 | 0.85 | 1.2 | 1.5 |
| Lactose:Citric Acid 1:1 (50% CA) | 1.3 | 1.9 | 2.0 | 2.0 |
| Lactose:Fumaric Acid (25% FA) | 1.2 | 1.6 | 1.3 | 1.5 |
| Lactose:Fumaric Acid (5% FA) | 2.2 | 3.5 | 1.4 | 1.9 |

TABLE 12

Compound 1 di-tosylate salt compatibility at 20° C.

| Component | 20° C. 2 w UV method | 2 W 20° C. % of cmpd 2 |
|---|---|---|
| Cmpd 1 di-tosylate salt alone | <0.1 | 0.43 |
| Lactose Monohydrate | <0.1 | 0.63 |
| MCC | 0.43 | 1.1 |
| Starch 1500 | 0.52 | 0.86 |
| Prosolv MCC | 1.0 | 2.2 |
| Croscarmellose Sodium | 0.37 | 1.0 |
| Sodium Starch Glycolate | 1.5 | 4.7 |
| Polyvinyl Pyrrolidone | 0.62 | 1.5 |
| Crospovidone | 0.38 | 1.1 |
| Colloidal Silicon Dioxide | <0.1 | 0.55 |
| Magnesium Stearate | 0.67 | 1.9 |
| Sodium Stearyl Fumarate | <0.1 | 0.82 |
| Stearic Acid | <0.1 | 0.53 |
| Mannitol | 0.54 | 0.60 |
| Citric Acid Monohydrate | <0.1 | 0.48 |
| Fumaric Acid | <0.1 | 0.43 |

Compound 1 di-tosylate salt shows changes in impurity profile after storage at 40° C. (low and high RH) for both as Compound 1 di-tosylate salt alone and blends with common excipients, showing degradation with a broad range of excipients. Although Compound 1 di-tosylate salt alone was observed to be relatively stable at 40° C./75% (2 w) by the UV HPLC method, increased levels of Compound 2 were detected by the MS HPLC method.

At 40° C./75% RH, the primary degradation is related to formation of Compound 2. In addition, at 40° C./75% RH, Compound 1 di-tosylate salt alone is more stable than at 40° C./dry; this observation also held for Compound 1 di-tosylate salt blended with lactose monohydrate. The blend with lactose showed lower levels of change when compared with the other common diluents such as microcrystalline cellulose and starch 1500. At 40° C., the levels of impurities were lower in the presence of selected excipients, specifically fumaric acid. Tertiary mixtures with lactose/fumaric acid/Compound 1 di-tosylate salt were more stable than the binary blends with only lactose.

Example 2. Stability Study

The following study was performed to determine the chemical stability of 1 mg tablets of Compound 1 ditosylate, Form I, at various conditions of temperature and humidity. A direct compression process was used to prepare blends, which were then compressed at 1 mg dosage strength. The blends were composed of Compound 1 di-tosylate salt (API), lactose monohydrate (Fast Flo), with/without fumaric acid, and sodium stearyl fumarate. The tablets of the current study were packaged in HDPE bottles (induction sealed) and stored at 5° C., 25° C./60% RH, and 40° C./75% RH; analysis was performed by two HPLC methods (for UV detectable impurities and % Compound 2 with the MS based HPLC method). Tablet formulas are listed in Table 13 as % and mg/tablet.

TABLE 13

Composition for 1 mg Tablet Lots 1 and 2 (2.0 mg Compound 1 as salt is equivalent to 1.0 mg as free base)

|  | % composition | | mg/tablet | |
| --- | --- | --- | --- | --- |
|  | Lot 1 | Lot 2 | Lot 1 | Lot 2 |
| Compound 1 di-tosylate salt | 2.54 | 2.54 | 2.0 | 2.0 |
| Lactose Monohydrate Fast Flo NF | 95.5 | 85.5 | 76.4 | 68.4 |
| Fumaric Acid NF | 0.0 | 10.0 | 0.0 | 8.0 |
| Sodium Stearyl Fumarate NF | 2.0 | 2.0 | 1.6 | 1.6 |
|  | 100.0 | 100.0 | 80.0 | 80.0 |

Two lots of tablets were prepared. The procedures for preparing the 1 mg tablets are as follows:

| steps | Lot 1 | Lot 2 |
| --- | --- | --- |
| 1 | Screen API-60 mesh and weigh the API | Screen API-60 mesh and weigh API |
| 2 | Screen lactose 45 mesh and weigh lactose portion 1 (10% of formulation) | Process fumaric acid with Comill and weigh fumaric acid |
| 3 | Blend API with lactose manually and screen 60 mesh | Screen lactose 45 mesh and weigh portion 1 (10% of formulation) |
| 4 | Weigh screened lactose portion 2 (30% of formulation) | Blend API with lactose manually and screen 60 mesh |
| 5 | Blend the mixture from steps 1-4 for 5 min and screen 60 mesh | Weigh screened lactose portion 2 (30% of formulation) |
| 6 | Weigh screened lactose portion 3 (55.5% of formulation) and add to the mixture of step 5 | Blend the lactose of step 5 with the API/lactose mixture of step 4 for 5 min and screen 60 mesh |
| 7 | Blend the mixture of step 6 for 5 minutes | Weigh screened lactose portion 3 (45.5% of formulation) and add to the mixture of step 6 |
| 8 | Screen sodium stearyl fumarate and weigh sodium stearyl fumarate | Add fumaric acid to the mixture of step 7 and blend for 5 minutes |
| 9 | Blend sodium stearyl fumarate of step 8 with API/lactose mixture for 3 minutes | Screen sodium stearyl fumarate and weigh |
| 10 | Compress the mixture of step 9 with a 7/32 inch round tooling (80 mg target wt, 5 kp) | Blend sodium stearyl fumarate of step 9 with API/lactose/fumaric acid 3 minutes |
| 11 |  | Compress the mixture of step 10 with a 7/32 inch round tooling (80 mg target wt, 5 kp) |

API = Compound 1 di-tosylate salt

Blending was performed using a Turbula Blender and tablet compression was performed using a Globe Pharma Minipress with 7/32 inch round tooling. Excipient information is listed below:

| Material | Supplier/Grad | Compen |
| --- | --- | --- |
| Lactose Monohydrate | Formost/316 | NF |
| Fumaric Acid | Spectrum | NF |
| Sodium Stearyl Fumarate | JRS | NF |
| Compound 1 di-tosylate salt | INCYTE | NA |

The milling process for the fumaric acid for Lot 2 was performed with a Quadro Comill. The material was passed through screens 032R and 018R at 2500 RPM (one pass each screen size).

The dissolution data was obtained using USP Apparatus II: 50 RPM, water pH 2 as media, 500 mL volume, and at 37° C. The dissolution data of Lot 2 (with fumaric acid) is provide in the table below.

TABLE 14

Dissolution of Tablets with Fumaric Acid

| Time | % dissolved |
| --- | --- |
| 5 min | 68 |
| 15 min | 91 |
| 30 min | 98 |
| 45 min | 99 |

Tablets were packaged (25 tablets/bottle) in 40 cc HDPE bottles and induction sealed. The bottles were stored at 5° C., 25° C./60% RH and 40° C./75% RH.

Tablets were analyzed by HPLC using the method described below after dilution in 85% $H_2O$ (0.1% TFA)/15% acetonitrile (4 tablets in 20 mL), sonication for 10 minutes, and filtration (0.45 μm Acrodisc GHP). Two injections per sample were performed at each stability station. Two methods were performed on the stability samples: a UV based HPLC method (for assay, related substances) and a mass spectroscopy HPLC method performed for one impurity (Compound 2). Standards were prepared with API at the same theoretical concentration as the UV based HPLC method for assay determination.

UV HPLC Method—Instrument: Agilent 1260 HPLC Column: Ascentis Express C18 4.6×150 mm; Mobile Phase A: Water (0.1% TFA); Mobile Phase B: Acetonitrile (0.1% TFA); Flow Rate: 1.0 mL/min; Injection volume: 25 μL; UV Detection: 214 nm; Column Temperature: 30° C.; Run Time: 33 min; Threshold: 0.1%; Gradient Program:

| Time | % A | % B |
|------|-----|-----|
| 0 | 98 | 2 |
| 5 | 85 | 15 |
| 15 | 60 | 40 |
| 25 | 5 | 95 |
| 28 | 5 | 95 |
| 28.3 | 98 | 2 |
| 33 | 98 | 2 |

The 1 mg tablet stability (Table 15) is listed as a function of storage condition after 2 weeks. The drug substance batch used in this study had initial total impurity levels of approximately 0.3-0.4% by UV HPLC method analysis and approximately 0.3% Compound 2. Example 1 excipient compatibility studies for powder blends showed a significant protective effect of adding fumaric acid, both in binary mixtures with API and in tertiary mixtures with API/lactose monohydrate.

The stability of the 1 mg tablets showed a strong effect of storage temperature and the impact of fumaric acid. Lot 1 did not contain fumaric acid while Lot 2 contained 10% fumaric acid. After 2 weeks at 40° C./75% RH, the assay values were 42.9% and 77.5% for Lots 1 and 2 respectively. The percent of Compound 2 increased to over 50% for the Lot 1 (without fumaric acid), while Lot 2 showed 20% Compound 2 indicating the protective effect of fumaric acid. The UV detectable impurities showed a similar trend, with Lot 2 showing improved stability.

After 2 weeks at 25° C./60% RH, improved stability was also observed for Lot 2. The levels of Compound 2 for Lot 1 (without fumaric acid) were significantly greater (4.6%) when compared with Lot 2 (1.8%).

At 5° C. (2 weeks) both formulations appeared to be relatively stable with respect to chemical degradation in terms of assay, UV detectable impurities, and percent of Compound 2.

TABLE 15

1 mg Tablet Stability in HDPE Bottles

|  | Assay (% label) | | Impurities: UV | | Compound 2 (%) | |
|---|---|---|---|---|---|---|
|  | Lot 1 | Lot 2 | Lot 1 | Lot 2 | Lot 1 | Lot 2 |
| Initial | 98.2 | 96.9 | 0.34 | 0.33 | 0.46 | 0.29 |
| 5° C. | 98.4 | 96.3 | 0.36 | 0.32 | 0.38 | 0.36 |
| 25° C./60% RH | 90.9 | 95.8 | 0.92 | 0.64 | 4.6 | 1.8 |
| 40° C./75% RH | 42.9 | 77.5 | 25 | 5.5 | >50% | 20 |

Lot 1 (without Fumaric Acid),
Lot 2 (with 10% Fumaric Acid)

Compound 1 di-tosylate salt tablets (1 mg free base dosage strength) were compressed from lactose monohydrate based formulations with and without fumaric acid. Example 1 excipient compatibility studies had shown that API blends containing lactose and fumaric acid were more stable than blends with only lactose. Two tablet formulations were compressed with the compositions listed in Table 13 and packaged in 40 cc HDPE bottles. Both formulations contained lactose monohydrate as a diluent and sodium stearyl fumarate as a lubricant. Lot 2, which contained 10% fumaric acid, showed significantly lower rates of degradation after 2 weeks at both 25° C./60% RH and 40° C./75% RH indicating an advantage of having fumaric acid in the formulation.

Example 3. Tablet Prepared with Form HI of Compound 1 Di-Tosylate Salt

Tablets of Form HI of Compound 1 di-tosylate salt were prepared with the following compositions.

TABLE 16

Composition for 1 mg Tablet

|  | % comp. | mg/tablet |
|---|---|---|
| Compound 1 di-tosylate salt | 2.58 | 2.0 |
| Lactose Monohydrate Fast Flo NF | 85.46 | 68.4 |
| Fumaric Acid NF | 10.0 | 8.0 |
| Sodium Stearyl Fumarate NF | 2.0 | 1.6 |
|  | 100.0 | 80.0 |

(2.0 mg Compound 1 as salt is equivalent to 1.0 mg as free base)

The procedures to prepare the tablets are as follows.

| Steps | |
|---|---|
| 1 | Screen API-80 mesh and weigh |
| 2 | Process fumaric acid with Comill and weigh. |
| 3 | Mix lactose portion 1 (10% of formulation) with API and fumaric acid. Screen 60 mesh and blend the mixture for 5 mins |
| 4 | Weigh screened lactose portion 2 (30% of formulation) and blend with the mixture of step 3 for 5 mills and screen 60 mesh |
| 5 | Weigh screened lactose portion 3 (45.5% of formulation) and add to the mixture of step 4. Blend the resulting mixture for 5 mins |
| 6 | Screen sodium stearyl fumarate and weigh |
| 7 | Blend the screened sodium stearyl fumarate with API/lactose/fumaric acid mixture of step 5 for 3 minutes |
| 8 | Compress the mixture of step 7 with a 7/32 inch round tooling (80 mg target wt, 5 kp) |

A study of the stability of the tablet was carried out using similar procedures as in Example 2 and the results are as follows.

TABLE 17

Tablet Stability 1 month at 5° C., 25° C./60% RH

|  | Condition: | | | | |
|---|---|---|---|---|---|
| Test | Initial | 5° C. | | 25° C./60% RH | | 40° C./75% RH |
|  |  | 1 m | 3 m | 1 m | 3 m | 1 m |
| Assay | 100.1 | 100.6 | 101.8 | 98.9 | 95.7 | 90.7 |
| UV Impurities (%) | <0.05 | <0.05 | <0.05 | <0.05 | 0.08 | 0.39 |
| Compound 2 (%) | 0.07 | 0.10 | 0.19 | 0.59 | 0.65 | 1.5 |

Example 4. Wet Granulation Process Using Form HI of Compound 1 Di-Tosylate Salt

Tablets described herein can also be prepared according to the wet granulation process below. The wet granulation was performed in a high shear granulator with an impeller blade and chopper blade rotating as water is added. The amount of water was controlled to prevent overwetting. The wet granules can be dried in a static oven or fluid bed dryer. The process was performed to create a well distributed mixture of lactose monohydrate and fumaric acid. Table 19 below shows the tablet compositions prepared using the wet granulation process. Stability data for formulation A prepared according to the process below (wet granulation process) and a composition similar to that of the tablet in Table 16 are listed in Table 18. Reduced levels of Compound 2 were observed after 1 month of storage for a tablet prepared using the wet granulation process. Stability data for formulation B prepared according to the process below is shown in Table 20.

| Steps | |
|---|---|
| 1 | Screen API-60 or 80 mesh and weigh |
| 2 | Screen fumaric acid and lactose (40 mesh), and weigh |
| 3 | Blend fumaric acid with lactose for 10 min |
| 4 | Wet granulate fumaric acid and lactose and dry |
| 5 | Process dried wet granulation of step 4 with Comill and screen (40 mesh). Blend wet-granulated lactose/fumaric acid mixture with API (in 2 steps). Screen lubricant (sodium stearyl fumarate or stearic acid) and add lubricant to the mixture of API/lactose/fumaric acid |
| 6 | Blend lubricant with API/lactose/fumaric acid for 3 minutes |
| 7 | If necessary, add glidant (colloidal silica) to the mixture of step 6 |
| 8 | Compress the mixture of step 6 or step 7 with a 7/32 inch round tooling (80 mg target) |

API = Compound 1 di-tosylate salt

TABLE 18

Tablet Stability 1 month at 5° C., 25° C./60% RH, 40° C./75% RH for Formulation A

|  | Wet Granulation Compound 2 (%) | Dry Blend Compound 2 (%) |
|---|---|---|
| Initial | 0.06 | 0.07 |
| 5° C. | 0.06 | 0.10 |
| 25° C./60% RH | 0.25 | 0.59 |
| 40° C./75% RH | 0.82 | 1.5 |

TABLE 19

Tablets Composition

|  | % comp. | mg/tablet |
|---|---|---|
| Formulation A | | |
| Compound 1 di-tosylate salt, Form HI | 2.5 | 2.0 |
| Lactose Monohydrate Fast Flo NF | 85.5 | 68.4 |
| Fumaric Acid NF | 10.0 | 8.0 |
| Sodium Stearyl Fumarate NF | 2.0 | 1.6 |
|  | 100.0 | 80.0 |
| Formulation B | | |
| Compound 1 di-tosylate salt, Form HI | 2.5 | 2.0 |
| Lactose Monohydrate Fast Flo NF | 85.5 | 68.4 |
| Fumaric Acid NF | 10.0 | 8.0 |
| Stearic Acid NF | 1.5 | 1.2 |
| Colloidal Silica NF | 0.5 | 0.4 |
|  | 100.0 | 80 |

TABLE 20

Tablet Stability at 5° C., 25° C./60% RH, 40° C./75% RH for Formulation B
% Compound 2

| Condition | 1 m | 3 m | 6 m |
|---|---|---|---|
| 5° C. | 0.10 | 0.15 | 0.16 |
| 25° C./60% RH | 0.26 | 0.54 | 0.57 |
| 30° C./65% RH | 0.32 | 0.55 | 0.52 |
| 40° C./75% RH | 0.65 | 1.1 | 1.5 |
| Initial: 0.12% | | | |

Example 5. Capsule Formulation Prepared with Form HI of Compound 1 Di-Tosylate Salt A capsule formulation was prepared with the composition listed in Table 21 according to the process steps below and the wet granulation process described in Example 4. The stability was determined after storage for 3 months in 40 cc HDPE bottles at 25° C./60% RH and 40° C./75% RH. The stability results in Table 22 show reduced levels of compound 2.

| Steps | |
|---|---|
| 1 | Screen API-60 or 80 mesh and weigh |
| 2 | Screen fumaric acid and lactose (40 mesh), and weigh |
| 3 | Blend fumaric acid with lactose for 10 min |
| 4 | Wet granulate fumaric acid and lactose and dry |
| 5 | Process dried wet granulation of step 4 with Comill and screen (40 mesh). Blend wet-granulated lactose/fumaric acid mixture with API (in 2 steps). |
| 6 | Screen lubricant (stearic acid) and glidant (colloidal silicon dioxide), weigh-add to the mixture of API/lactose/fumaric acid |
| 7 | Blend with API/lactose/fumaric acid for 3 minutes. Discharge from blender |
| 8 | Fill into size 3 capsules |

TABLE 21

Compound 1 Capsule Formulation: 1 mg

|  | % comp. | mg/capsule |
|---|---|---|
| Compound 1 di-tosylate salt, Form HI | 2.5 | 2.0 |
| Lactose Monohydrate Fast Flo NF | 85.5 | 68.4 |
| Fumaric Acid NF | 10.0 | 8.0 |
| Stearic Acid NF | 1.5 | 1.2 |
| Colloidal Silica NF | 0.5 | 0.4 |
|  | 100.0 | 80 |

TABLE 22

Capsule Stability 3 month at 25° C./60% RH, 40° C./75% RH
1 mg Capsule Stability

| Condition | % Compound 2 |
|---|---|
| 25° C./60% RH | 0.43 |
| 40° C./75% RH | 0.88 |

Example 6
Synthesis of 1-{[4-(methoxymethyl)-4-({[(1R,2S)-2-phenylcyclopropyl]amino}methyl)piperidin-1-yl]methyl}cyclobutanecarboxylic acid bis(4-methylbenzenesulfonate) (12) (Compound 1 di-tosylate salt)
Scheme 1.
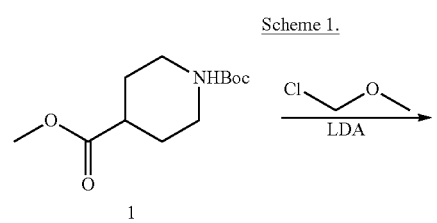
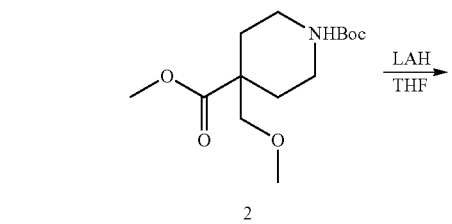
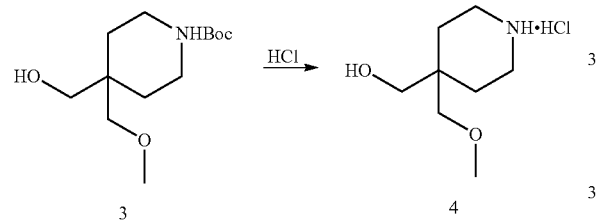
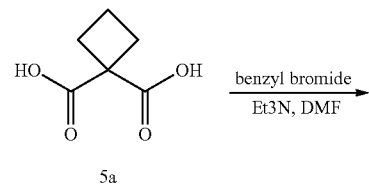
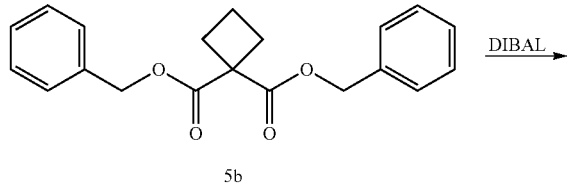
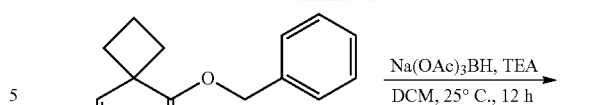
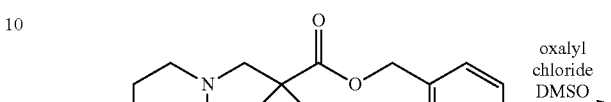
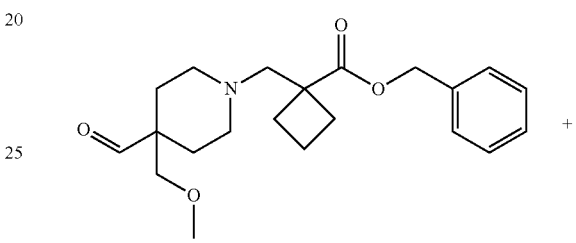
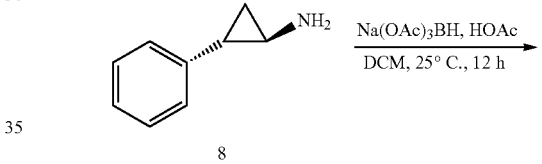
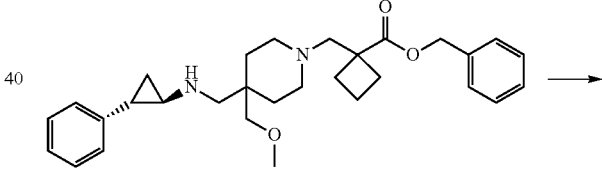
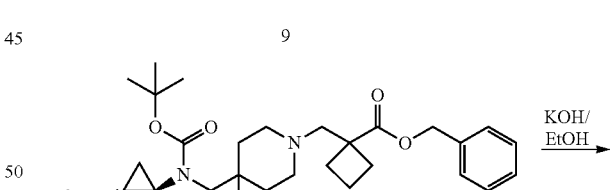
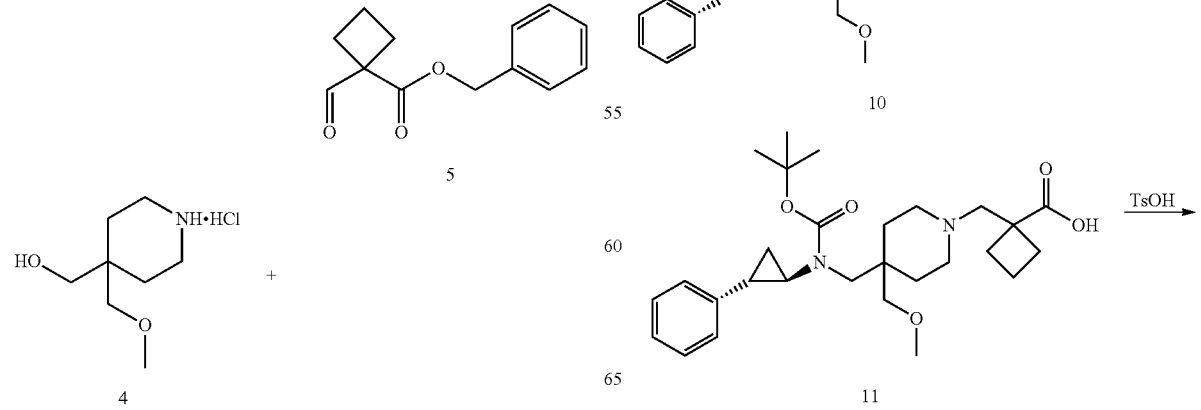

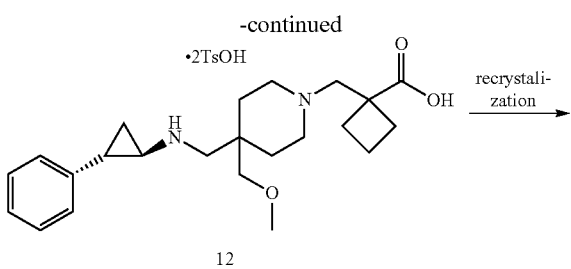

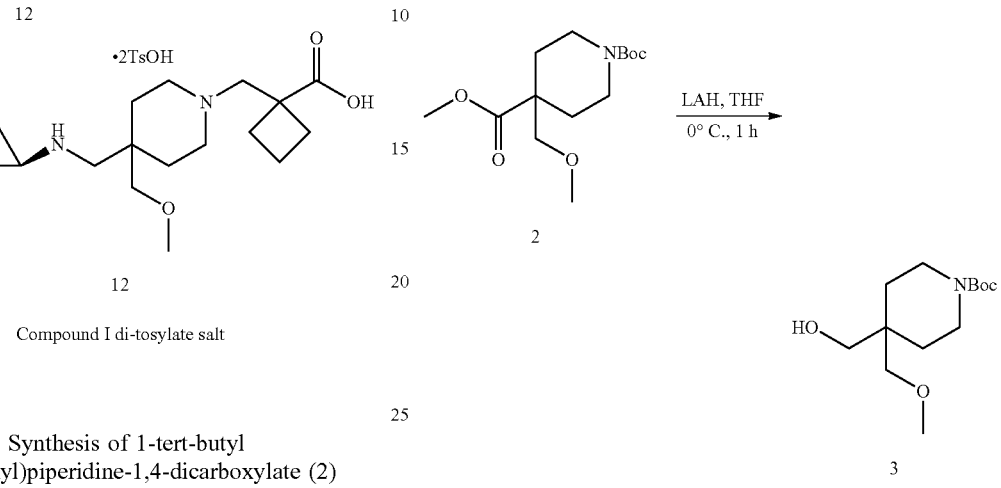

(400 MHz, CDCl$_3$) δ 3.85 (d, J=13.9 Hz, 2H), 3.74 (s, 3H), 3.39 (s, 2H), 3.31 (s, 3H), 3.02-2.90 (m, 2H), 2.13-2.03 (m, 2H), 1.40-1.46 (m, 11H).

Step 2. Synthesis of tert-butyl 4-(hydroxymethyl)-4-(methoxymethyl)piperidine-1-carboxylate (3)

Step 1. Synthesis of 1-tert-butyl 4-(methoxymethyl)piperidine-1,4-dicarboxylate (2)

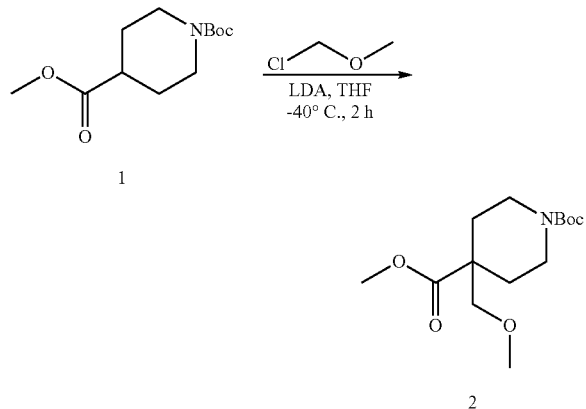

To a solution of N,N-diisopropylamine (165.0 mL, 1180 mmol) in THF was added 2.5 M n-butyllithium in hexane (0.46 L, 1150 mmol) at −78° C. The reaction mixture was stirred at −78° C. for 15 minutes, and warmed to 0° C. for 20 minutes.

The above prepared LDA solution was added to a flask containing 1-t-butyl 4-methyl piperidine-1,4-dicarboxylate (200.0 g, 822.03 mmol) in THF (2.4 L) at −78° C. The reaction mixture was stirred at −78° C. for 10 minutes, then warmed to −40° C. over 1 hour. The reaction mixture was re-cooled to −78° C., then chloromethyl methyl ether (93.6 mL, 1230 mmol) was added dropwise. The mixture was stirred for 2.5 hours allowing the reaction to come to room temperature. The reaction mixture was quenched with saturated aqueous NaHCO$_3$, and extracted with ethyl acetate (2×1.5 L). The combined organics were washed with water and brine, dried over MgSO$_4$, filtered and concentrated to give an oil product (2). The residue was used in the next step without further purification (quantitative yield). $^1$H NMR To a dried 22 L 5-neck round bottom flask equipped with stir shaft for mechanical stirring, thermocouple, N$_2$ inlet, addition tube and yellow cap for pressure release was charged 3225 mL dry THF. The solution was cooled to −15° C. using dry ice/IPA bath and charged 1.0 M lithium tetrahydroaluminate in THF (1180 mL, 1180 mmol) to the reactor via cannula directly from vender bottles (the additional LAH was used for EtOAc that is present in the substrate by NMR). The mixture was allowed to warm to −5° C. A solution of 1-tert-butyl 4-(methoxymethyl)piperidine-1,4-dicarboxylate (429.50 g, 1494.7 mmol) in THF (4000 mL) was prepared and transferred to a 12 L round bottom flask. The ester was slowly added to the LAH solution using positive N$_2$ pressure to deliver solution via addition tube (like a plastic cannula). The internal temperature was kept below 8° C. during addition by adjusting the rate of addition. The reaction mixture was stirred at 0° C. for 1 hour.

The reaction mixture was quenched using aq. 1.0N NaOH (260 mL). The initial 21 mL was added slowly under N$_2$. Vigorous H$_2$ evolution and a temperature increase were observed during this part of the quench. Temperature was not allowed to increase above 8° C. Solids began to form and aqueous addition could be performed more rapidly without noticeable gas evolution and temperature increase. Total quenching time was 20 minutes. The mixture was allowed to stir for 15 minutes to break up solids. Celite (500 g) was added and stirred for 45 minutes. The mixture was filtered. The filter cake was washed with ethyl acetate (EtOAc) (2000 mL). The filtrate was added to separation funnel and partitioned between EtOAc (6000 mL) and water (1000 mL). Layers were slow to separate. Some emulsion was observed. The material was purified by Biotage (0-30% EtOAc in hexane) to get pure product (3) (369.5 g, 95.3%). $^1$H NMR (400 MHz, CDCl$_3$) δ 3.62 (s, 2H), 3.45 (d, J=2.3 Hz, 1H), 3.41-3.32 (m, 7H), 2.33 (s, 2H), 1.55-1.42 (m, 13H).

Step 3. Synthesis of [4-(methoxymethyl)piperidin-yl]methanol hydrochloride (4)

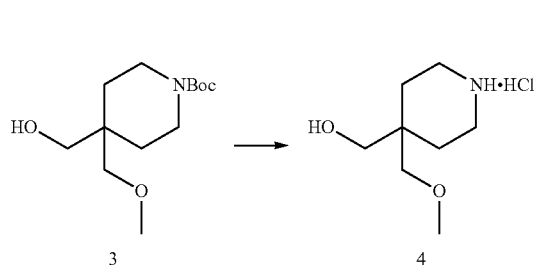

To a solution of tert-butyl 4-(hydroxymethyl)-4-(methoxymethyl)piperidine-1-carboxylate (113.70 g, 438.42 mmol) in DCM (0.667 L) was added 4.0 M HCl in dioxane (0.767 mL, 3070 mmol) at 0° C. The reaction mixture was stirred at room temperature for 1 hour. Filtration of the reaction mixture provided pure product (4) (77.0 g, 89.8%). LC-MS calculated for $C_{24}H_{18}ClNO_2$ $[M+H]^+$ m/z: 196.1. found 196.1. $^1H$ NMR (400 MHz, DMSO) δ 9.02 (s, 1H), 3.31-3.18 (m, 7H), 2.98 (d, J=6.0 Hz, 4H), 1.61-1.53 (m, 4H).

Step 4. Synthesis of dibenzyl cyclobutane-1,1-dicarboxylate(5b)

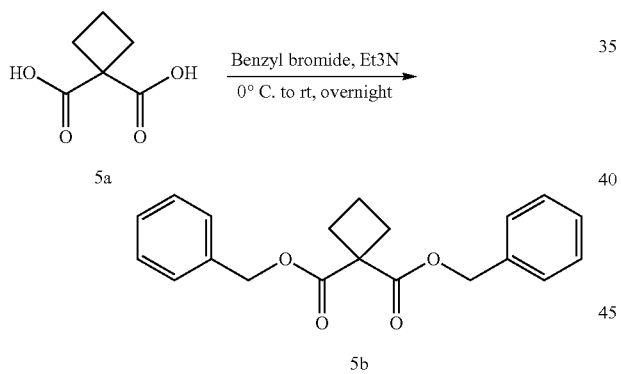

To a solution of 1,1-cyclobutanedicarboxylic acid (50.00 g, 346.9 mmol) in DMF (180 mL) was added trimethylamine (102 mL, 728 mmol) at 0° C. (keeping temperature below 15° C. during the addition). The reaction mixture was stirred at 0° C. for 15 minutes, then benzyl bromide (144 mL, 1210 mmol) was added (keeping temperature below 30° C.). After 10 minutes, the ice bath was removed. The reaction mixture was stirred at room temperature overnight.

To the reaction mixture was added water (300 mL). The mixture was partitioned between DCM (300 mL) and aqueous solution. The organics were washed with 1.0 N HCl solution (200 mL), 10% NaHCO₃ solution (200 mL) and brine (200 mL), then dried over MgSO₄ and concentrated to give crude material (5b) (111.10 g), which was used for next step. $^1H$ NMR (400 MHz, CDCl₃) δ 7.37-7.24 (m, 10H), 5.17 (s, 4H), 2.64-2.55 (t, J=8.0 Hz, 4H), 2.02 (p, J=8.0 Hz, 2H).

Step 5. Synthesis of benzyl 1-formylcyclobutanecarboxylate (5)

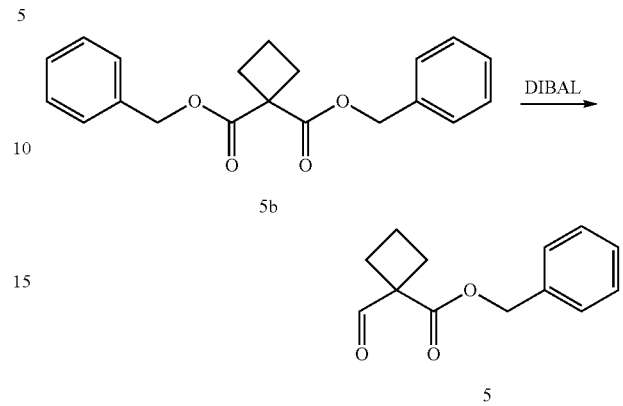

To a solution of dibenzyl cyclobutane-1,1-dicarboxylate (30.00 g, 92.49 mmol) in DCM (200.00 mL) at −75° C. was added 1.0 M diisobutylaluminum hydride in DCM (185 mL) dropwise. The temperature was controlled between −70° C. and −60° C. The reaction mixture was stirred at −75° C. for 1 hour.

The reaction was quenched with slow addition of 1.0 M hydrogen chloride in water (200.0 mL). The resulting mixture was warmed to room temperature and stirred for another 30 minutes. The mixture was partitioned between DCM and aqueous solution. The organic layer was washed with water and brine, dried over MgSO₄ and concentrated to give crude product. Biotage (0-10% EtOAc in hexane) gave pure product (5) 11.6 g. $^1H$ NMR (400 MHz, CDCl₃) δ 9.82 (s, 1H), 7.37 (p, J=4.3 Hz, 5H), 5.25 (s, 2H), 2.51 (t, J=8.0 Hz, 4H), 2.11-1.89 (p, J=8.0 Hz, 2H).

Step 6. Synthesis of benzyl 1-((4-(hydroxymethyl)-4-(methoxymethyl)piperidin-1-yl)methyl)cyclobutane-1-carboxylate (6)

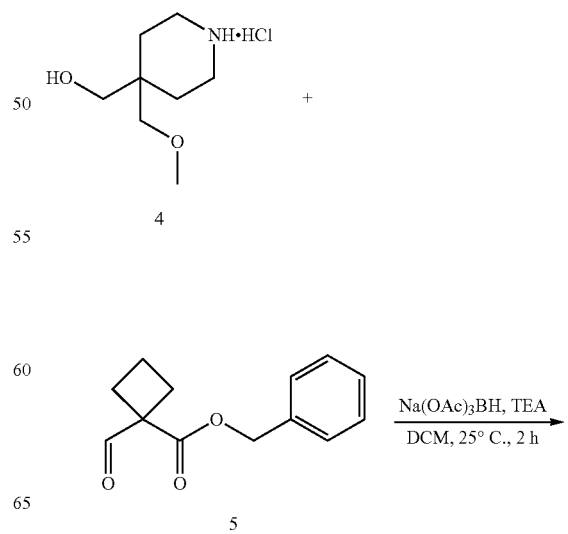

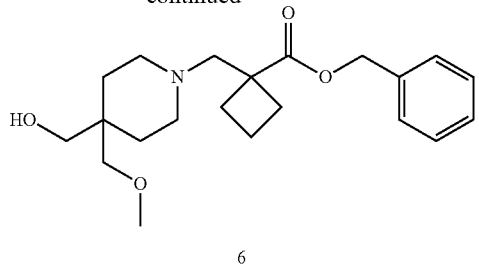

To a solution of [4-(methoxymethyl)piperidin-4-yl]methanol hydrochloride (10.8 g, 55.4 mmol) and benzyl 1-formylcyclobutanecarboxylate (14.40 g, 52.78 mmol) in DCM (300 mL) was added trimethylamine (18.4 mL, 132 mmol) at room temperature. The reaction mixture was stirred at room temperature for 1 hour. Sodium triacetoxyborohydride (22.4 g, 106 mmol) was added with a water bath portionwise. The reaction mixture was stirred at room temperature overnight.

To the reaction mixture was added saturated NaHCO$_3$ solution (200 mL). The mixture was partitioned between DCM and NaHCO$_3$ solution. The organics were dried and concentrated to provide oil crude product. Biotage (EtOAc/hexane: 0-45%) gave pure product (6) (16.6 g, 87%). LC-MS calculated for C$_{21}$H$_{31}$NO$_4$ [M+H]$^+$ m/z: 362.2. found 362.2. $^1$H NMR (400 MHz, CD$_3$CN) δ 7.47-7.30 (m, 5H), 5.16 (s, 2H), 3.38 (s, 2H), 3.30 (s, 3H), 3.24 (s, 2H), 2.71 (s, 2H), 2.43 (ddd, J=12.1, 9.4, 7.2 Hz, 2H), 2.36-2.28 (m, 4H), 2.09-1.82 (m, 4H), 1.39-1.31 (m, 4H).

Step 7. Synthesis of Benzyl 1-{[4-formyl-4-(methoxymethyl)piperidin-1-yl]methyl}cyclobutanecarboxylate (7)

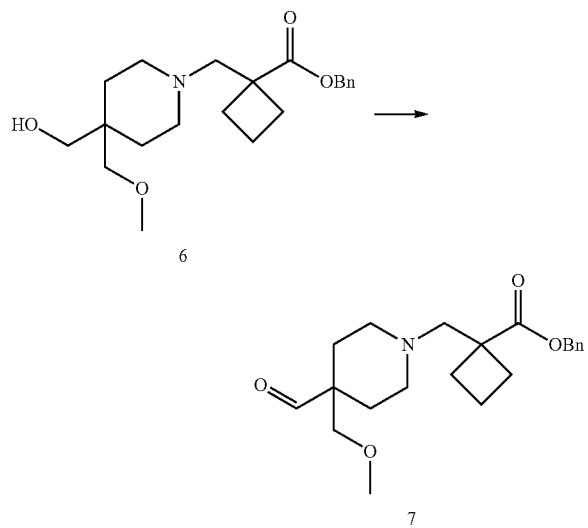

To a solution of oxalyl chloride (226 mL, 339 g, 2.67 moles) in dichloromethane (1.1 L) was added a solution of dimethyl sulfoxide (378 mL, 416 g, 5.32 moles) in dichloromethane (500 mL) over one hour, while maintaining the internal temperature at below −55° C. After stirring at −50° C. for 30 minutes, a solution of benzyl 1-((4-(hydroxymethyl)-4-(methoxymethyl)piperidin-1-yl)methyl)cyclobutane-1-carboxylate (475 g, 1.315 mol) in dichloromethane (1.1 L) was added over 45 minutes, maintaining the internal temperature below −50° C. After stirring at −50° C. for 30 minutes, triethylamine (1480 mL, 10.62 moles) was added. The reaction temperature rose to 15° C. during the addition. After stirring for 20 minutes, ice cold water (5 L) was added and the layers were separated. The organic layer was washed with water (2 L) and 10% sodium bicarbonate (6.2 L). Each aqueous layer was re-extracted with dichloromethane (3.5 L). The combined organic layers were concentrated under reduced pressure. The crude product was purified over silica gel (5 kg), eluting with a gradient 0 to 100% ethyl acetate in heptane to give compound (7) (402 g, 85% yield, 98% purity) as colorless oil. LC-MS calculated for C$_{21}$H$_{29}$NO$_4$ [M+H]$^+$ m/z: 361.2. found 361.2. $^1$H NMR (400 MHz, CD$_3$CN) δ 9.47 (s, 1H), 7.47-7.33 (m, 5H), 5.16 (s, 2H), 3.38 (s, 2H), 3.26 (s, 3H), 2.67 (s, 2H), 2.54-2.38 (m, 4H), 2.16-1.93 (m, 4H), 1.91-1.78 (m, 4H), 1.38 (ddd, J=13.9, 10.3, 4.0 Hz, 2H).

Step 8. Synthesis of benzyl 1-((4-(methoxymethyl)-4-(((1R,2S)-2-phenylcyclopropylamino)methyl)piperidin-1-yl)methyl)cyclobutanecarboxylate (9) and Benzyl 1-{[4-({(tert-butoxycarbonyl)[(1R,2S)-2-phenylcyclopropyl]amino}methyl)-4-(methoxymethyl)piperidin-1-yl]methyl}cyclobutanecarboxylate (10)

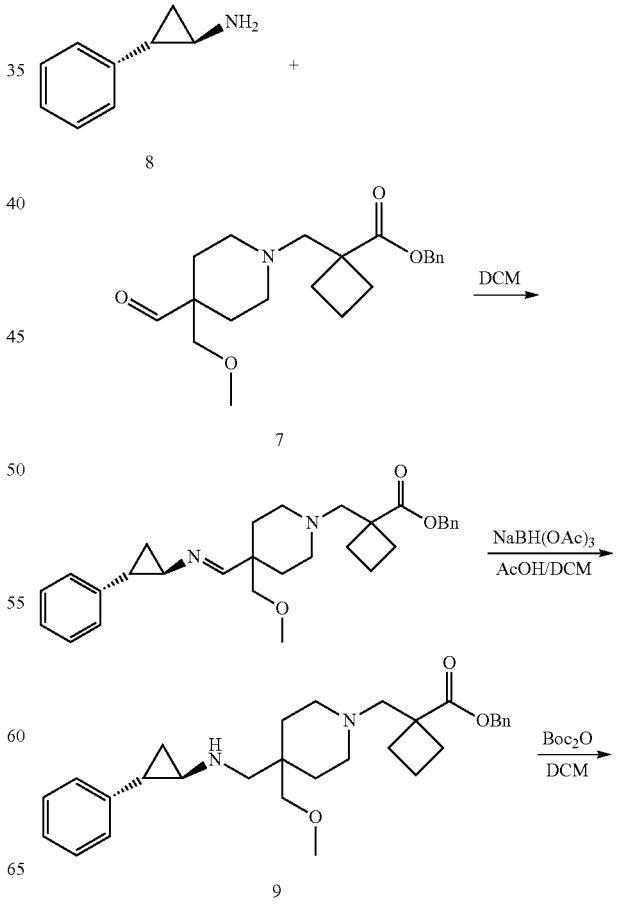

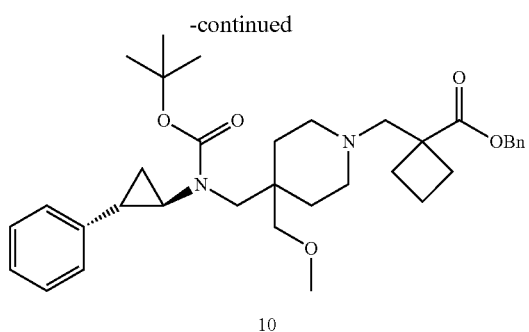

10

Benzyl 1-{[4-formyl-4-(methoxymethyl)piperidin-1-yl]methyl}cyclobutanecarboxylate (7) (136.10 g, 378.62 mmol) and (1R,2S)-2-phenylcyclopropanamine (8) (61.0 g, 458.0 mmol) were mixed in methylene chloride (1225 mL). The mixture was then concentrated under vacuum with a bath temperature of 40° C. The oily residue was re-dissolved in methylene chloride (1225 mL). The solution was then concentrated under vacuum with a bath temperature of 40° C. The formation of imine was confirmed by LC-MS at pH 10.

The residue was dissolved in methylene chloride (1225 mL), acetic acid (45.1 mL, 793.0 mmol) was added, followed by sodium triacetoxyborohydride (79.4 g, 793.0 mmol). The mixture was stirred for 1.5 hours. HPLC indicated the completion of the reaction. Methylene chloride (1225 mL) was added to dilute the reaction. To the mixture was added 7% aqueous sodium bicarbonate (2449.6 g), the mixture was stirred for 30 minutes and DCM phase was collected. The organic phase was washed with aqueous 7% sodium bicarbonate (2449.6 g), then concentrated under vacuum to about 1300-1500 mL volume, and used directly for the next step.

To the above solution was added di-tert-butyldicarbonate (180.0 g, 377.63 mmol). The mixture was stirred at room temperature overnight. To the reaction mixture was added aqueous 7% sodium bicarbonate and after stirring for 30 minutes, the organic phase was collected, dried over $MgSO_4$ and concentrated. The residue was purified by Biotage (0-20% ethyl acetate in hexane, checked by anisaldehyde as stain) to give compound (10) (190.0 g, 87.2%). Compound (9): LC-MS calculated for $C_{30}H_{40}N_2O_3$ [M+H]$^+$ m/z: 477.3. found 477.3. $^1$H NMR (400 MHz, $D_2O$) δ 7.49-7.23 (m, 8H), 7.18 (d, J=7.3 Hz, 2H), 5.23 (s, 2H), 3.56 (s, 2H), 3.34 (s, 3H), 3.23 (s, 2H), 3.16 (s, 3H), 3.01 (s, 2H), 2.48 (dt, J=11.2, 8.1 Hz, 3H), 2.17-1.93 (m, 4H), 1.55-1.49 (m, 5H), 1.37 (q, J=7.2 Hz, 1H). Compound (10): LC-MS calculated for $C_{35}H_{48}N_2O_5$ [M+H]$^+$ m/z: 577.3. found 577.3. $^1$H NMR (400 MHz, $CD_3CN$) δ 7.46-7.23 (m, 8H), 7.15 (dd, J=28.9, 7.3 Hz, 2H), 5.15 (s, 2H), 3.44 (d, J=14.5 Hz, 1H), 3.31-3.07 (m, 5H), 2.78-2.67 (m, 3H), 2.43 (dd, J=11.1, 5.8 Hz, 4H), 2.26 (ddd, J=24.0, 11.7, 4.7 Hz, 4H), 2.08-1.95 (m, 4H), 1.86 (p, J=7.3, 6.6 Hz, 2H), 1.55-1.44 (m, 1H), 1.44-1.28 (m, 13H), 1.21 (dq, J=13.5, 6.8 Hz, 1H).

Compound (10) can also be purified by reacting compound (10) with L-tartaric acid in the presence of isopropanol, methanol, and n-heptane to form compound (10) L-tartrate and reacting compound (10) L-tartrate with $NaHCO_3$ in dichloromethane to provide purified compound (10). The corresponding salt formation and neutralization procedures are described below.

Crude compound 10 and 2-propanol are stirred at 15-30° C. for about 15 minutes until a solution is obtained. L-Tartaric acid and methanol are stirred at 15-30° C. for about 1 hour until a solution is obtained. The L-tartaric acid solution is then added to the solution of crude compound 10 and the reaction mixture is stirred at 15-30° c. for about 1 hour. n-Heptane is then added to the reaction mixture and the resulting mixture is stirred at 15-30° C. for about 1 hour. The reaction mixture is filtered and the wet cake is washed with n-heptane and dried to afford the corresponding L-tartaric acid salt of compound 10.

Dichloromethane (DCM) and L-tartaric acid salt of compound 10 are charged to a reactor at ambient temperature, and aqueous $NaHCO_3$ solution is charged to the reactor while maintaining the reaction mixture at no more than 30° C. The reaction mixture is stirred at 15-30° C. for about 30 minutes and the phases are separated. The organic phase is concentrated under reduced pressure until the distillation stops. The distillation residue is then treated with ethanol (EtOH) and the resulting solution of compound 10 in ethanol (EtOH) is directly used in the subsequent reaction without further purification.

Step 9. Synthesis of 1-{[4-({(tert-butoxycarbonyl)[(1R,2S)-2-phenylcyclopropyl]amino}methyl)-4-(methoxymethyl)piperidin-1-yl]methyl}cyclobutanecarboxylic acid (11)

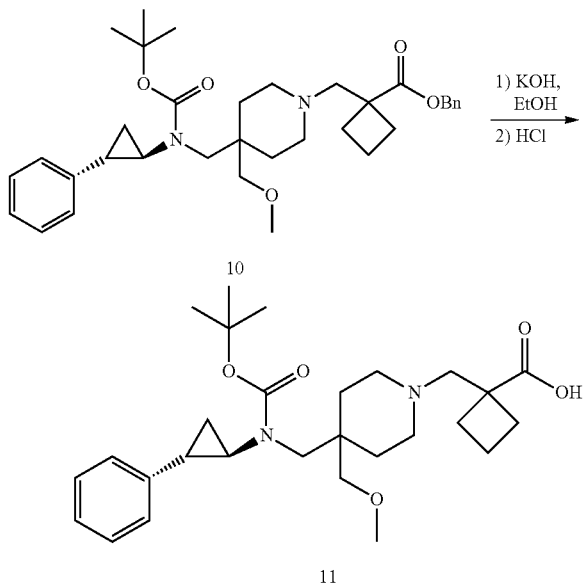

Benzyl 1-{[4-({(tert-butoxycarbonyl)[(1R,2S)-2-phenylcyclopropyl]amino}methyl)-4-(methoxymethyl)piperidin-1-yl]methyl}cyclobutanecarboxylate (10) (449.10 g, 778.65 mmol) was dissolved in ethanol (1570 mL). The solution was concentrated in vacuo with a bath temperature at 40° C. The residue was again dissolved in ethanol (1570 mL) and the solution was concentrated using in vacuo with bath temperature at 40° C. To the residue was added a solution of potassium hydroxide (89.9 g, 1604 mmol) in ethanol (1570 mL) and water (224.6 mL). The mixture was then heated in a bath at 40° C. HPLC indicated the reaction was complete (PCT 0.5%) after 8 hours.

A vacuum was applied to remove ethanol, then water was added (2000 mL), the mixture concentrated down, and then the process was repeated one more time to yield crude product. Water (1570 mL), 2-methoxy-2-methylpropane (2246 mL) and sodium chloride (200.0 mL) were added to the crude product. The organic layer was then collected, and concentrated. The residue was re-dissolved in water (2000 mL), and then concentrated to dryness.

The residue was re-dissolved in water (2000 mL) and the solution was washed again with 2-methoxy-2-methylpropane (2246 mL). The repeated washing with MTBE was performed until the benzyl alcohol was less than 0.5% in aqueous layer. The aqueous solution was then cooled in an ice bath before being treated dropwise with an aqueous HCl solution, made from the concentrated hydrochloric acid (conc. HCl, 95.0 g, 951 mmol) and water (450.0 g), until pH 5.

The mixture was extracted with methylene chloride (3000 mL×2) twice. The combined DCM layers were concentrated to give the desired product (11) as a white solid, which was used directly in the next step. LC-MS calculated for $C_{28}H_{42}N_2O_5$ [M+H]$^+$ m/z: 487.3. found 487.3. $^1$H NMR (400 MHz, CD$_3$CN) δ 7.29 (t, J=7.5 Hz, 2H), 7.17 (dd, J=24.1, 7.3 Hz, 3H), 3.53 (d, J=14.4 Hz, 1H), 3.34-3.14 (m, 5H), 3.01-2.73 (m, 7H), 2.43-2.36 (m, 2H), 2.21-1.82 (m, 7H), 1.79-1.58 (m, 4H), 1.38 (s, 9H), 1.23 (q, J=6.5 Hz, 1H).

Step 10. Synthesis of 1-{[4-(methoxymethyl)-4-({ [(1R,2S)-2-phenylcyclopropyl]amino}methyl)piperidin-1-yl]methyl}cyclobutanecarboxylic acid bis(4-methylbenzenesulfonate) (12)

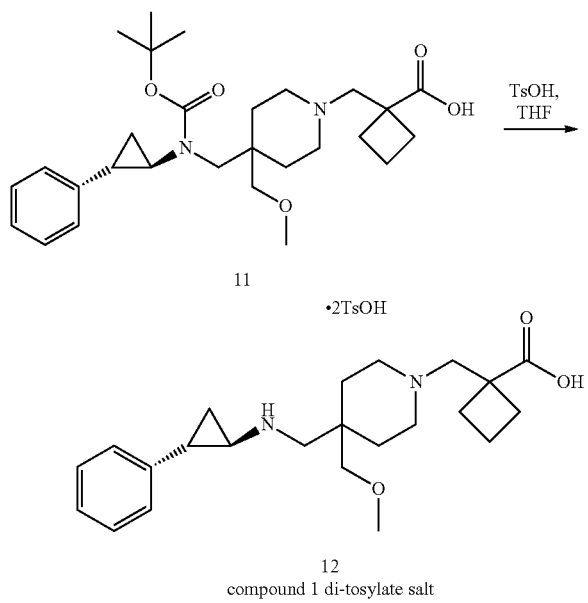

1-{[4-({(tert-Butoxycarbonyl)[(1R,2S)-2-phenylcyclopropyl]amino}methyl)-4-(methoxymethyl)piperidin-1-yl]methyl}cyclobutanecarboxylic acid (11) (370.0 g, 722.4 mmol) was dissolved in tetrahydrofuran (2000.0 mL). To the solution was added p-toluenesulfonic acid monohydrate (300.0 g, 1577 mmol). The mixture was heated to 55-60° C. In 14 hours, HPLC indicated the reaction was complete (SM<1%). To the mixture while heating was added 2-methoxy-2-methylpropane (4000 mL) through an addition funnel. The reaction mixture was kept stirring for 6 hours at 55° C.-60° C. before disconnection of the heat. The mixture was cooled down to room temperature and stirred overnight. Solid product was collected by filtration and the cake was washed with 2-methoxy-2-methylpropane (1000 mL) twice, and dried on the filter overnight. The material 1-{[4-(methoxymethyl)-4-({[(1R,2S)-2-phenylcyclopropyl]amino}methyl)piperidin-1-yl]methyl}cyclobutanecarboxylic acid bis(4-methylbenzenesulfonate) (12) also known as 1-{[4-(methoxymethyl)-4-({[(1R,2S)-2-phenylcyclopropyl]amino}methyl)piperidin-1-yl]methyl}cyclobutanecarboxylic acid ditosylate salt was used directly for recrystallization.

Step 11. Crystalline Form I of 1-{[4-(methoxymethyl)-4-({[(1R,2S)-2-phenylcyclopropyl]amino}methyl)piperidin-1-yl]methyl}cyclobutanecarboxylic acid bis(4-methylbenzenesulfonate (Compound 1 di-tosylate salt, Form I)

1-{[4-(Methoxymethyl)-4-({[(1R,2S)-2-phenylcyclopropyl]amino}methyl)piperidin-1-yl]methyl}cyclobutanecarboxylic acid bis(4-methylbenzenesulfonate) (12) (532.9 g, 729.1 mmol) was mixed with 2-butanone (7223 mL). The mixture was heated to 55° C. (internal temperature set) to become a clear solution. The hot solution was polish filtered through an inline filter, and the clear solution was distilled off under vacuum to about 4 L volume while being heated at 55° C. (internal temperature set). To the solution was added heptane (4676 mL) while stirring. After the addition, the mixture was kept at 55° C. (internal temperature set) for 4 hours, then allowed to cool to room temperature. The mixture was stirred overnight. The solid was filtered and washed with a mixture of heptane (1000.0 mL) and 2-butanone (1000.0 mL). The recrystallized product 1-{[4-(methoxymethyl)-4-({[(1R,2S)-2-phenylcyclopropyl]amino}methyl)piperidin-1-yl]methyl}cyclobutanecarboxylic acid bis(4-methylbenzenesulfonate) (12) was dried on the filter overnight, and then under high vacuum at 50° C. overnight to give pure product. LC-MS calculated for $C_{37}H_{50}N_2O_9S_2$ [M+H]$^+$ m/z: 387.2; found 387.2. $^1$H NMR (400 MHz, MeOD) δ 7.73 (d, J=8.2 Hz, 4H), 7.34-7.19 (m, 7H), 7.15 (d, J=7.2 Hz, 2H), 3.70-3.51 (m, 4H), 3.43 (d, J=18.4 Hz, 7H), 3.36-3.22 (m, 3H), 3.13-2.97 (m, 1H), 2.67-2.50 (m, 3H), 2.38 (s, 6H), 2.21 (q, J=9.5, 8.6 Hz, 2H), 2.05 (dt, J=28.5, 11.6 Hz, 2H), 1.94-1.78 (m, 1H), 1.66-1.55 (m, 1H), 1.32 (d, J=8.0 Hz, 2H), 0.92 (t, J=6.8 Hz, 1H).

Example 7

Preparation of Crystalline Forms

Form HI of Compound 1 di-tosylate salt was prepared during the process of drying a wet sample of Compound 1 di-tosylate salt, Form I, under ambient conditions. Form I slowly absorbed atmospheric moisture and gradually changed to crystalline Form HI. Under storage conditions of 25° C./60% RH and 40° C./75% RH, Form I was also converted to Form HI. Form HI can also be generated by purging humidified air (e.g., 60-85% RH) through Form I solid.

Form HII was prepared by slurring of Form I in water for 3 days at room temperature. The resulted suspension was filtered. The residual solid was collected and air dried for 5-7 days at ambient condition.

Form HIII was prepared by drying Form HI on Vapor Sorption Analyzer (TA Instruments VTI-SA$^+$) at 40° C. with 0% RH N$_2$ for 3 h and then exposing it to humidity at about 30-50% RH at 25° C. for 1 day. Form HIII can change to Form HI when it is further exposed to high humidity at about 60-85% RH. Form DH was prepared by drying Form HI on Vapor Sorption Analyzer (TA Instruments VTI-SA+) at 25° C. with 0% RH N$_2$ for 2 days. When Form DH is exposed to humidity, it can absorb water and change to Form HIII at about 30-50% RH or to Form HI at high humidity around 60-85% RH.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A pharmaceutical formulation in solid oral dosage form comprising:
   (a) an inhibitor of LSD1 which is Compound 1 di-tosylate salt of the formula:

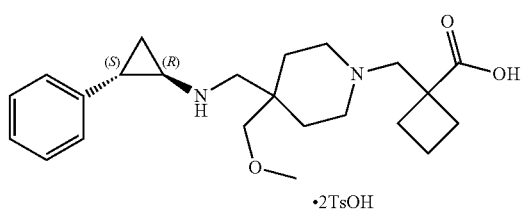

·2TsOH or a solvate or hydrate thereof, and
   (b) an organic acid selected from the group consisting of ascorbic acid, citric acid, fumaric acid, lactic acid, maleic acid, malic acid, sorbic acid, succinic acid, tartaric acid, and hydrates or solvates thereof, wherein the organic acid is from about 1% and to about 50% by weight.

2. The pharmaceutical formulation of claim 1, further comprising a diluent.

3. The pharmaceutical formulation of claim 1, wherein the organic acid is fumaric acid or citric acid.

4. The pharmaceutical formulation of claim 3, wherein the organic acid is fumaric acid.

5. The pharmaceutical formulation of claim 4, comprising about 1 wt % to about 15 wt % of fumaric acid.

6. The pharmaceutical formulation of claim 4, comprising about 5 wt % to about 15 wt % of fumaric acid.

7. The pharmaceutical formulation of claim 4, comprising about 9 wt % to about 11 wt % of fumaric acid.

8. The pharmaceutical formulation of claim 4, comprising about 10 wt % of fumaric acid.

9. The pharmaceutical formulation of claim 1, comprising about 1 wt % to about 5 wt % of the LSD1 inhibitor.

10. The pharmaceutical formulation of claim 1, comprising about 2 wt % to about 4 wt % of the LSD1 inhibitor.

11. The pharmaceutical formulation of claim 1, comprising about 3 wt % of the LSD1 inhibitor.

12. The pharmaceutical formulation of claim 2, wherein the diluent is lactose or mannitol.

13. The pharmaceutical formulation of claim 12, wherein the lactose is lactose monohydrate or lactose-316 Fast Flo®.

14. The pharmaceutical formulation of claim 13, comprising about 80 wt % to about 97 wt % of lactose monohydrate.

15. The pharmaceutical formulation of claim 13, comprising about 85 wt % to about 97 wt % of lactose monohydrate.

16. The pharmaceutical formulation of claim 1 further comprising a lubricant, glidant, or both.

17. The pharmaceutical formulation of claim 16, wherein the lubricant is sodium stearyl fumarate or stearic acid.

18. The pharmaceutical formulation of claim 17, wherein the lubricant is sodium stearyl fumarate.

19. The pharmaceutical formulation of claim 18, comprising about 1 wt % to about 5 wt % of sodium stearyl fumarate.

20. The pharmaceutical formulation of claim 19, comprising about 2 wt % of sodium stearyl fumarate.

21. The pharmaceutical formulation of claim 17, wherein the lubricant is stearic acid.

22. The pharmaceutical formulation of claim 21, comprising about 1 wt % to about 5 wt % of stearic acid.

23. The pharmaceutical formulation of claim 21, comprising about 2 wt % of stearic acid.

24. The pharmaceutical formulation of claim 16, wherein the glidant is colloidal silica.

25. The pharmaceutical formulation of claim 1, further comprising
   lactose or mannitol, or a solvate or hydrate thereof wherein the organic acid is fumaric acid.

26. The pharmaceutical formulation of claim 25, wherein:
   (a) said Compound 1 di-tosylate salt, or a solvate or hydrate thereof, is about 1 wt % to about 5 wt % of said formulation;
   (b) said fumaric acid is about 1 wt % to about 15 wt % of said formulation; and
   (c) said lactose, or a solvate or hydrate thereof, is about 80 wt % to about 97 wt % of said formulation.

27. The pharmaceutical formulation of claim 25 further comprising sodium stearyl fumarate.

28. The pharmaceutical formulation of claim 25 further comprising stearic acid.

29. The pharmaceutical formulation of claim 27, wherein:
   (a) said Compound 1 di-tosylate salt, or a solvate or hydrate thereof, is about 1 wt % to about 5 wt % of said formulation;
   (b) said fumaric acid is about 1 wt % to about 15 wt % of said formulation;
   (c) said lactose, or a solvate or hydrate thereof, is lactose monohydrate and is about 80 wt % to about 97 wt % of said formulation; and
   (d) said sodium stearyl fumarate is about 1 wt % to about 5 wt % of said formulation.

30. The pharmaceutical formulation of claim 28, wherein:
   (a) said Compound 1 di-tosylate salt, or a solvate or hydrate thereof, is about 1 wt % to about 5 wt % of said formulation;
   (b) said fumaric acid is about 1 wt % to about 15 wt % of said formulation;
   (c) said lactose, or solvate or hydrate thereof, is lactose monohydrate and is about 80 wt % to about 97 wt % of said formulation; and
   (d) said stearic acid is about 1 wt % to about 5 wt % of said formulation.

31. The pharmaceutical formulation of claim 1, further comprising a disintegrant.

32. The pharmaceutical formulation of claim 31, wherein the disintegrant is croscarmellose sodium, sodium starch glycolate or crospovidone.

33. The pharmaceutical formulation of claim 1, wherein the Compound 1 di-tosylate salt, or hydrate or solvate thereof, is in crystalline form.

34. The pharmaceutical formulation of claim 33, wherein the crystalline form comprises Form I, wherein Form I has a characteristic X-ray powder diffraction (XRPD) peak, in terms of 2-theta, at about 3.6 degrees.

35. The pharmaceutical formulation of claim 33, wherein the crystalline form comprises Form HI, wherein Form HI has a characteristic XRPD peak, in terms of 2-theta, at about 7.0 degrees.

36. The pharmaceutical formulation of claim 1, wherein the dosage form is a tablet or capsule.

37. The pharmaceutical formulation of claim 2, prepared by a method comprising blending Compound 1 di-tosylate salt, or a solvate or hydrate thereof, an organic acid and one or more portions of a diluent to form the pharmaceutical formulation.

\* \* \* \* \*

UNITED STATES PATENT AND TRADEMARK OFFICE
CERTIFICATE OF CORRECTION

| | | |
|---|---|---|
| PATENT NO. | : 10,166,221 B2 | Page 1 of 1 |
| APPLICATION NO. | : 15/493514 | |
| DATED | : January 1, 2019 | |
| INVENTOR(S) | : William L. Rocco et al. | |

It is certified that error appears in the above-identified patent and that said Letters Patent is hereby corrected as shown below:

In the Claims

Column 52, Line 26, Claim 25, delete "thereof" and insert -- thereof; --.

Signed and Sealed this
Nineteenth Day of March, 2019

Andrei Iancu
*Director of the United States Patent and Trademark Office*